(12) United States Patent
Golden et al.

(10) Patent No.: US 8,105,345 B2
(45) Date of Patent: *Jan. 31, 2012

(54) ANASTOMOSIS APPARATUS AND METHODS

(75) Inventors: Steve Golden, Menlo Park, CA (US);
Laurent Schaller, Los Altos, CA (US);
Demetri Mavroidis, Las Vegas, NV
(US); Stephen Ainsworth, Wilmington,
NC (US); Kathleen Woodside, Portola
Valley, CA (US); Liem Ho, Mountain
View, CA (US)

(73) Assignee: Medtronic, Inc., Minneapolis, MN (US)

( * ) Notice: Subject to any disclaimer, the term of this patent is extended or adjusted under 35 U.S.C. 154(b) by 582 days.

This patent is subject to a terminal disclaimer.

(21) Appl. No.: 10/340,161

(22) Filed: Jan. 10, 2003

(65) Prior Publication Data
US 2004/0068276 A1    Apr. 8, 2004

Related U.S. Application Data

(60) Provisional application No. 60/415,997, filed on Oct. 4, 2002.

(51) Int. Cl.
*A61B 17/08* (2006.01)
(52) U.S. Cl. .................................. 606/153; 606/206
(58) Field of Classification Search .............. 606/151, 606/152, 153, 158, 217, 219, 157, 144, 148, 606/222, 141, 149, 150, 154, 155, 156; 623/2.11
See application file for complete search history.

(56) References Cited

U.S. PATENT DOCUMENTS

| 43,098 | A | 6/1864 | Cooper |
| 636,728 | A | 11/1899 | Kindel |
| 655,190 | A | 8/1900 | Bramson |
| 1,087,186 | A | 2/1914 | Scholfield |
| 1,167,014 | A | 1/1916 | O'Brien |
| 1,167,015 | A | 1/1916 | O'Brien |
| 1,539,221 | A | 5/1925 | John |
| 1,583,271 | A | 5/1926 | Biro |
| 1,625,602 | A | 4/1927 | Gould et al. |
| 1,867,623 | A | 7/1932 | Hoffman |
| 1,867,624 | A | 7/1932 | Hoffman |

(Continued)

FOREIGN PATENT DOCUMENTS

DE    0219999    3/1910

(Continued)

OTHER PUBLICATIONS

"VCS Clip Applier System," published in 1995 by Auto Suture Company, a Division of U.S. Surgical Corporation.

(Continued)

*Primary Examiner* — Tuan Nguyen

(57) ABSTRACT

A system for anastomosing a first tubular structure to a second tubular structure having an opening formed therein comprises a support device having a plurality of arms forming spaces therebetween and a plurality of piercing members slidably coupled to the arms. The support device piercing members have a retracted state and an extended state to support the first tubular structure thereon for placement within an opening in the second tubular structure to facilitate anastomosing the tubular structures together. The arms can be configured to urge the first tubular structure against the portion of the second tubular structure surrounding the opening to form a seal therebetween. According to one embodiment, a plurality of discrete fasteners are provided to pass through the support device spaces and the first and second tubular structures. In another embodiment, fasteners are integrated into the support device and releasably coupled thereto for delivery to the anastomosis site.

33 Claims, 37 Drawing Sheets

U.S. PATENT DOCUMENTS

| | | |
|---|---|---|
| 2,201,610 A | 5/1940 | Dawson |
| 2,240,330 A | 4/1941 | Flagg et al. |
| 2,256,382 A | 9/1941 | Dole |
| 2,264,679 A | 12/1941 | Ravel |
| 2,413,142 A | 12/1946 | Jones et al. |
| 2,430,293 A | 11/1947 | Howells |
| 2,505,355 A | 4/1950 | Gusberg et al. |
| 2,505,358 A | 4/1950 | Gusberg, et al. |
| 2,516,710 A | 7/1950 | Mascolo |
| 2,715,486 A | 8/1955 | Marcoff-Moghadam |
| 2,890,519 A | 6/1959 | Storz, Jr. |
| 2,940,452 A | 6/1960 | Smialowski |
| 3,055,689 A | 9/1962 | Jorgensen |
| 3,057,355 A | 10/1962 | Smialowski |
| 3,082,426 A | 3/1963 | Miles |
| 3,143,742 A | 8/1964 | Cromie |
| 3,150,379 A | 9/1964 | Brown |
| 3,180,337 A | 4/1965 | Smialowski |
| 3,249,104 A | 5/1966 | Hohnstein |
| 3,274,658 A | 9/1966 | Pile |
| 3,452,742 A | 7/1969 | Muller |
| 3,506,012 A | 4/1970 | Brown |
| 3,509,882 A | 5/1970 | Blake |
| 3,547,103 A | 12/1970 | Cook |
| 3,570,497 A | 3/1971 | Lemole |
| 3,608,095 A | 9/1971 | Barry |
| 3,638,654 A | 2/1972 | Akuba |
| 3,656,185 A | 4/1972 | Carpentier |
| RE27,391 E | 6/1972 | Merser |
| 3,753,438 A | 8/1973 | Wood et al. |
| 3,776,237 A | 12/1973 | Hill et al. |
| 3,802,438 A | 4/1974 | Wolvek |
| 3,825,009 A | 7/1974 | Williams |
| 3,837,345 A | 9/1974 | Matar |
| 3,874,388 A | 4/1975 | King et al. |
| 3,875,648 A | 4/1975 | Bone |
| 3,905,403 A | 9/1975 | Smith et al. |
| 3,908,662 A | 9/1975 | Razqulov et al. |
| 3,910,281 A | 10/1975 | Kletschka et al. |
| 3,958,576 A | 5/1976 | Komiya |
| 3,976,079 A | 8/1976 | Samuels |
| 3,995,619 A | 12/1976 | Glatzer |
| 4,006,747 A | 2/1977 | Kronenthal et al. |
| 4,018,228 A | 4/1977 | Goosen |
| 4,038,725 A | 8/1977 | Keefe |
| 4,042,979 A | 8/1977 | Angell |
| 4,073,179 A | 2/1978 | Hickey et al. |
| 4,103,690 A | 8/1978 | Harris |
| 4,111,206 A | 9/1978 | Vishnevsky et al. |
| 4,129,059 A | 12/1978 | Van Eck |
| 4,140,125 A | 2/1979 | Smith |
| 4,170,990 A | 10/1979 | Baumgart et al. |
| 4,185,636 A | 1/1980 | Gabbay et al. |
| 4,192,315 A | 3/1980 | Hilzinger et al. |
| 4,214,587 A | 7/1980 | Sakura |
| 4,217,902 A | 8/1980 | March |
| 4,243,048 A | 1/1981 | Griffin |
| 4,324,248 A | 4/1982 | Perlin |
| 4,345,601 A | 8/1982 | Fukuda |
| 4,352,358 A | 10/1982 | Angelchik |
| 4,366,819 A | 1/1983 | Kaster |
| 4,396,139 A | 8/1983 | Hall et al. |
| 4,416,266 A | 11/1983 | Baucom |
| 4,456,017 A | 6/1984 | Miles |
| 4,465,071 A | 8/1984 | Samuels et al. |
| 4,470,415 A | 9/1984 | Wozniak |
| 4,470,533 A | 9/1984 | Schuler |
| 4,474,181 A | 10/1984 | Schenck |
| 4,485,816 A | 12/1984 | Krumme |
| 4,492,229 A | 1/1985 | Grunwald |
| 4,522,207 A | 6/1985 | Kleiman et al. |
| 4,523,592 A | 6/1985 | Daniel |
| 4,532,927 A | 8/1985 | Miksza |
| 4,535,764 A | 8/1985 | Ebert |
| 4,549,545 A | 10/1985 | Levy |
| 4,553,542 A | 11/1985 | Schenck et al. |
| 4,576,605 A | 3/1986 | Kaidash et al. |
| 4,586,502 A | 5/1986 | Bedi et al. |
| 4,586,503 A | 5/1986 | Kirsch et al. |
| 4,593,693 A | 6/1986 | Schenck |
| 4,595,007 A | 6/1986 | Mericle |
| 4,612,932 A | 9/1986 | Caspar et al. |
| 4,622,970 A | 11/1986 | Wozniak |
| 4,624,255 A | 11/1986 | Schenck et al. |
| 4,637,380 A | 1/1987 | Orejola |
| 4,641,652 A | 2/1987 | Hutterer et al. |
| 4,665,906 A | 5/1987 | Jervis |
| 4,665,917 A | 5/1987 | Clanton et al. |
| 4,683,895 A | 8/1987 | Pohndorf |
| 4,706,362 A | 11/1987 | Strausburg |
| 4,719,917 A | 1/1988 | Barrows et al. |
| 4,719,924 A | 1/1988 | Crittenden et al. |
| 4,730,615 A | 3/1988 | Sutherland et al. |
| 4,732,151 A | 3/1988 | Jones |
| 4,809,695 A | 3/1989 | Gwathmey et al. |
| 4,820,298 A | 4/1989 | Leveen et al. |
| 4,844,318 A | 7/1989 | Kunreuther |
| 4,873,975 A | 10/1989 | Walsh et al. |
| 4,890,615 A | 1/1990 | Caspari et al. |
| 4,896,668 A | 1/1990 | Popoff et al. |
| 4,899,744 A | 2/1990 | Fujitsuka et al. |
| 4,901,721 A | 2/1990 | Hakki |
| 4,923,461 A | 5/1990 | Caspari et al. |
| 4,924,866 A | 5/1990 | Yoon |
| 4,926,860 A | 5/1990 | Stice et al. |
| 4,929,240 A | 5/1990 | Kirsch et al. |
| 4,930,674 A | 6/1990 | Barak |
| 4,932,955 A | 6/1990 | Merz et al. |
| 4,935,027 A | 6/1990 | Yoon |
| 4,950,015 A | 8/1990 | Nejib et al. |
| 4,950,283 A | 8/1990 | Dzubow et al. |
| 4,950,285 A | 8/1990 | Wilk |
| 4,957,498 A | 9/1990 | Caspari et al. |
| 4,983,176 A | 1/1991 | Cushman et al. |
| 4,990,152 A | 2/1991 | Yoon |
| 4,991,567 A | 2/1991 | McCuen et al. |
| 4,994,069 A | 2/1991 | Ritchart et al. |
| 4,997,439 A | 3/1991 | Chen |
| 5,002,550 A | 3/1991 | Li |
| 5,002,562 A | 3/1991 | Oberlander |
| 5,002,563 A * | 3/1991 | Pyka et al. .................. 606/222 |
| 5,007,920 A | 4/1991 | Torre |
| 5,011,481 A | 4/1991 | Myers et al. |
| 5,020,713 A | 6/1991 | Kunreuther |
| 5,026,379 A | 6/1991 | Yoon |
| 5,032,127 A | 7/1991 | Frazee et al. |
| 5,035,692 A | 7/1991 | Lyon et al. |
| 5,035,702 A | 7/1991 | Taheri |
| 5,042,707 A | 8/1991 | Taheri |
| 5,047,047 A | 9/1991 | Yoon |
| 5,053,047 A | 10/1991 | Yoon |
| 5,064,431 A | 11/1991 | Gilbertson et al. |
| 5,074,874 A | 12/1991 | Yoon et al. |
| 5,088,692 A | 2/1992 | Weiler |
| 5,100,418 A | 3/1992 | Yoon |
| 5,100,421 A | 3/1992 | Christoudias |
| 5,104,407 A | 4/1992 | Lam et al. |
| 5,119,983 A | 6/1992 | Green et al. |
| 5,123,913 A | 6/1992 | Wilk et al. |
| 5,127,413 A | 7/1992 | Ebert |
| 5,129,913 A | 7/1992 | Ruppert |
| 5,152,769 A | 10/1992 | Baber |
| 5,154,189 A | 10/1992 | Oberlander |
| 5,158,566 A | 10/1992 | Pianetti |
| 5,171,250 A | 12/1992 | Yoon |
| 5,171,252 A | 12/1992 | Friedland |
| 5,174,087 A | 12/1992 | Bruno |
| 5,178,634 A | 1/1993 | Ramos Martinez |
| 5,192,294 A | 3/1993 | Blake |
| 5,196,022 A | 3/1993 | Bilweis |
| 5,201,880 A | 4/1993 | Wright et al. |
| 5,207,694 A | 5/1993 | Broome |
| 5,217,027 A | 6/1993 | Hermens |
| 5,219,358 A | 6/1993 | Bendel et al. |
| 5,221,259 A | 6/1993 | Weldon et al. |
| 5,222,961 A | 6/1993 | Nakao et al. |
| 5,222,976 A | 6/1993 | Yoon |

| Patent No. | Date | Inventor |
|---|---|---|
| 5,234,447 A | 8/1993 | Kaster et al. |
| 5,236,440 A | 8/1993 | Hlavacek |
| 5,242,456 A | 9/1993 | Nash et al. |
| 5,242,457 A | 9/1993 | Akopov et al. |
| 5,246,443 A | 9/1993 | Mai |
| 5,250,053 A | 10/1993 | Snyder |
| 5,258,011 A | 11/1993 | Drews |
| 5,261,917 A | 11/1993 | Hasson et al. |
| 5,269,783 A | 12/1993 | Sander |
| 5,269,809 A | 12/1993 | Hayhurst et al. |
| 5,282,825 A | 2/1994 | Muck et al. |
| 5,290,289 A | 3/1994 | Sanders et al. |
| 5,304,117 A | 4/1994 | Wilk |
| 5,304,204 A | 4/1994 | Bregen |
| 5,306,296 A | 4/1994 | Wright et al. |
| 5,312,436 A | 5/1994 | Coffey et al. |
| 5,314,468 A | 5/1994 | Ramos Martinez |
| 5,330,503 A | 7/1994 | Yoon |
| 5,334,196 A | 8/1994 | Scott et al. |
| 5,336,233 A | 8/1994 | Chen |
| 5,336,239 A | 8/1994 | Gimpelson |
| 5,346,459 A | 9/1994 | Allen |
| 5,350,420 A | 9/1994 | Cosgrove et al. |
| 5,353,804 A | 10/1994 | Kornberg et al. |
| 5,355,897 A | 10/1994 | Pietrafitta et al. |
| 5,356,424 A | 10/1994 | Buzerak et al. |
| 5,364,406 A | 11/1994 | Sewell |
| 5,366,459 A | 11/1994 | Yoon |
| 5,366,462 A | 11/1994 | Kaster et al. |
| 5,366,479 A | 11/1994 | McGarry et al. |
| 5,374,268 A | 12/1994 | Sander |
| 5,376,096 A | 12/1994 | Foster |
| 5,382,259 A | 1/1995 | Phelps et al. |
| 5,383,904 A | 1/1995 | Totakura et al. |
| 5,387,227 A | 2/1995 | Grice |
| 5,403,331 A | 4/1995 | Chesterfield |
| 5,403,333 A | 4/1995 | Kaster et al. |
| 5,403,338 A | 4/1995 | Milo |
| 5,403,346 A | 4/1995 | Loeser |
| 5,413,584 A | 5/1995 | Schulze |
| 5,417,684 A | 5/1995 | Jackson et al. |
| 5,417,700 A | 5/1995 | Egan |
| 5,423,821 A | 6/1995 | Pasque |
| 5,431,666 A | 7/1995 | Sauer et al. |
| 5,437,680 A | 8/1995 | Yoon |
| 5,437,681 A | 8/1995 | Meade et al. |
| 5,437,685 A | 8/1995 | Blasnik |
| 5,439,479 A | 8/1995 | Schichman et al. |
| 5,445,167 A | 8/1995 | Yoon et al. |
| 5,445,644 A | 8/1995 | Pietrafitta et al. |
| 5,450,860 A | 9/1995 | O'Connor |
| 5,451,231 A | 9/1995 | Rabenau et al. |
| 5,452,733 A | 9/1995 | Sterman et al. |
| 5,454,834 A | 10/1995 | Boebel et al. |
| 5,456,246 A | 10/1995 | Schmiedling et al. |
| 5,462,561 A | 10/1995 | Voda |
| 5,474,557 A | 12/1995 | Mai |
| 5,480,405 A | 1/1996 | Yoon |
| 5,486,187 A | 1/1996 | Schenck |
| 5,486,197 A | 1/1996 | Le et al. |
| 5,488,958 A | 2/1996 | Topel et al. |
| 5,496,334 A | 3/1996 | Klundt et al. |
| 5,499,990 A | 3/1996 | Schulken et al. |
| 5,500,000 A | 3/1996 | Feagin et al. |
| 5,522,884 A | 6/1996 | Wright |
| 5,527,342 A | 6/1996 | Pietrzak et al. |
| 5,533,236 A | 7/1996 | Tseng |
| 5,538,509 A | 7/1996 | Dunlap et al. |
| 5,545,214 A | 8/1996 | Stevens |
| 5,549,619 A | 8/1996 | Peters et al. |
| 5,556,411 A | 9/1996 | Taoda et al. |
| 5,562,685 A | 10/1996 | Mollenauer et al. |
| 5,569,205 A | 10/1996 | Hart et al. |
| 5,569,274 A | 10/1996 | Rapacki et al. |
| 5,569,301 A | 10/1996 | Granger et al. |
| 5,571,119 A | 11/1996 | Atala |
| 5,571,175 A | 11/1996 | Vanney et al. |
| 5,582,616 A | 12/1996 | Bolduc et al. |
| 5,582,619 A | 12/1996 | Ken |
| 5,584,879 A | 12/1996 | Reimold et al. |
| 5,586,983 A | 12/1996 | Sanders et al. |
| 5,591,179 A | 1/1997 | Edelstein |
| 5,593,414 A | 1/1997 | Shipp et al. |
| 5,593,424 A | 1/1997 | Northrup, III |
| 5,597,378 A | 1/1997 | Jervis |
| 5,601,571 A | 2/1997 | Moss |
| 5,601,572 A | 2/1997 | Middleman et al. |
| 5,601,600 A | 2/1997 | Ton |
| 5,603,718 A | 2/1997 | Xu |
| 5,609,608 A | 3/1997 | Bennett et al. |
| 5,628,757 A | 5/1997 | Hasson |
| 5,630,540 A | 5/1997 | Blewett |
| 5,632,752 A | 5/1997 | Buelna |
| 5,632,753 A | 5/1997 | Loeser |
| 5,643,295 A | 7/1997 | Yoon |
| 5,643,305 A | 7/1997 | Al-Tameem |
| 5,645,568 A | 7/1997 | Chervitz et al. |
| 5,653,716 A | 8/1997 | Malo et al. |
| 5,653,718 A | 8/1997 | Yoon |
| 5,658,312 A | 8/1997 | Green et al. |
| 5,660,186 A | 8/1997 | Bachir |
| 5,665,109 A | 9/1997 | Yoon |
| 5,669,918 A | 9/1997 | Balazs et al. |
| 5,676,670 A | 10/1997 | Kim |
| 5,683,417 A | 11/1997 | Cooper |
| 5,690,662 A | 11/1997 | Chiu et al. |
| 5,695,504 A | 12/1997 | Gifford, III et al. |
| 5,695,505 A | 12/1997 | Yoon |
| 5,697,913 A | 12/1997 | Sierocuk et al. |
| 5,697,943 A | 12/1997 | Sauer et al. |
| 5,700,270 A | 12/1997 | Peyser et al. |
| 5,700,271 A | 12/1997 | Whitfield et al. |
| 5,702,412 A | 12/1997 | Popov et al. |
| 5,707,362 A | 1/1998 | Yoon |
| 5,707,380 A | 1/1998 | Hinchliffe et al. |
| 5,709,693 A | 1/1998 | Taylor |
| 5,709,695 A | 1/1998 | Northrup, III |
| 5,715,987 A | 2/1998 | Kelley et al. |
| 5,720,755 A | 2/1998 | Dakov |
| 5,725,539 A | 3/1998 | Matern |
| 5,725,542 A | 3/1998 | Yoon |
| 5,728,135 A | 3/1998 | Bregen et al. |
| 5,732,872 A | 3/1998 | Bolduc et al. |
| 5,735,290 A | 4/1998 | Sterman et al. |
| 5,746,753 A | 5/1998 | Sullivan et al. |
| 5,755,778 A | 5/1998 | Kleshinski |
| 5,766,189 A | 6/1998 | Matsumo |
| 5,769,870 A | 6/1998 | Salahich et al. |
| 5,779,718 A | 7/1998 | Green et al. |
| 5,782,397 A | 7/1998 | Koukline |
| 5,782,844 A | 7/1998 | Yoon et al. |
| 5,797,920 A | 8/1998 | Kim |
| 5,797,933 A | 8/1998 | Snow et al. |
| 5,797,934 A | 8/1998 | Rygaard |
| 5,797,960 A * | 8/1998 | Stevens et al. ............... 606/213 |
| 5,799,661 A | 9/1998 | Boyd et al. |
| 5,799,857 A | 9/1998 | Robertson et al. |
| 5,810,848 A | 9/1998 | Hayhurst |
| 5,810,851 A | 9/1998 | Yoon |
| 5,810,853 A | 9/1998 | Yoon |
| 5,810,882 A | 9/1998 | Bolduc et al. |
| 5,817,113 A | 10/1998 | Gifford, III et al. |
| 5,820,631 A | 10/1998 | Nobles |
| 5,824,002 A | 10/1998 | Gentelia et al. |
| 5,824,008 A | 10/1998 | Bolduc et al. |
| 5,827,265 A | 10/1998 | Glinsky et al. |
| 5,827,316 A | 10/1998 | Young et al. |
| 5,830,221 A | 11/1998 | Stein et al. |
| 5,830,222 A | 11/1998 | Makower |
| 5,833,698 A | 11/1998 | Hinchliffe et al. |
| 5,849,019 A | 12/1998 | Yoon |
| 5,851,216 A | 12/1998 | Allen |
| 5,855,614 A | 1/1999 | Stevens et al. |
| 5,868,702 A | 2/1999 | Stevens et al. |
| 5,868,763 A | 2/1999 | Spence et al. |
| 5,871,528 A | 2/1999 | Camps et al. |
| 5,879,371 A | 3/1999 | Gardiner et al. |
| 5,881,943 A | 3/1999 | Heck et al. |

| | | | |
|---|---|---|---|
| 5,882,340 A | 3/1999 | Yoon | |
| 5,891,130 A | 4/1999 | Palermo et al. | |
| 5,891,160 A | 4/1999 | Williamson, IV et al. | |
| 5,893,369 A | 4/1999 | LeMole | |
| 5,893,865 A | 4/1999 | Swindle et al. | |
| 5,893,886 A | 4/1999 | Zegdi et al. | |
| 5,895,394 A | 4/1999 | Kienzle et al. | |
| 5,904,697 A | 5/1999 | Gifford, III et al. | |
| 5,908,428 A | 6/1999 | Scirica et al. | |
| 5,911,352 A | 6/1999 | Racenet et al. | |
| 5,919,207 A | 7/1999 | Taheri | |
| 5,931,842 A | 8/1999 | Goldsteen et al. | |
| 5,941,434 A | 8/1999 | Green | |
| 5,941,442 A | 8/1999 | Geiste et al. | |
| 5,941,888 A | 8/1999 | Wallace et al. | |
| 5,941,908 A | 8/1999 | Goldsteen et al. | |
| 5,944,730 A | 8/1999 | Nobles et al. | |
| 5,951,576 A | 9/1999 | Wakabayashi | |
| 5,951,600 A | 9/1999 | Lemelson | |
| 5,954,732 A * | 9/1999 | Hart et al. | 606/144 |
| 5,954,735 A | 9/1999 | Rygaard | |
| 5,957,363 A | 9/1999 | Heck | |
| 5,957,938 A | 9/1999 | Zhu et al. | |
| 5,957,940 A | 9/1999 | Tanner et al. | |
| 5,961,481 A | 10/1999 | Sterman et al. | |
| 5,961,539 A | 10/1999 | Northrup, III et al. | |
| 5,964,772 A | 10/1999 | Bolduc et al. | |
| 5,964,782 A | 10/1999 | Lafontaine et al. | |
| 5,972,024 A | 10/1999 | Northrup, III et al. | |
| 5,976,159 A | 11/1999 | Bolduc et al. | |
| 5,976,161 A | 11/1999 | Kirsch et al. | |
| 5,976,164 A | 11/1999 | Bencini et al. | |
| 5,976,178 A | 11/1999 | Goldsteen et al. | |
| 5,984,917 A | 11/1999 | Fleischmann et al. | |
| 5,984,959 A | 11/1999 | Robertson et al. | |
| 5,989,242 A | 11/1999 | Saadat et al. | |
| 5,989,268 A | 11/1999 | Pugsley, Jr. et al. | |
| 5,989,276 A | 11/1999 | Houser et al. | |
| 5,989,278 A | 11/1999 | Mueller | |
| 5,993,468 A | 11/1999 | Rygaard | |
| 5,997,556 A | 12/1999 | Tanner | |
| 6,001,110 A | 12/1999 | Adams | |
| 6,007,544 A | 12/1999 | Kim | |
| 6,010,531 A | 1/2000 | Donlon et al. | |
| 6,013,084 A | 1/2000 | Ken et al. | |
| 6,022,367 A | 2/2000 | Sherts | |
| 6,024,748 A | 2/2000 | Manzo et al. | |
| 6,032,849 A | 3/2000 | Mastri et al. | |
| 6,033,419 A | 3/2000 | Hamblin, Jr. et al. | |
| 6,036,699 A | 3/2000 | Andreas et al. | |
| 6,036,703 A | 3/2000 | Evans et al. | |
| 6,036,710 A | 3/2000 | McGarry et al. | |
| 6,042,607 A | 3/2000 | Williamson et al. | |
| 6,056,751 A | 5/2000 | Fenton | |
| 6,063,070 A | 5/2000 | Eder | |
| 6,066,148 A | 5/2000 | Rygaard | |
| 6,074,401 A | 6/2000 | Gardiner et al. | |
| 6,074,418 A * | 6/2000 | Buchanan et al. | 623/2.11 |
| 6,077,291 A | 6/2000 | Das | |
| 6,080,114 A | 6/2000 | Russin | |
| 6,083,237 A | 7/2000 | Huitema et al. | |
| 6,106,538 A | 8/2000 | Shiber | |
| 6,110,188 A | 8/2000 | Narciso | |
| 6,113,611 A | 9/2000 | Allen et al. | |
| 6,113,612 A | 9/2000 | Swanson et al. | |
| 6,120,524 A | 9/2000 | Taheri | |
| 6,132,438 A | 10/2000 | Fleischmann et al. | |
| 6,139,540 A | 10/2000 | Rost et al. | |
| 6,143,004 A | 11/2000 | Davis et al. | |
| 6,149,658 A | 11/2000 | Gardiner et al. | |
| 6,152,935 A | 11/2000 | Kammerer et al. | |
| 6,152,937 A | 11/2000 | Peterson et al. | |
| 6,159,165 A | 12/2000 | Ferrera et al. | |
| 6,159,225 A | 12/2000 | Makower | |
| 6,165,183 A | 12/2000 | Kuehn et al. | |
| 6,165,185 A | 12/2000 | Shennib et al. | |
| 6,171,320 B1 | 1/2001 | Monassevitch | |
| 6,171,321 B1 | 1/2001 | Gifford, III et al. | |
| 6,176,413 B1 | 1/2001 | Heck et al. | |
| 6,176,864 B1 | 1/2001 | Chapman | |
| 6,179,840 B1 | 1/2001 | Bowman | |
| 6,179,848 B1 | 1/2001 | Solem | |
| 6,179,849 B1 | 1/2001 | Yencho et al. | |
| 6,183,512 B1 | 2/2001 | Howanec et al. | |
| 6,190,373 B1 | 2/2001 | Palermo et al. | |
| 6,193,733 B1 | 2/2001 | Adams | |
| 6,193,734 B1 | 2/2001 | Bolduc et al. | |
| 6,197,037 B1 | 3/2001 | Hair | |
| 6,217,611 B1 | 4/2001 | Klostermeyer | |
| 6,221,083 B1 | 4/2001 | Mayer | |
| 6,241,738 B1 | 6/2001 | Dereume | |
| 6,241,741 B1 | 6/2001 | Duhaylongsod et al. | |
| 6,248,117 B1 * | 6/2001 | Blatter | 606/153 |
| 6,250,308 B1 | 6/2001 | Cox | |
| 6,254,615 B1 | 7/2001 | Bolduc et al. | |
| 6,269,819 B1 | 8/2001 | Oz et al. | |
| 6,280,460 B1 | 8/2001 | Bolduc et al. | |
| 6,283,979 B1 | 9/2001 | Kelly et al. | |
| 6,283,993 B1 | 9/2001 | Cosgrove et al. | |
| 6,296,622 B1 | 10/2001 | Kurz et al. | |
| 6,296,656 B1 | 10/2001 | Bolduc et al. | |
| 6,306,141 B1 | 10/2001 | Jervis | |
| 6,332,893 B1 | 12/2001 | Mortier et al. | |
| 6,346,074 B1 | 2/2002 | Roth | |
| 6,346,112 B2 | 2/2002 | Adams | |
| 6,350,269 B1 | 2/2002 | Shipp et al. | |
| 6,352,543 B1 | 3/2002 | Cole | |
| 6,358,258 B1 * | 3/2002 | Arcia et al. | 606/139 |
| 6,361,559 B1 | 3/2002 | Houser et al. | |
| 6,368,348 B1 | 4/2002 | Gabbay | |
| 6,371,964 B1 | 4/2002 | Vargas et al. | |
| 6,387,105 B1 | 5/2002 | Gifford, III et al. | |
| 6,391,038 B2 | 5/2002 | Vargas et al. | |
| 6,402,764 B1 | 6/2002 | Hendricksen et al. | |
| 6,406,492 B1 | 6/2002 | Lytle | |
| 6,406,493 B1 | 6/2002 | Tu et al. | |
| 6,409,739 B1 | 6/2002 | Nobles et al. | |
| 6,409,758 B2 | 6/2002 | Stobie et al. | |
| 6,416,527 B1 | 7/2002 | Berg et al. | |
| 6,418,597 B1 | 7/2002 | Deschenes et al. | |
| 6,419,658 B1 | 7/2002 | Restelli et al. | |
| 6,419,681 B1 | 7/2002 | Vargas et al. | |
| 6,419,695 B1 | 7/2002 | Gabbay | |
| 6,425,900 B1 | 7/2002 | Knodel et al. | |
| 6,428,550 B1 | 8/2002 | Vargas et al. | |
| 6,428,555 B1 | 8/2002 | Koster, Jr. | |
| 6,451,048 B1 | 9/2002 | Berg et al. | |
| 6,461,320 B1 | 10/2002 | Yencho et al. | |
| 6,475,222 B1 | 11/2002 | Berg et al. | |
| 6,478,804 B2 | 11/2002 | Vargas et al. | |
| 6,485,496 B1 | 11/2002 | Suyker et al. | |
| 6,491,707 B2 | 12/2002 | Makower et al. | |
| 6,497,671 B2 | 12/2002 | Ferrera et al. | |
| 6,497,710 B2 | 12/2002 | Yencho et al. | |
| 6,514,265 B2 | 2/2003 | Ho et al. | |
| 6,517,558 B2 | 2/2003 | Gittings et al. | |
| 6,524,338 B1 | 2/2003 | Gundry | |
| 6,533,812 B2 | 3/2003 | Swanson et al. | |
| 6,537,288 B2 | 3/2003 | Vargas et al. | |
| 6,547,799 B2 | 4/2003 | Hess et al. | |
| 6,551,332 B1 | 4/2003 | Nguyen et al. | |
| 6,562,053 B2 | 5/2003 | Schulze et al. | |
| 6,575,985 B2 | 6/2003 | Knight et al. | |
| 6,589,255 B2 | 7/2003 | Schulze et al. | |
| 6,607,541 B1 | 8/2003 | Gardiner et al. | |
| 6,607,542 B1 | 8/2003 | Wild et al. | |
| 6,613,059 B2 | 9/2003 | Schaller et al. | |
| 6,629,988 B2 | 10/2003 | Weadock | |
| 6,635,214 B2 | 10/2003 | Rapacki et al. | |
| 6,641,593 B1 | 11/2003 | Schaller et al. | |
| 6,648,900 B2 | 11/2003 | Fleischman et al. | |
| 6,651,670 B2 | 11/2003 | Rapacki et al. | |
| 6,651,672 B2 * | 11/2003 | Roth | 128/898 |
| 6,652,540 B1 | 11/2003 | Cole et al. | |
| 6,652,541 B1 | 11/2003 | Vargas et al. | |
| 6,660,015 B1 | 12/2003 | Berg et al. | |
| 6,682,540 B1 | 1/2004 | Sancoff et al. | |
| 6,695,859 B1 | 2/2004 | Golden et al. | |

| | | | | | |
|---|---|---|---|---|---|
| 6,702,826 B2 | 3/2004 | Liddicoat et al. | DE | 3203410 | 5/1981 |
| 6,709,442 B2 * | 3/2004 | Miller et al. ............... 606/153 | DE | 3227984 | 2/1984 |
| 6,712,829 B2 | 3/2004 | Schulze | DE | 3504202 | 8/1985 |
| 6,719,768 B1 | 4/2004 | Cole et al. | DE | 4133800 | 10/1991 |
| 6,743,243 B1 | 6/2004 | Roy et al. | DE | 4402058 | 4/1995 |
| 6,749,622 B2 | 6/2004 | McGuckin et al. | DE | 19547617 | 9/1997 |
| 6,776,782 B2 | 8/2004 | Schulze | DE | 197 32 234 | 1/1999 |
| 6,776,784 B2 | 8/2004 | Ginn | DE | 19732234 | 1/1999 |
| 6,776,785 B1 | 8/2004 | Yencho et al. | EP | 0072232 | 2/1983 |
| 6,802,847 B1 | 10/2004 | Carson et al. | EP | 0122046 | 3/1983 |
| 6,821,286 B1 | 11/2004 | Carranza et al. | EP | 0129441 | 12/1984 |
| 6,869,444 B2 | 3/2005 | Gabbay | EP | 0130037 | 1/1985 |
| 6,913,607 B2 | 7/2005 | Ainsworth et al. | EP | 0140557 | 5/1985 |
| 6,918,917 B1 | 7/2005 | Nguyen et al. | EP | 0121362 | 9/1987 |
| 6,921,407 B2 | 7/2005 | Nguyen et al. | EP | 0409569 | 1/1991 |
| 6,926,730 B1 | 8/2005 | Nguyen et al. | EP | 0432692 | 6/1991 |
| 6,945,980 B2 | 9/2005 | Nguyen et al. | EP | 0478949 | 8/1991 |
| 6,955,679 B1 | 10/2005 | Hendricksen et al. | EP | 0494636 | 7/1992 |
| 6,960,221 B2 | 11/2005 | Ho et al. | EP | 0537955 | 4/1993 |
| 6,979,337 B2 | 12/2005 | Kato | EP | 0559429 | 9/1993 |
| 6,979,338 B1 | 12/2005 | Loshakove et al. | EP | 0598529 | 5/1994 |
| 7,022,131 B1 | 4/2006 | Derowe et al. | EP | 0326426 | 12/1994 |
| 7,056,330 B2 | 6/2006 | Gayton | EP | 0419597 | 12/1994 |
| 7,063,711 B1 | 6/2006 | Loshakove et al. | EP | 0632999 | 1/1995 |
| 7,070,618 B2 | 7/2006 | Streeter | EP | 0641546 | 3/1995 |
| 7,182,769 B2 | 2/2007 | Ainsworth et al. | EP | 0656191 | 6/1995 |
| 7,220,268 B2 | 5/2007 | Blatter | EP | 0687446 | 12/1995 |
| 7,335,212 B2 * | 2/2008 | Edoga et al. ............... 606/139 | EP | 0705568 | 4/1996 |
| 2001/0018592 A1 | 8/2001 | Schaller et al. | EP | 0711532 | 5/1996 |
| 2001/0018593 A1 | 8/2001 | Nguyen et al. | EP | 0705569 | 10/1996 |
| 2001/0018611 A1 | 8/2001 | Solem et al. | EP | 0734697 | 10/1996 |
| 2001/0021856 A1 | 9/2001 | Bolduc et al. | EP | 0778005 | 6/1997 |
| 2001/0047181 A1 | 11/2001 | Ho et al. | EP | 0815795 | 1/1998 |
| 2002/0010490 A1 | 1/2002 | Schaller et al. | GB | 2223410 | 4/1990 |
| 2002/0042623 A1 | 4/2002 | Blatter et al. | JP | 07308322 | 11/1995 |
| 2002/0082614 A1 | 6/2002 | Logan et al. | JP | 08336544 | 12/1996 |
| 2002/0099395 A1 | 7/2002 | Acampora et al. | JP | 10337291 | 12/1998 |
| 2002/0151916 A1 | 10/2002 | Muramatsu et al. | RU | 2110222 | 5/1998 |
| 2002/0165561 A1 | 11/2002 | Ainsworth et al. | SU | 577022 | 10/1977 |
| 2002/0173803 A1 | 11/2002 | Ainsworth et al. | SU | 1186199 | 10/1985 |
| 2003/0074012 A1 | 4/2003 | Nguyen et al. | SU | 1456109 | 2/1989 |
| 2003/0078603 A1 | 4/2003 | Schaller et al. | SU | 1560133 | 4/1990 |
| 2003/0083742 A1 | 5/2003 | Spence et al. | WO | 90/06725 | 6/1990 |
| 2003/0093118 A1 | 5/2003 | Ho et al. | WO | 90/09149 | 8/1990 |
| 2003/0125755 A1 | 7/2003 | Schaller et al. | WO | 90/14795 | 12/1990 |
| 2003/0191481 A1 | 10/2003 | Nguyen et al. | WO | 91/07916 | 6/1991 |
| 2003/0195531 A1 | 10/2003 | Gardiner et al. | WO | 91/08708 | 6/1991 |
| 2003/0199974 A1 | 10/2003 | Lee et al. | WO | 91/17712 | 11/1991 |
| 2004/0050393 A1 * | 3/2004 | Golden et al. ............... 128/898 | WO | 92/05828 | 4/1992 |
| 2004/0068276 A1 | 4/2004 | Golden et al. | WO | 92/12676 | 8/1992 |
| 2004/0102797 A1 | 5/2004 | Golden et al. | WO | WO 92/12676 | 8/1992 |
| 2004/0111099 A1 | 6/2004 | Nguyen et al. | WO | 92/22041 | 12/1992 |
| 2004/0138685 A1 | 7/2004 | Clague et al. | WO | 93/01750 | 2/1993 |
| 2004/0176663 A1 | 9/2004 | Edoga | WO | 94/15535 | 7/1994 |
| 2004/0193259 A1 | 9/2004 | Gabbay | WO | 94/15537 | 7/1994 |
| 2005/0004582 A1 | 1/2005 | Edoga | WO | 96/00035 | 1/1996 |
| 2005/0021054 A1 | 1/2005 | Ainsworth et al. | WO | 96/06565 | 3/1996 |
| 2005/0043749 A1 | 2/2005 | Breton et al. | WO | 96/38090 | 12/1996 |
| 2005/0065601 A1 | 3/2005 | Lee et al. | WO | 97/12555 | 4/1997 |
| 2005/0070924 A1 * | 3/2005 | Schaller et al. ............... 606/142 | WO | WO 97/12555 | 4/1997 |
| 2005/0075659 A1 | 4/2005 | Realyvasquez et al. | WO | 97/16122 | 5/1997 |
| 2005/0075667 A1 | 4/2005 | Schaller et al. | WO | WO 97/16122 | 5/1997 |
| 2005/0080454 A1 | 4/2005 | Drews | WO | 97/27898 | 8/1997 |
| 2005/0101975 A1 | 5/2005 | Nguyen et al. | WO | 97/28744 | 8/1997 |
| 2005/0107871 A1 | 5/2005 | Realyvasquez et al. | WO | WO 97/27898 | 8/1997 |
| 2005/0131429 A1 | 6/2005 | Ho et al. | WO | 97/31575 | 9/1997 |
| 2005/0267572 A1 | 12/2005 | Schoon et al. | WO | 97/32526 | 9/1997 |
| 2006/0004389 A1 | 1/2006 | Nguyen et al. | WO | WO 97/31575 | 9/1997 |
| 2006/0253143 A1 | 11/2006 | Edoga | WO | 97/40754 | 11/1997 |
| 2006/0271081 A1 | 11/2006 | Realyvasquez | WO | 97/42881 | 11/1997 |
| 2006/0293701 A1 | 12/2006 | Ainsworth et al. | WO | WO 97/40754 | 11/1997 |
| 2007/0010835 A1 | 1/2007 | Breton et al. | WO | 98/19636 | 5/1998 |
| 2007/0027461 A1 | 2/2007 | Gardiner et al. | WO | WO 98/19636 | 5/1998 |
| 2007/0106313 A1 | 5/2007 | Golden et al. | WO | 98/30153 | 7/1998 |
| 2007/0142848 A1 | 6/2007 | Ainsworth et al. | WO | 98/42262 | 10/1998 |
| FOREIGN PATENT DOCUMENTS | | | WO | WO 98/42262 | 10/1998 |
| | | | WO | 98/48707 | 11/1998 |
| DE | 0377052 | 6/1923 | WO | 98/52475 | 11/1998 |
| DE | 2703529 | 1/1977 | WO | WO 98/48707 | 11/1998 |

| | | |
|---|---|---|
| WO | WO 98/52475 | 11/1998 |
| WO | 99/07294 | 2/1999 |
| WO | WO 99/07294 | 2/1999 |
| WO | 99/12484 | 3/1999 |
| WO | WO 99/12484 | 3/1999 |
| WO | 99/15088 | 4/1999 |
| WO | WO 99/15088 | 4/1999 |
| WO | 99/37218 | 7/1999 |
| WO | WO 99/37218 | 7/1999 |
| WO | 99/62406 | 12/1999 |
| WO | 99/62408 | 12/1999 |
| WO | 99/62409 | 12/1999 |
| WO | 99/62415 | 12/1999 |
| WO | 99/63910 | 12/1999 |
| WO | 99/65409 | 12/1999 |
| WO | WO 99/62408 | 12/1999 |
| WO | WO 99/62415 | 12/1999 |
| WO | WO 99/63910 | 12/1999 |
| WO | WO 99/65409 | 12/1999 |
| WO | 00/03759 | 1/2000 |
| WO | 00/15144 | 3/2000 |
| WO | WO 00/15144 | 3/2000 |
| WO | 00/59380 | 10/2000 |
| WO | 00/60995 | 10/2000 |
| WO | 00/64381 | 11/2000 |
| WO | 00/74603 | 12/2000 |
| WO | 01/19292 | 3/2001 |
| WO | 01/26557 | 4/2001 |
| WO | 01/26586 | 4/2001 |
| WO | 01/28432 | 4/2001 |
| WO | 01/54618 | 8/2001 |
| WO | 01/74254 | 10/2001 |
| WO | 02/13701 | 2/2002 |
| WO | 02/13702 | 2/2002 |
| WO | 02/30295 | 4/2002 |
| WO | 02/30298 | 4/2002 |
| WO | 02/34143 | 5/2002 |
| WO | 02/080779 | 10/2002 |
| WO | 02/080780 | 10/2002 |
| WO | 02/087425 | 11/2002 |
| WO | 03/053289 | 7/2003 |
| WO | 03/088875 | 10/2003 |
| WO | 2005/011468 | 2/2005 |
| WO | 2005/058170 | 6/2005 |

OTHER PUBLICATIONS

Chitwood Jr., Mitral Valve Repair: Ischemic, Mastery of Cardiothoracic Surgery, Lippencott-Raven Publishers, 1998, Chapter 32, pp. 309-321.

Emery, et al., Suture Techniques for MIDCAB Surgery, Techniques for Minimally Invasive Direct Coronary Artery Bypass (MIDCAB) Surgery, R.W. Emery ed., Hanley & Belfus, Inc.: Philadelphia, PA, Chapter 12, 1997, pp. 87-91.

Grondin, et al., Carpentier's Annulus and De Vega's Annuloplasty: The end of the tricuspid challenge, Nov. 1975, vol. 70, pp. 852-861.

Holper, et al., Surgery For Tricuspid Insufficiency: Long Term Follow-Up After De Vega Annuloplasty, Thorac Cardiovasc Surgeon, 41, 1993.

Maisano, et al., The Double Orifice Technique as a Standardized Approach to Treat Mitral Regurgitation Due to Severe Myxomatous Disease: Surgical Technique, European Journal of Cardiothoracic Surgery, vol. 17, 2000, 201-205.

Rabago, et al., The New De Vega Technique in Tricuspid Annuloplasty: Results in 150 patients, J. Cardiovas Surg. 1980, 21 pp. 231-238.

Rivera, et al., Carpentier's Flexible Ring Versus De Vega's Annuloplasty, J Thorac Cardiovas Surg, Feb. 1985, 89 pp. 196-203.

Wei, et al., De Vega's Semicircular Annuloplasty for Tricuspid Valve Regurgitation, Ann Thorac Surg, 1993, 55: pp. 482-485.

Wylie, et al., Manual of Vascular Surgery, R. H. Egdahl ed. Spring-Verlag: New York, vol. II, 1986, Table of Contents only.

Wylie, et al., Manual of Vascular Surgery, Springer-Verlag New York, vol. I, 1980, Table of Contents only.

Yun, et al. Mitral Valve Replacement, Mastery of Cardiothoracic Surgery, Lippencott-Raven Publishers, 1998, Chapter 34, pp. 329-341.

Yun, et al. Mitral Valve Replacement, Mastery of Cardiothoracic Surgery, Lippencott-Raven Publishers, pp. 329-341.

International Search Report PCT/US98/00462.
International Search Report PCT/US98/00795.
International Search Report PCT/US98/14211.
International Search Report PCT/US99/12563.
International Search Report PCT/US99/12566.
International Search Report PCT/US00/09092.
International Search Report PCT/US01/10501.
International Search Report PCT/US01/31709.
International Search Report PCT/US01/42653.
International Search Report PCT/US02/10865.
International Search Report PCT/US02/10866.
International Search Report PCT/US02/14261.
International Search Report PCT/US03/12073.
International Preliminary Examination Report PCT/US98/00462.
International Preliminary Examination Report PCT/US98/00795.
International Preliminary Examination Report PCT/US99/12566.
International Preliminary Examination Report PCT/US00/09092.
International Preliminary Examination Report PCT/US01/31709.
International Preliminary Examination Report PCT/US01/42653.
International Preliminary Examination Report PCT/US02/14261.
International Preliminary Examination Report PCT/US02/10865.
International Preliminary Examination Report PCT/US02/10866.
International Preliminary Examination Report PCT/US03/12073.
Written Opinion PCT/US99/12563.
Written Opinion PCT/US99/12566.
Written Opinion PCT/US00/09092.
Written Opinion PCT/US01/10501.
Written Opinion PCT/US01/31709.
Written Opinion PCT/US02/10866.
Written Opinion PCT/US02/14261.
Written Opinion PCT/US03/12073.
International Preliminary Report On Patentability PCT/US2004/023728.
US 6,503,260, 01/2003, Schaller et al. (withdrawn)

* cited by examiner

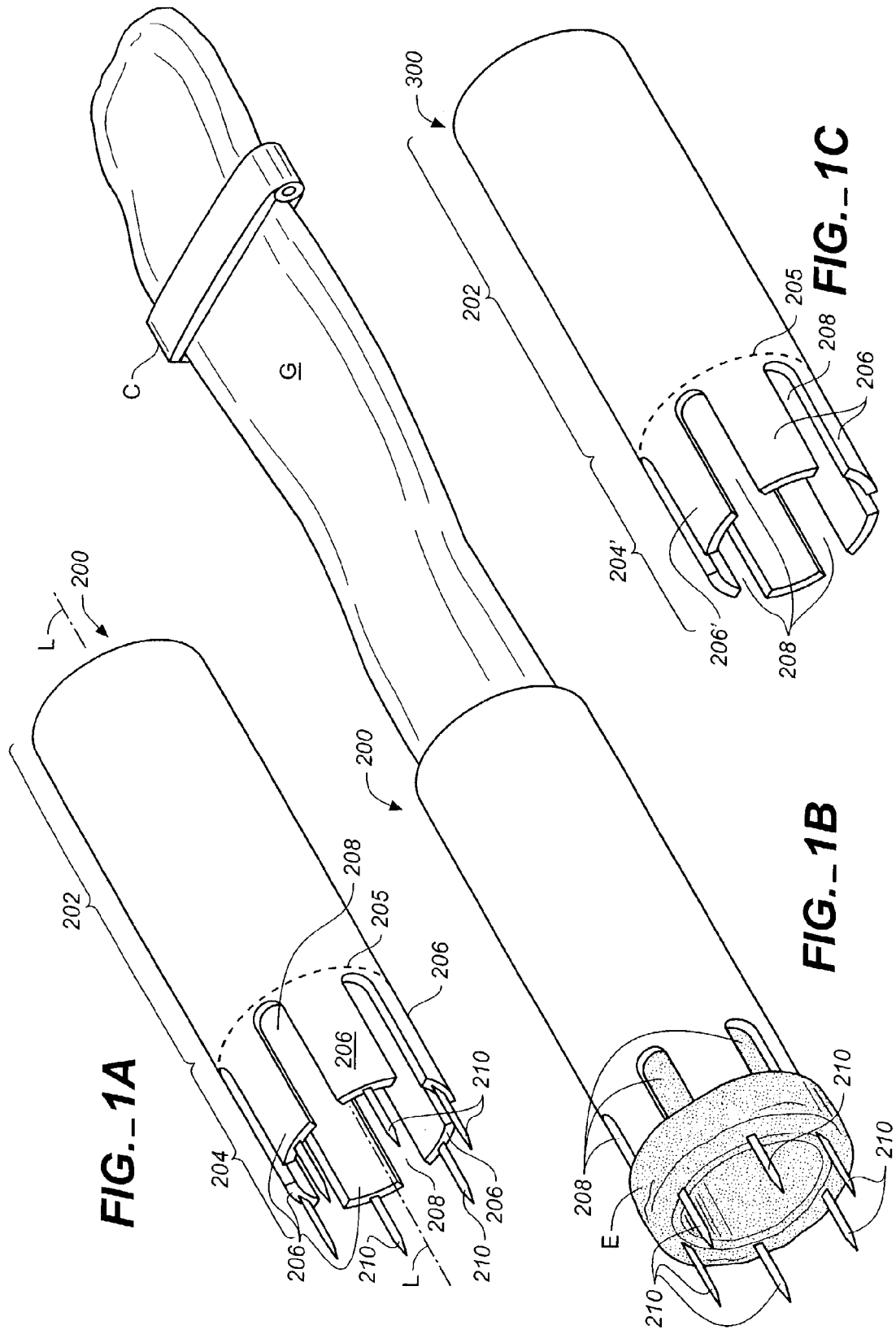

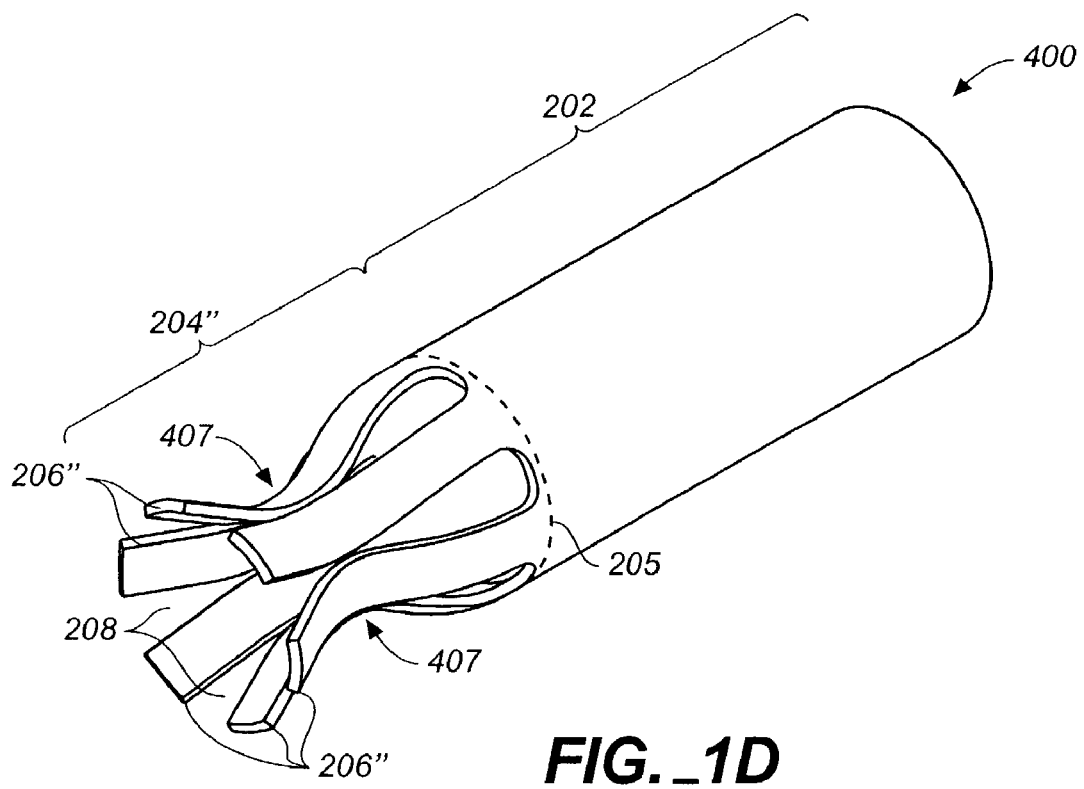
FIG._1D
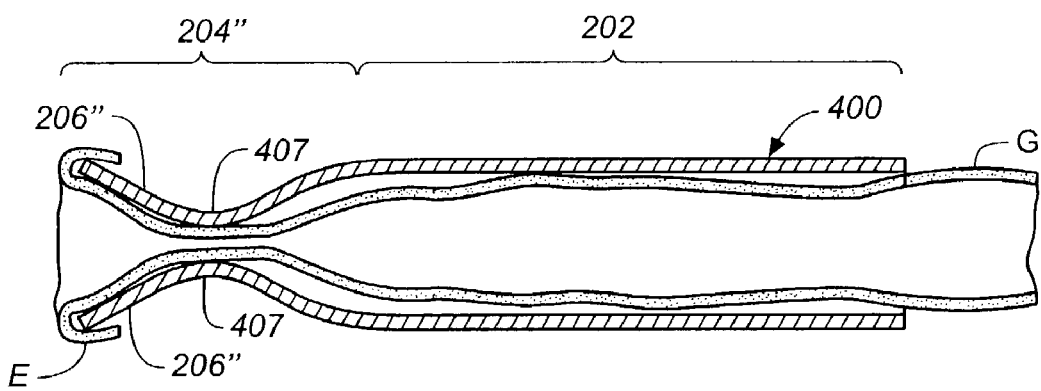
FIG._1E

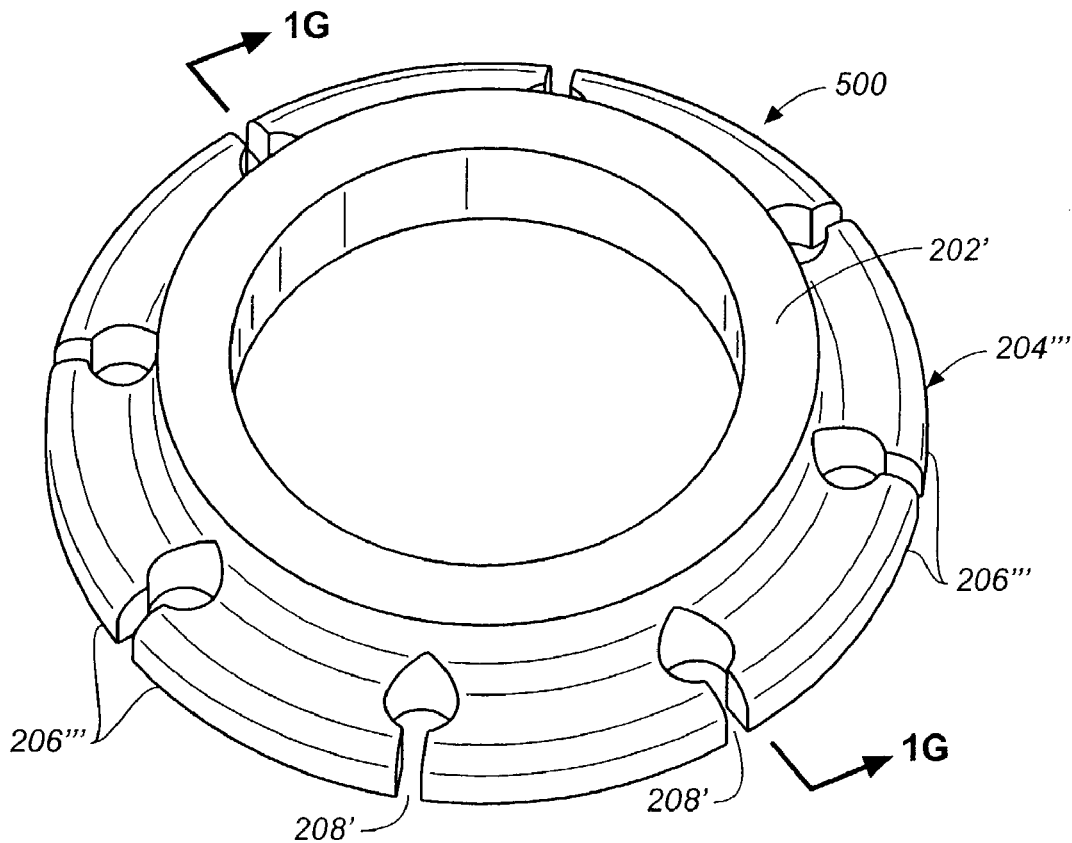
FIG._1F
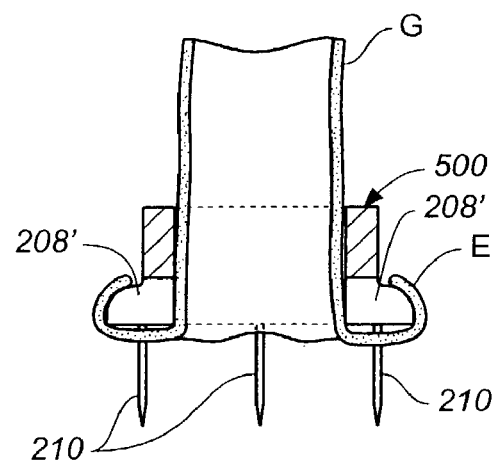
FIG._1G

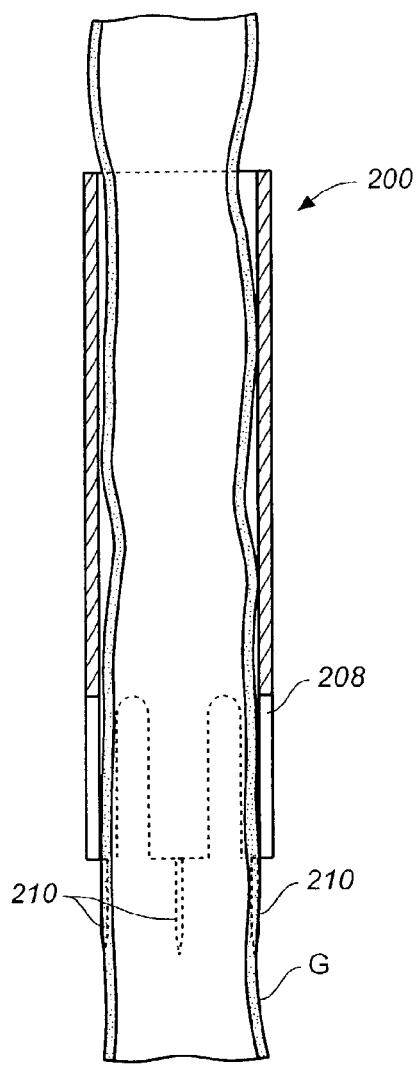
FIG._2A
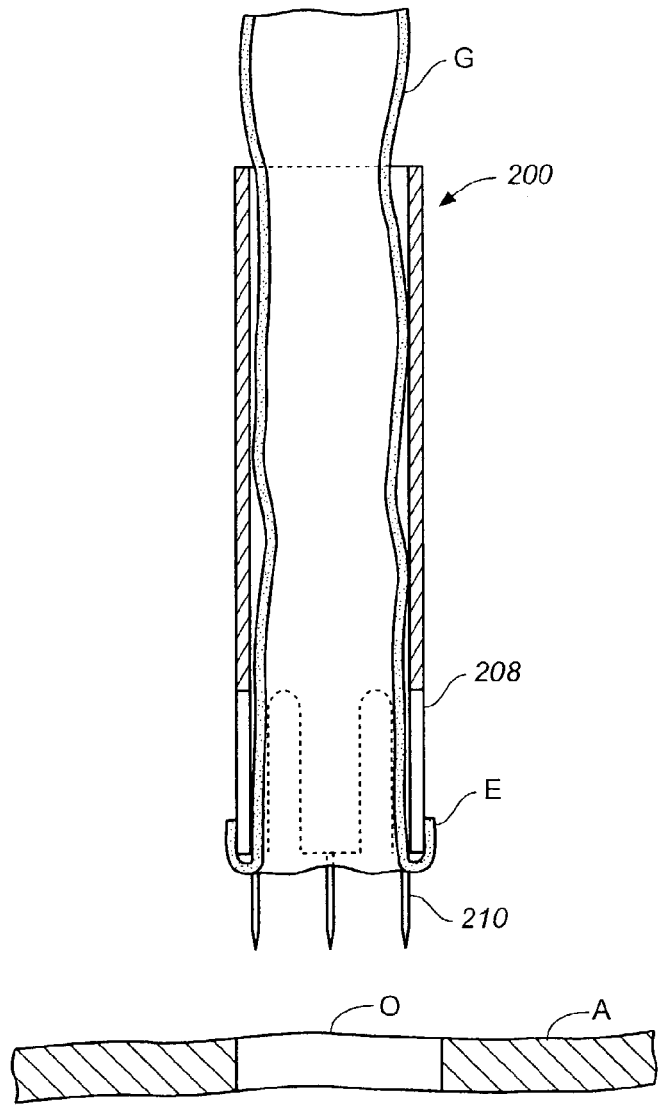
FIG._2B

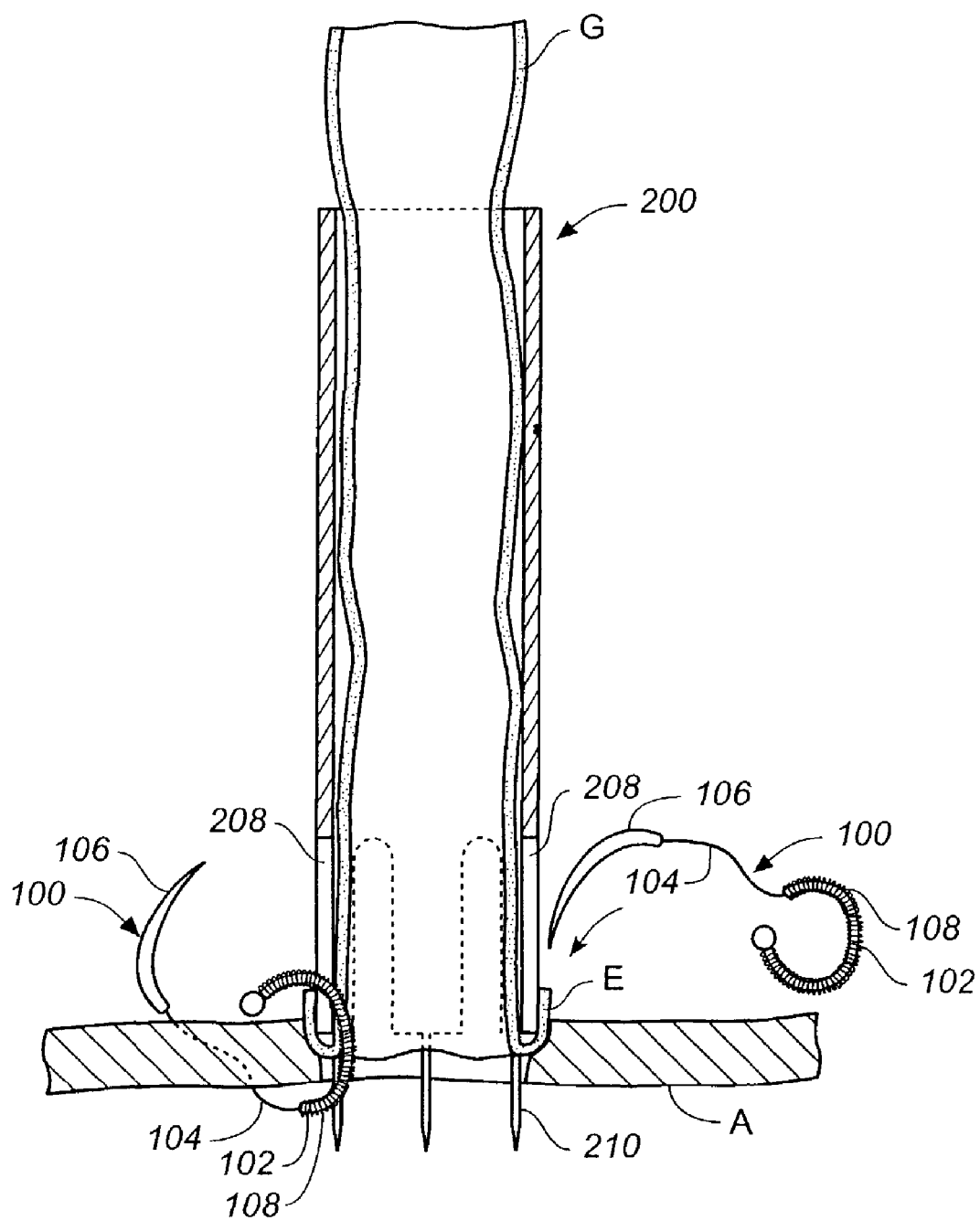
FIG._2C

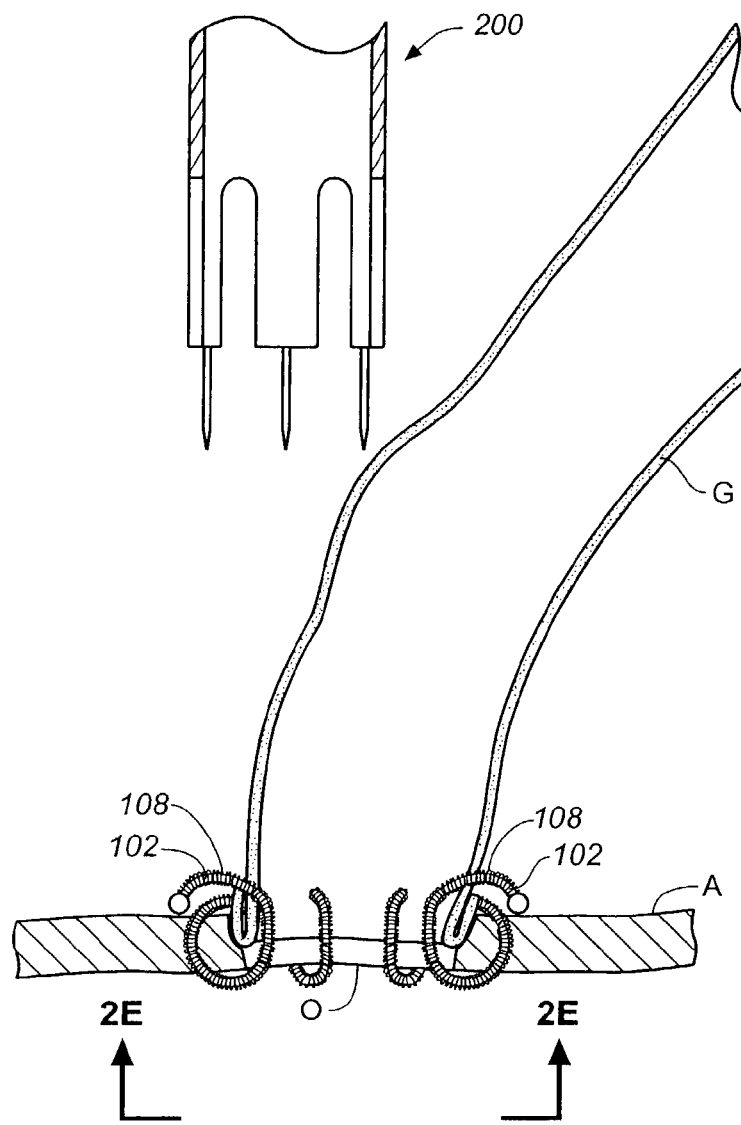
FIG._2D
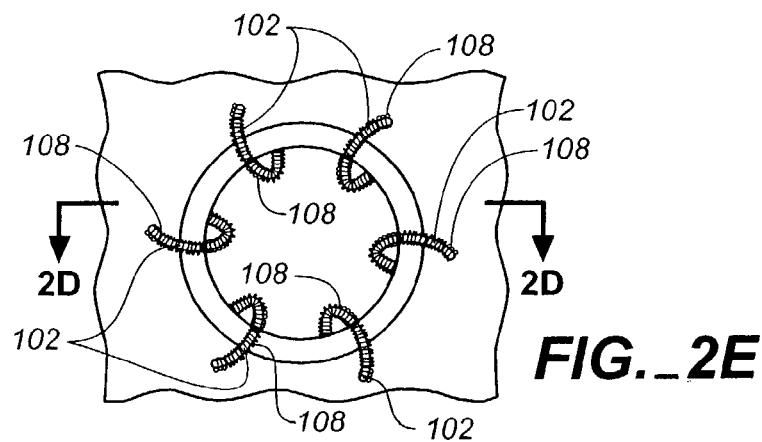
FIG._2E

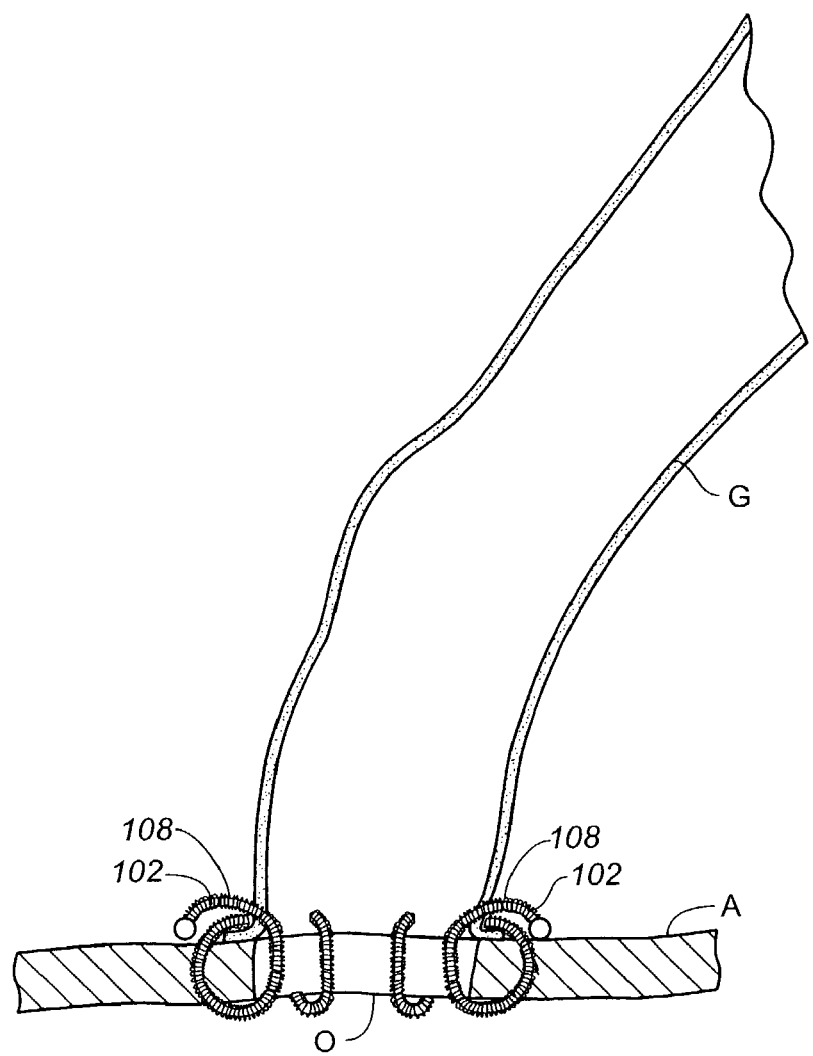
FIG._2F
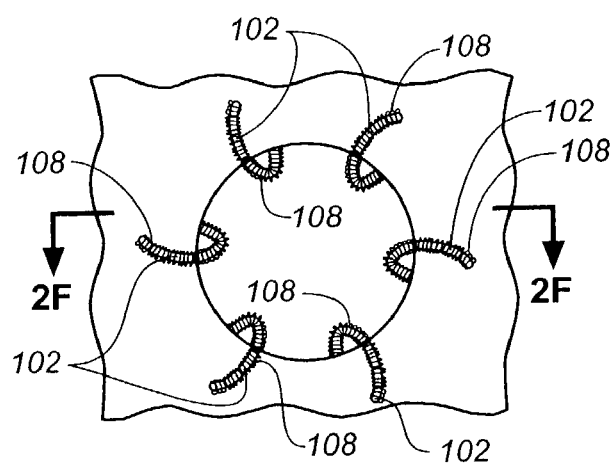
FIG._2G

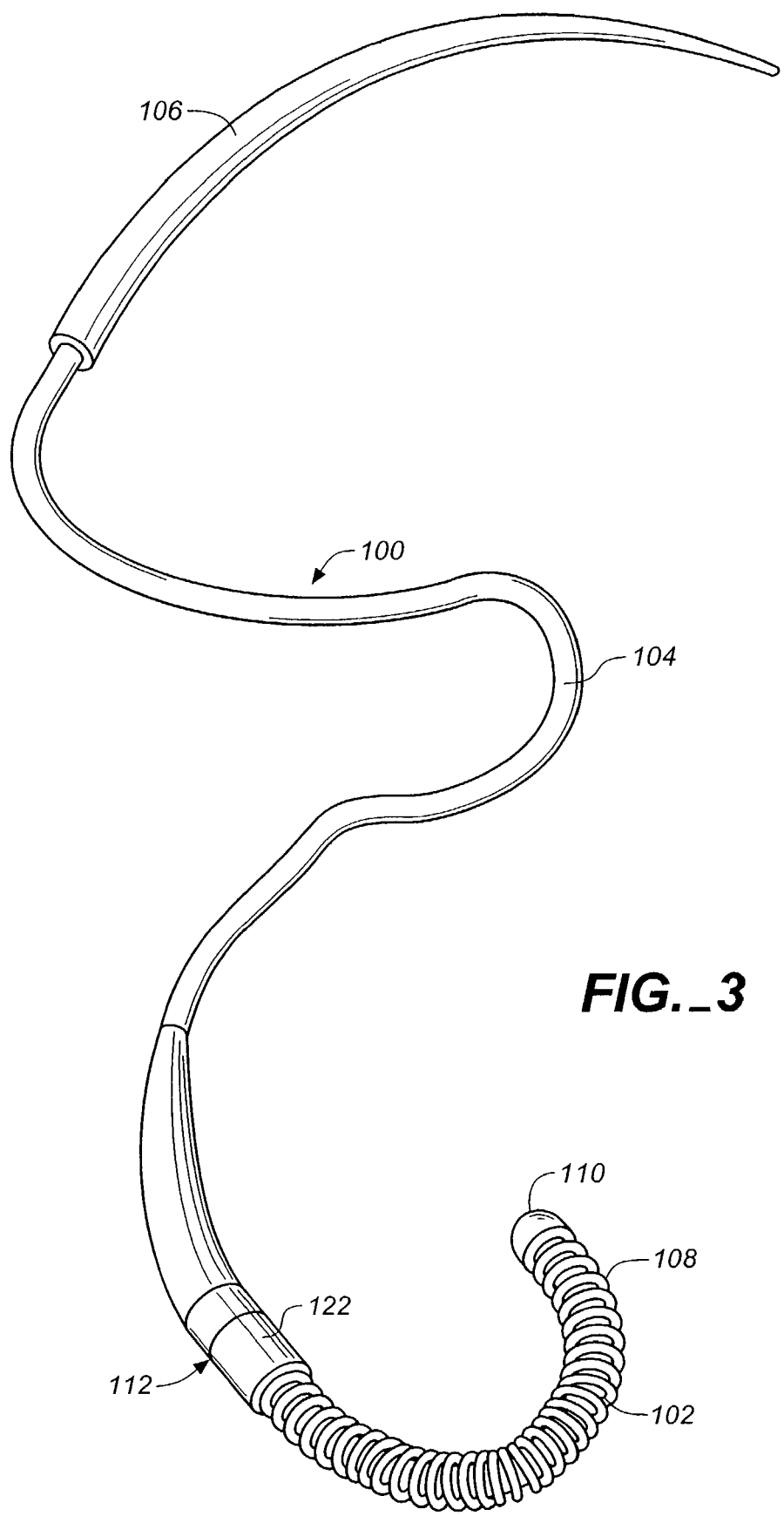
FIG._3

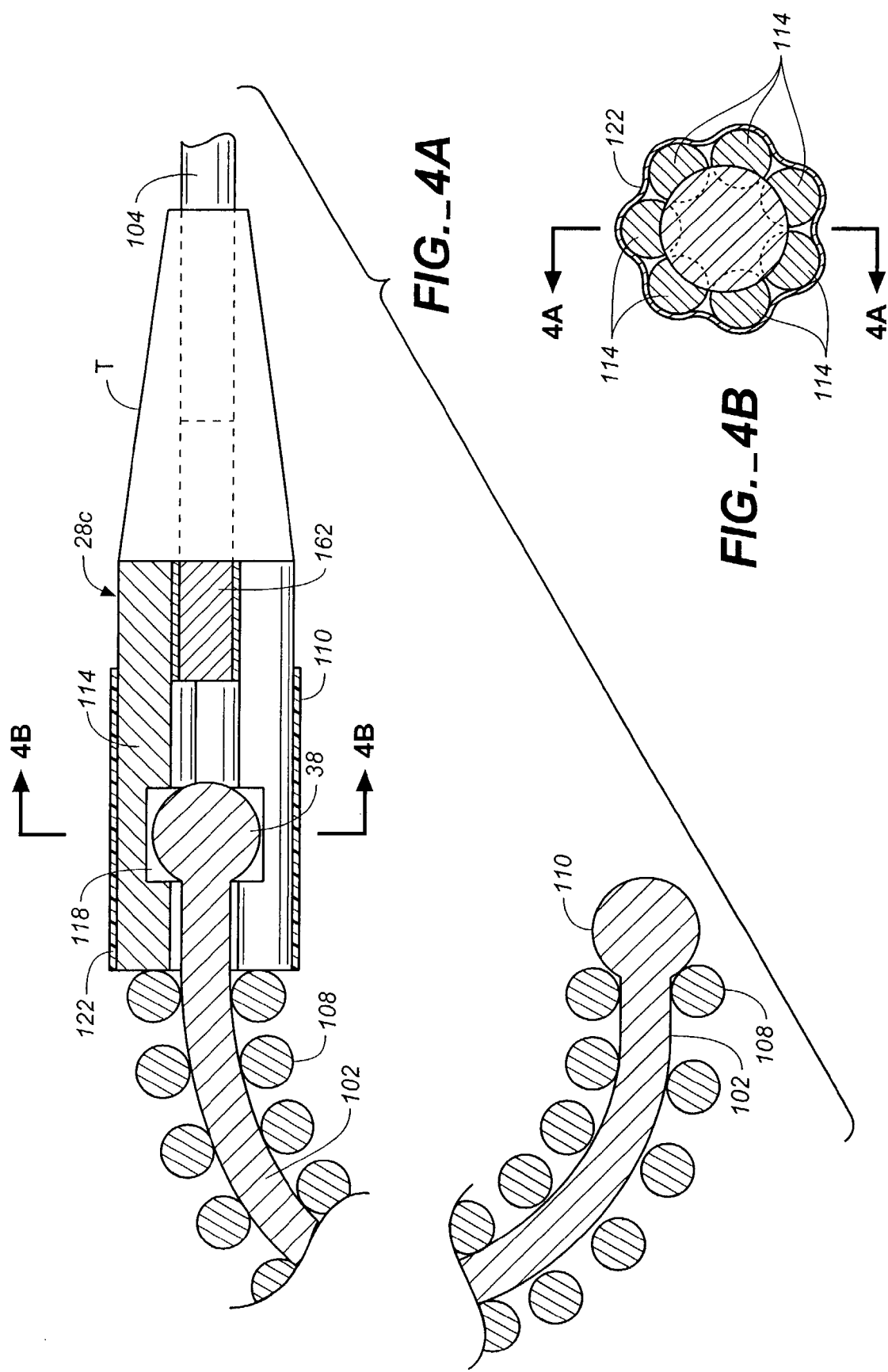

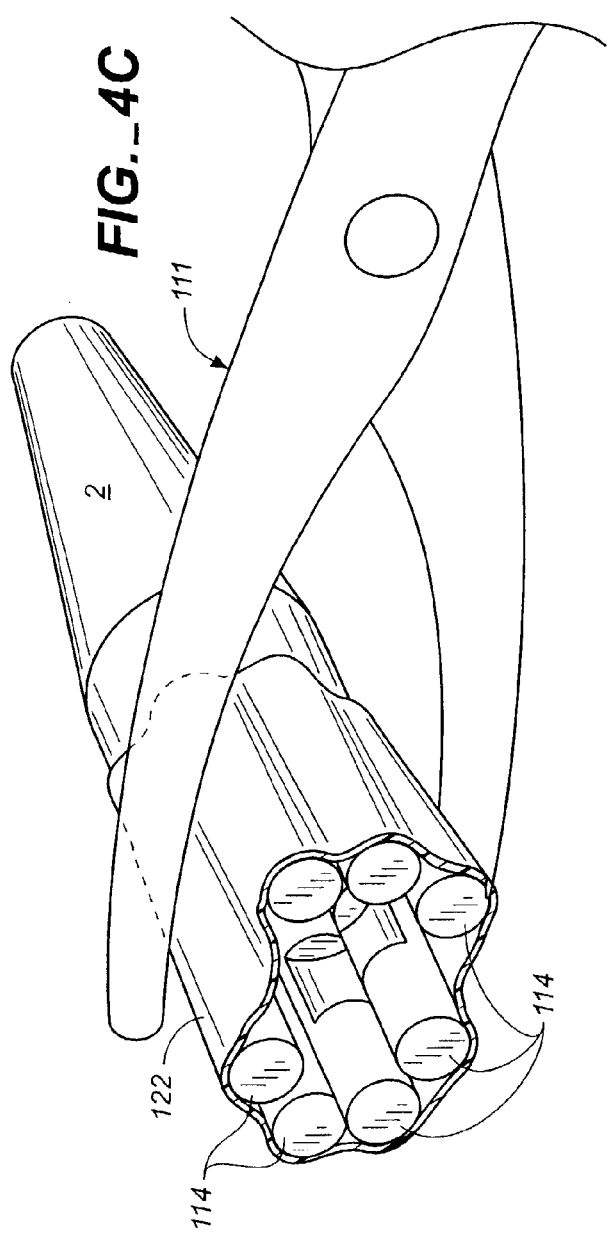
FIG._4C
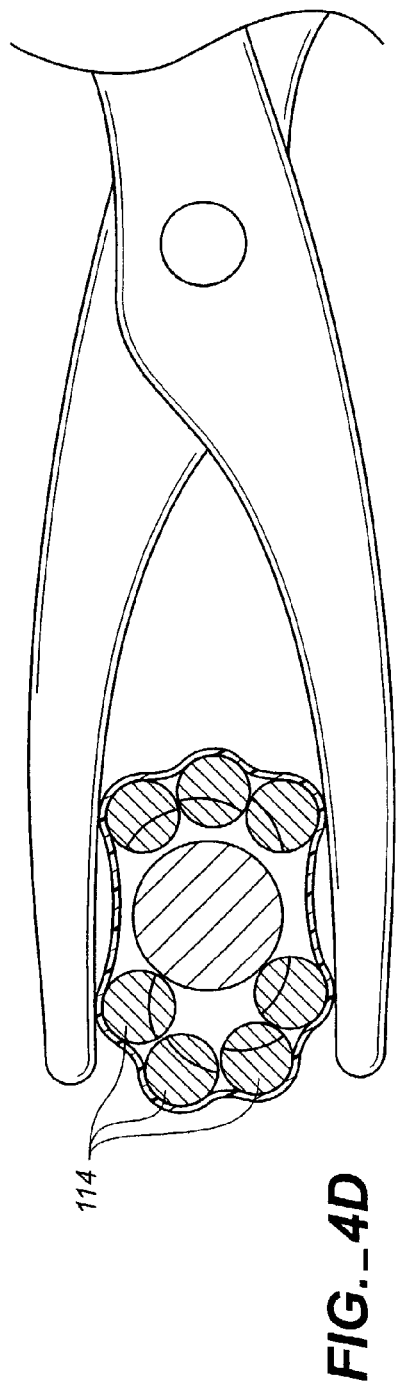
FIG._4D

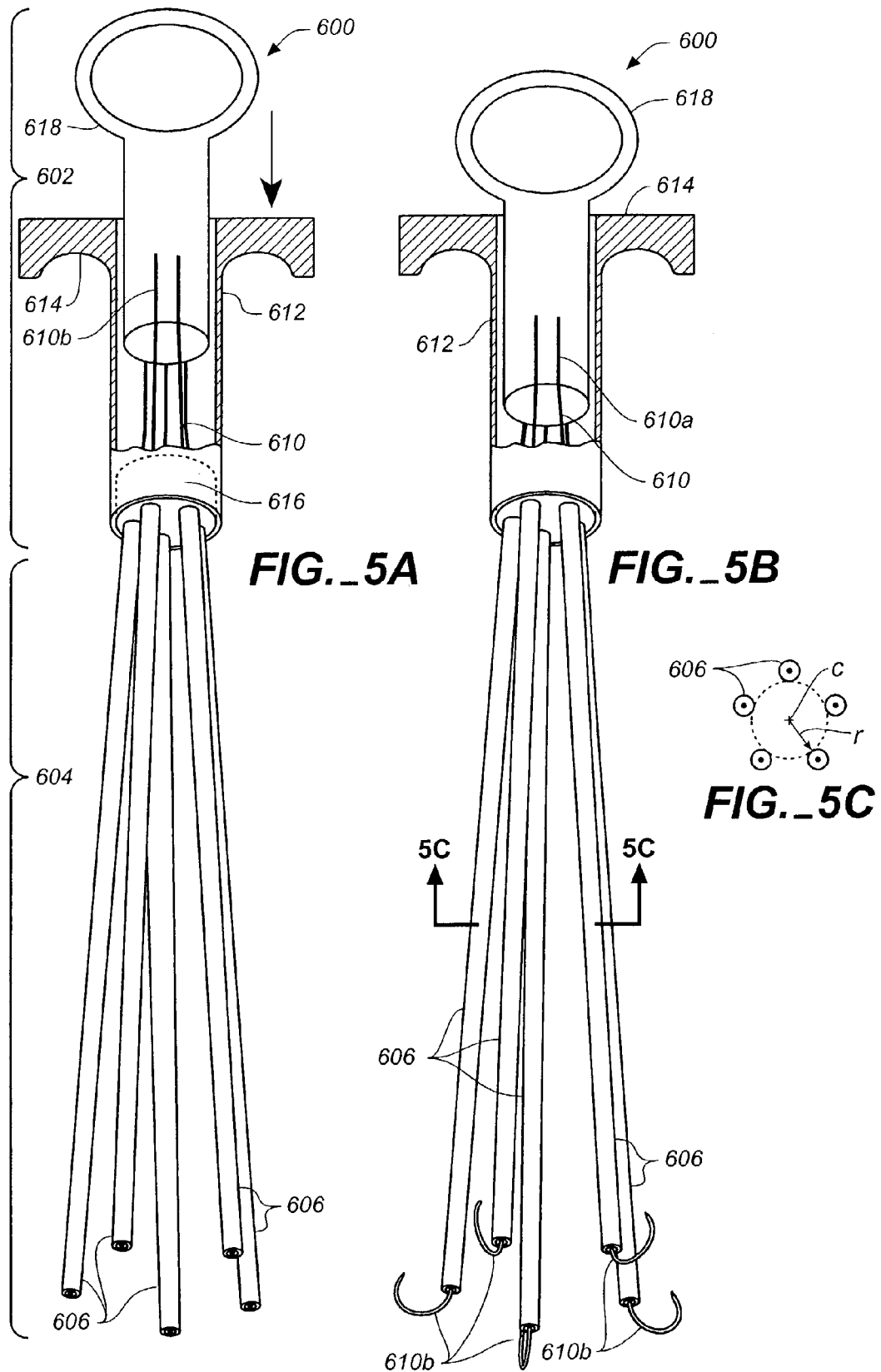

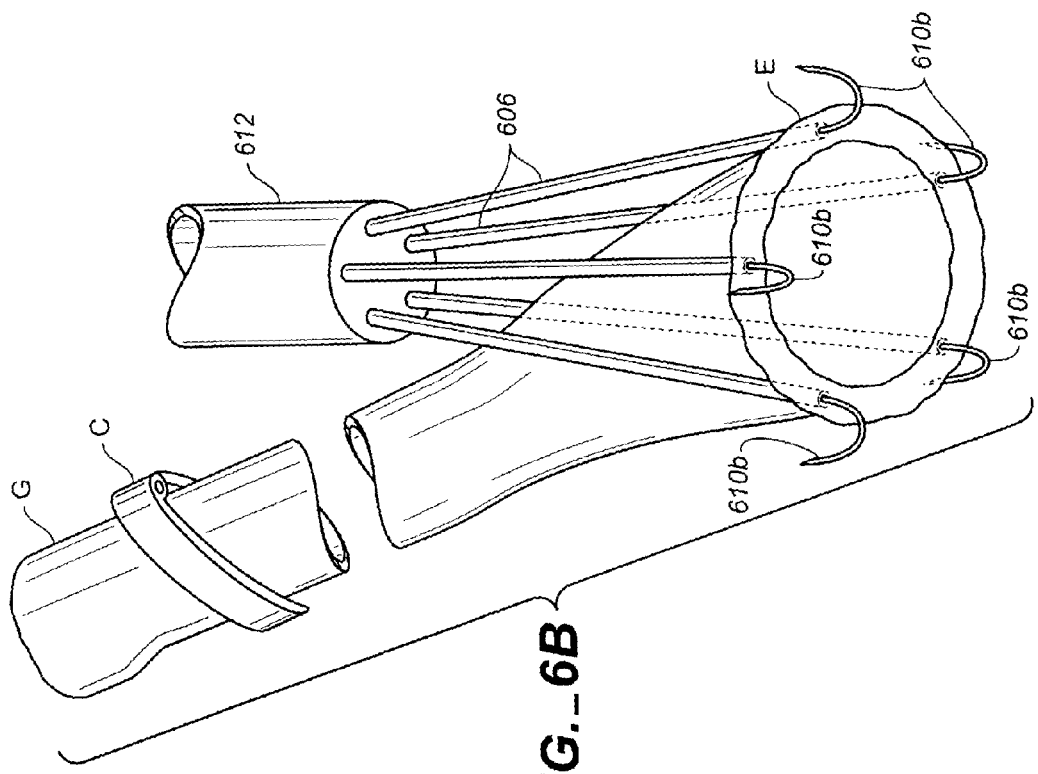
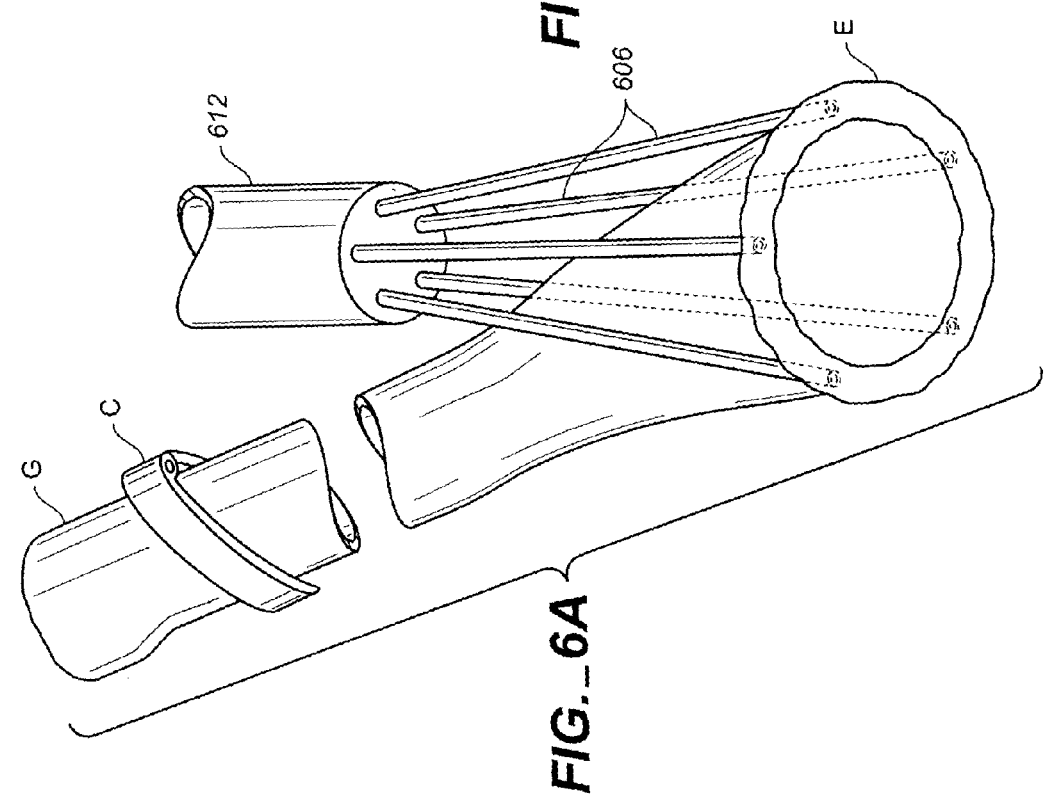

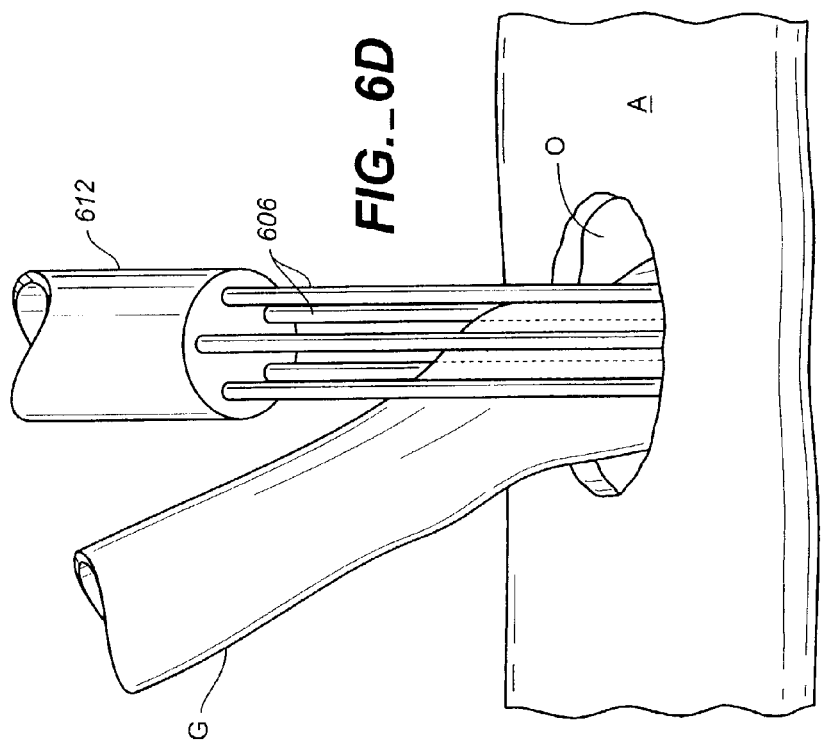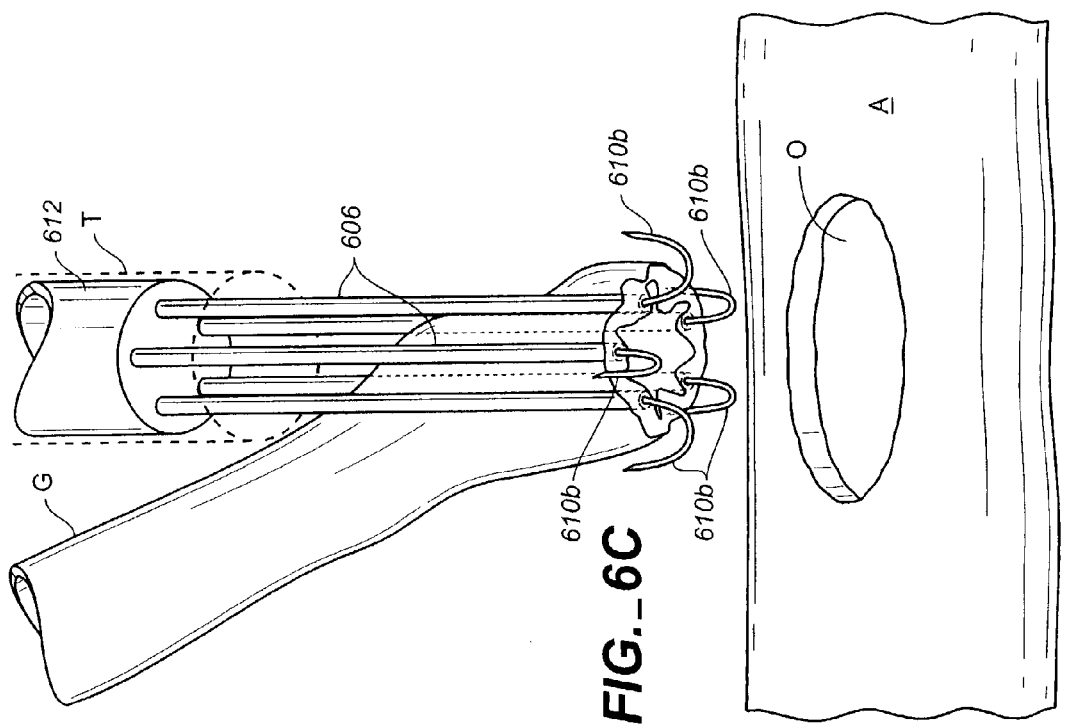

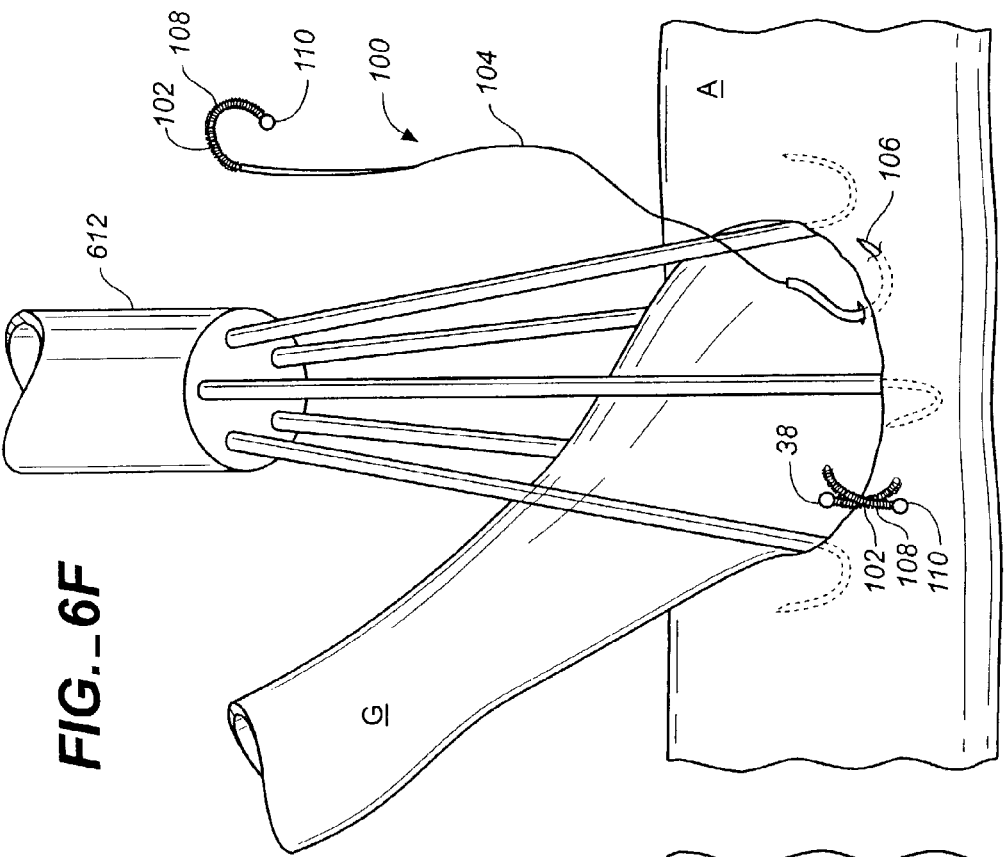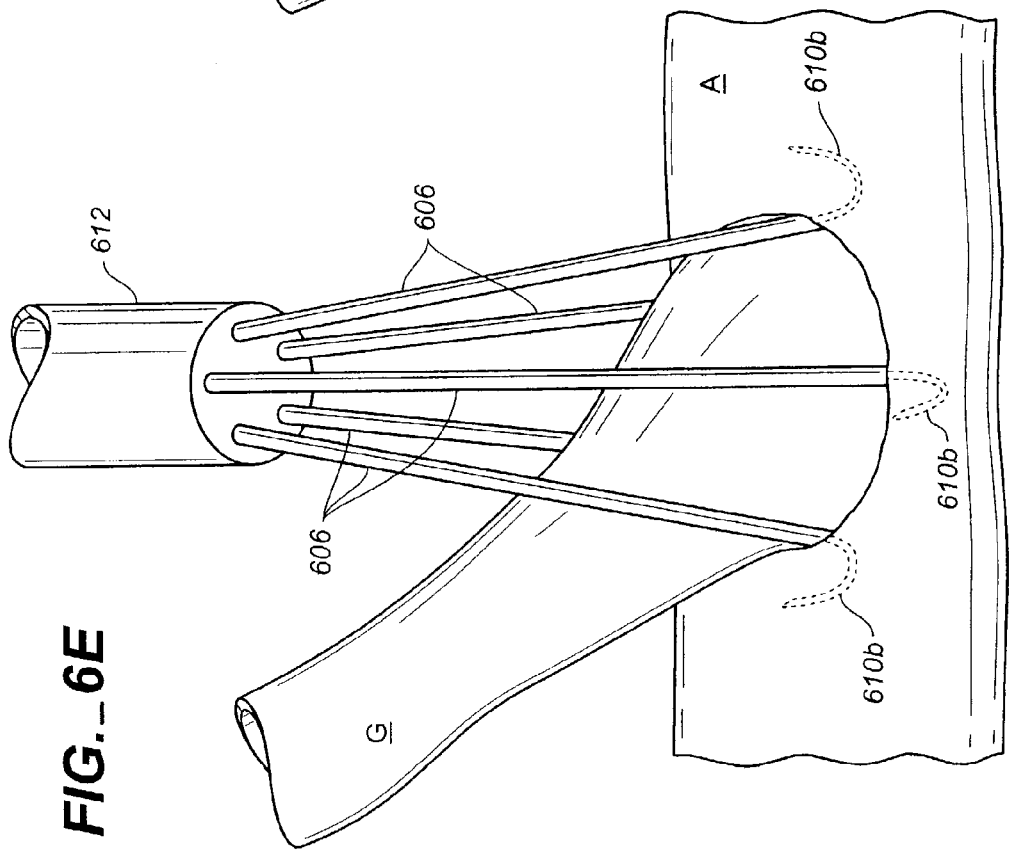

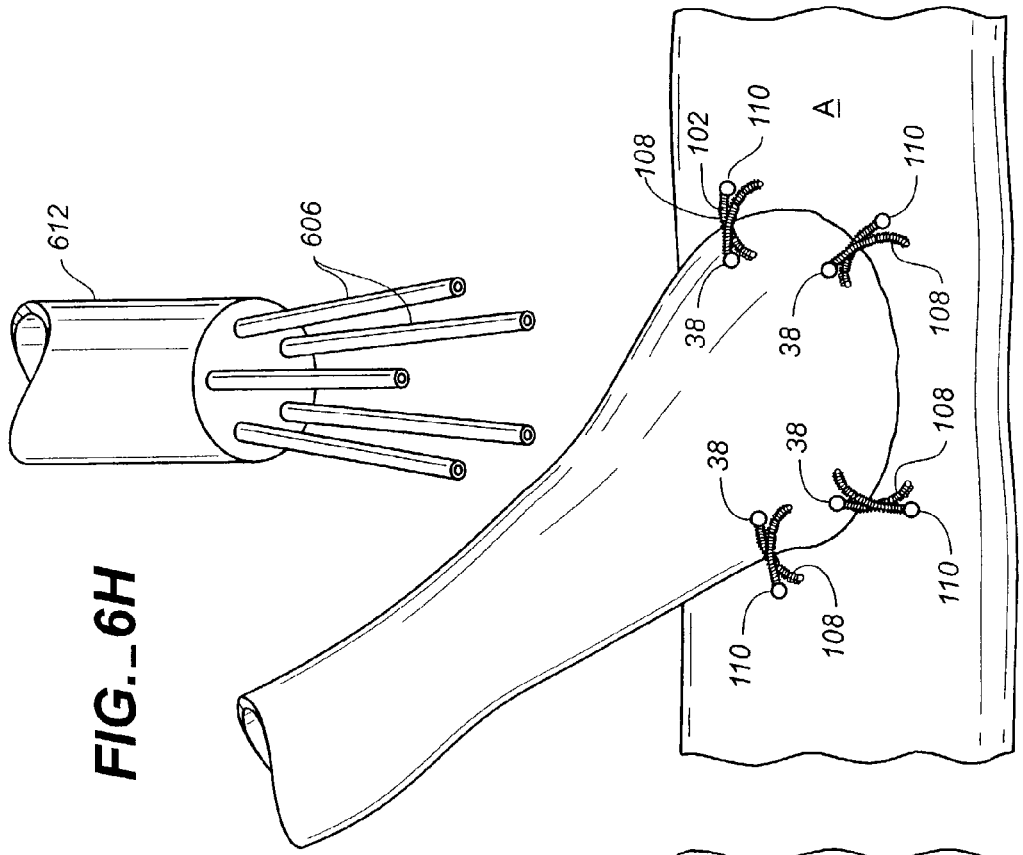
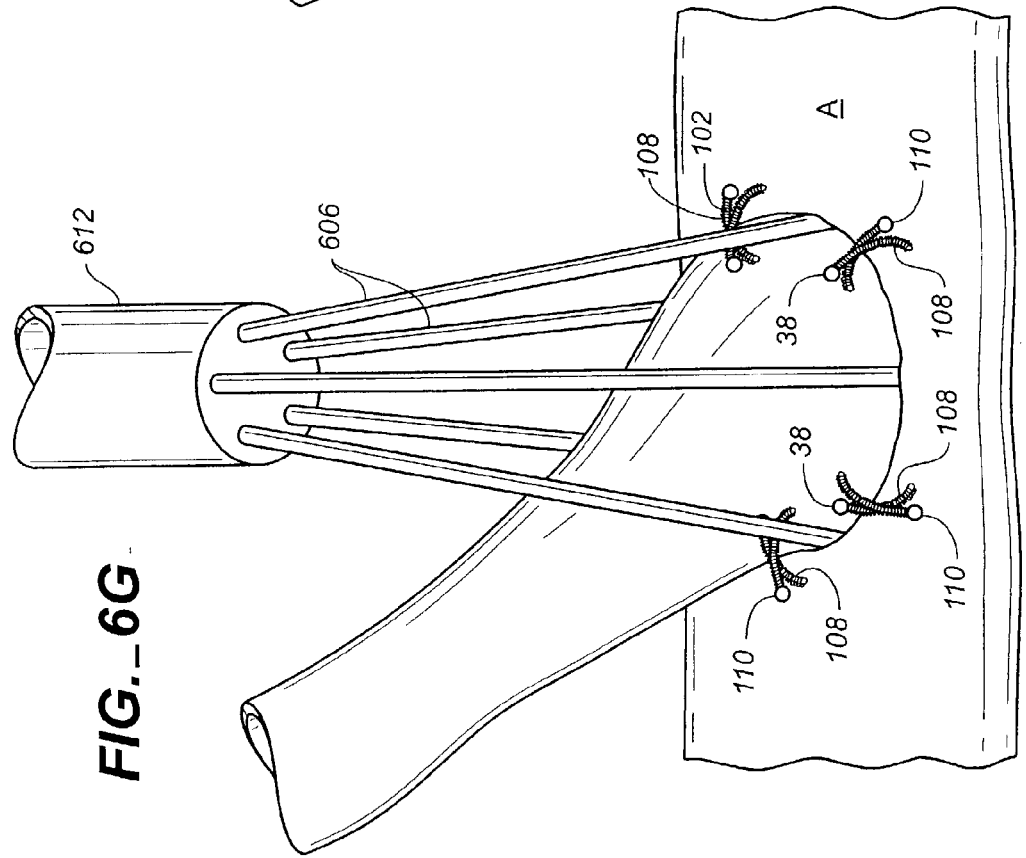

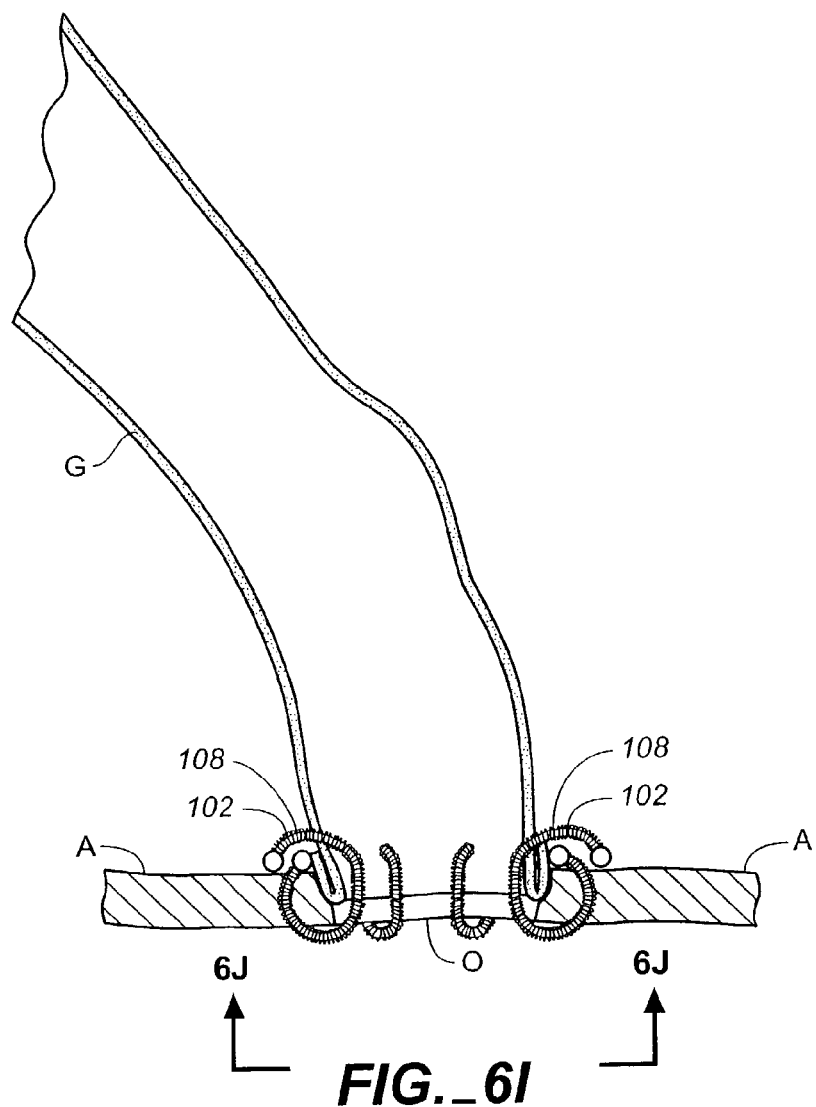
FIG._6I
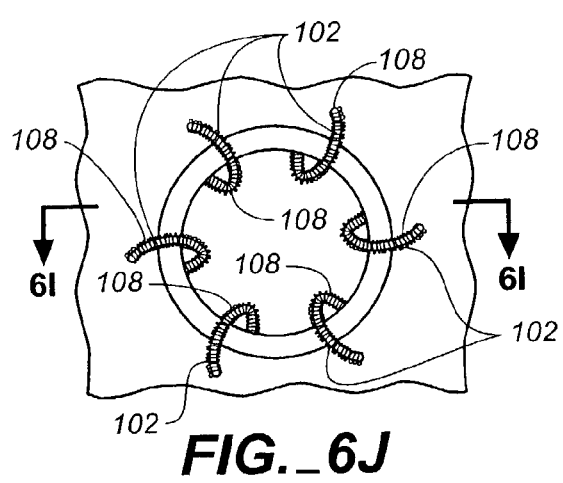
FIG._6J

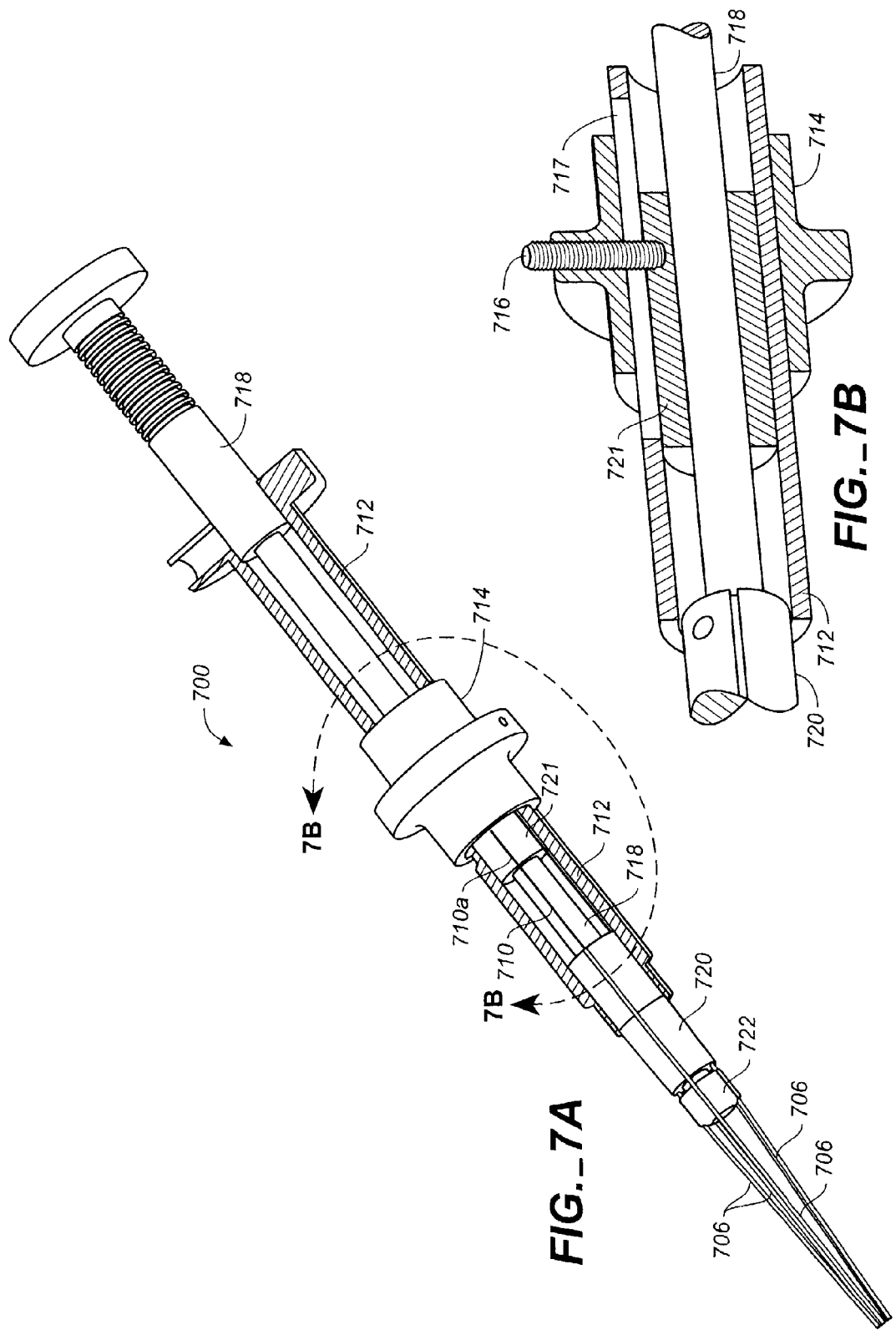

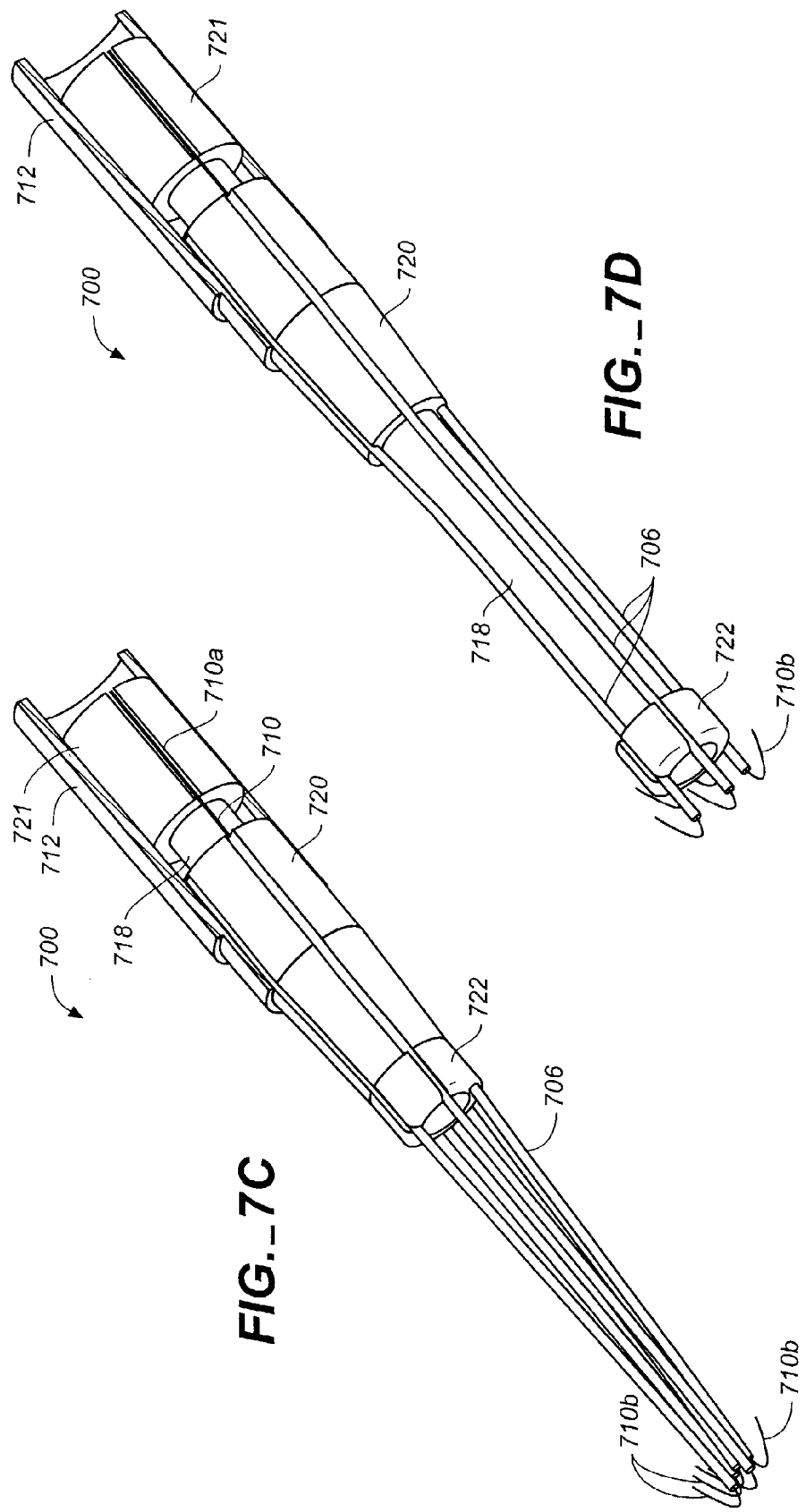

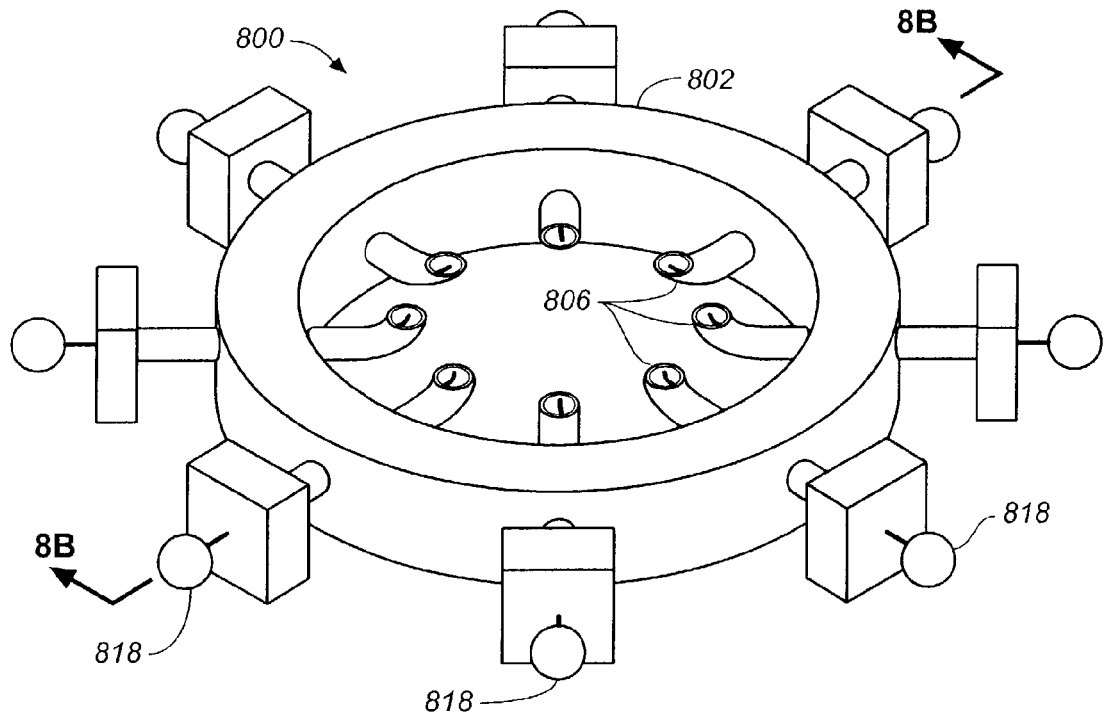
FIG._8A
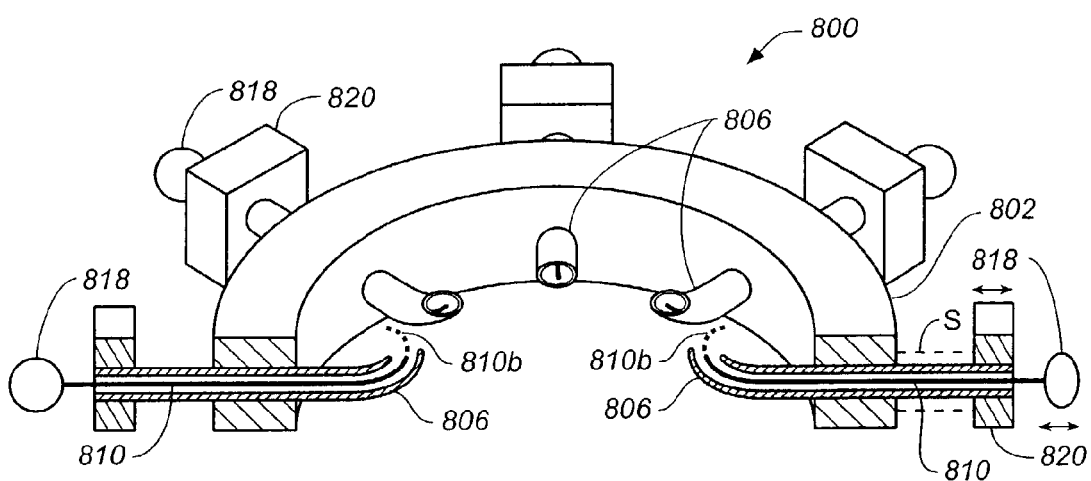
FIG._8B

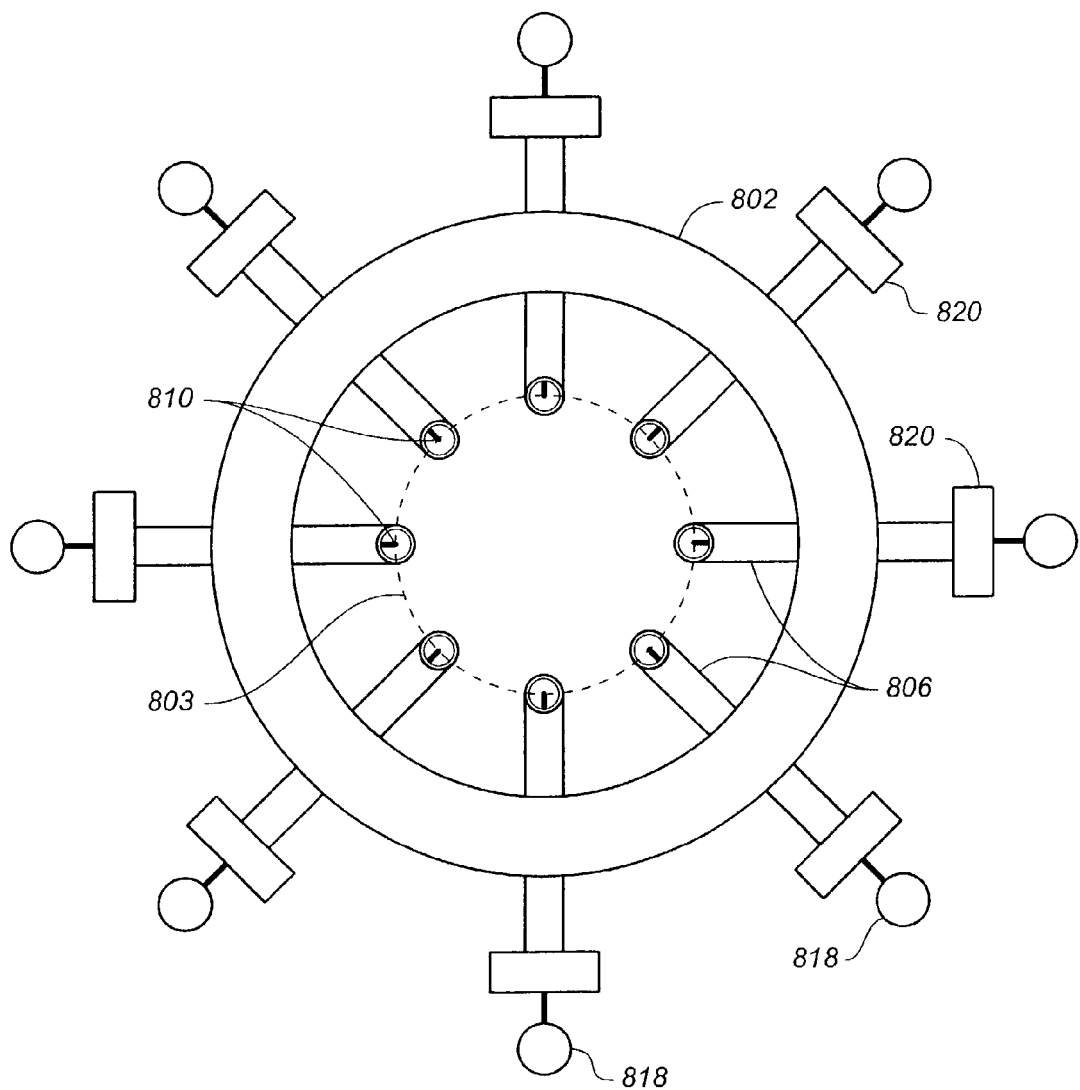
FIG._8C

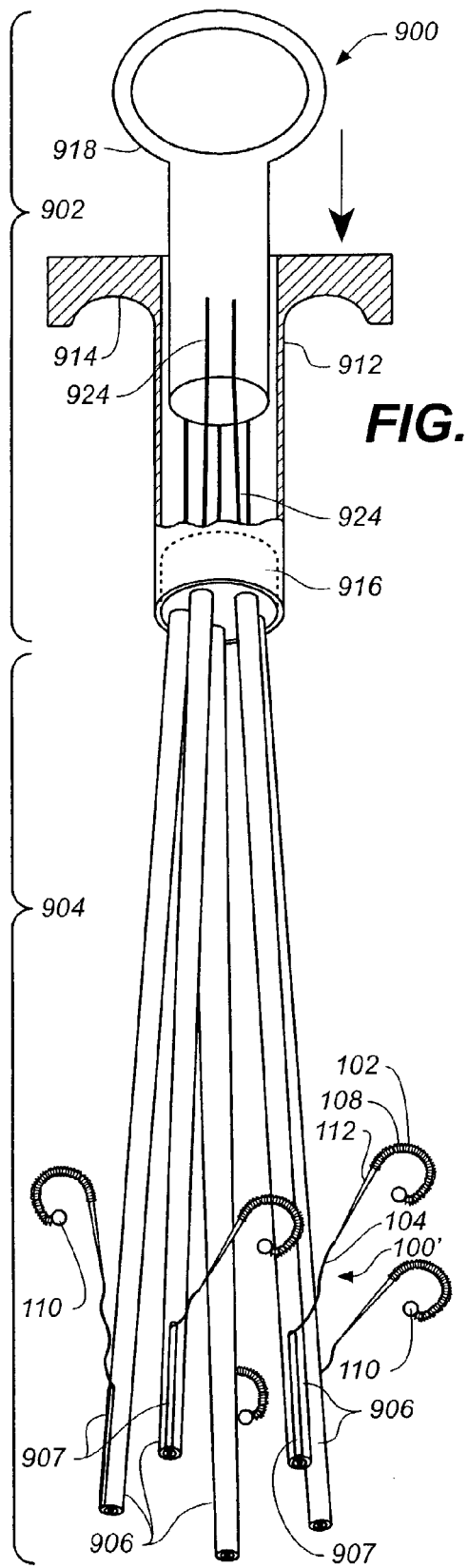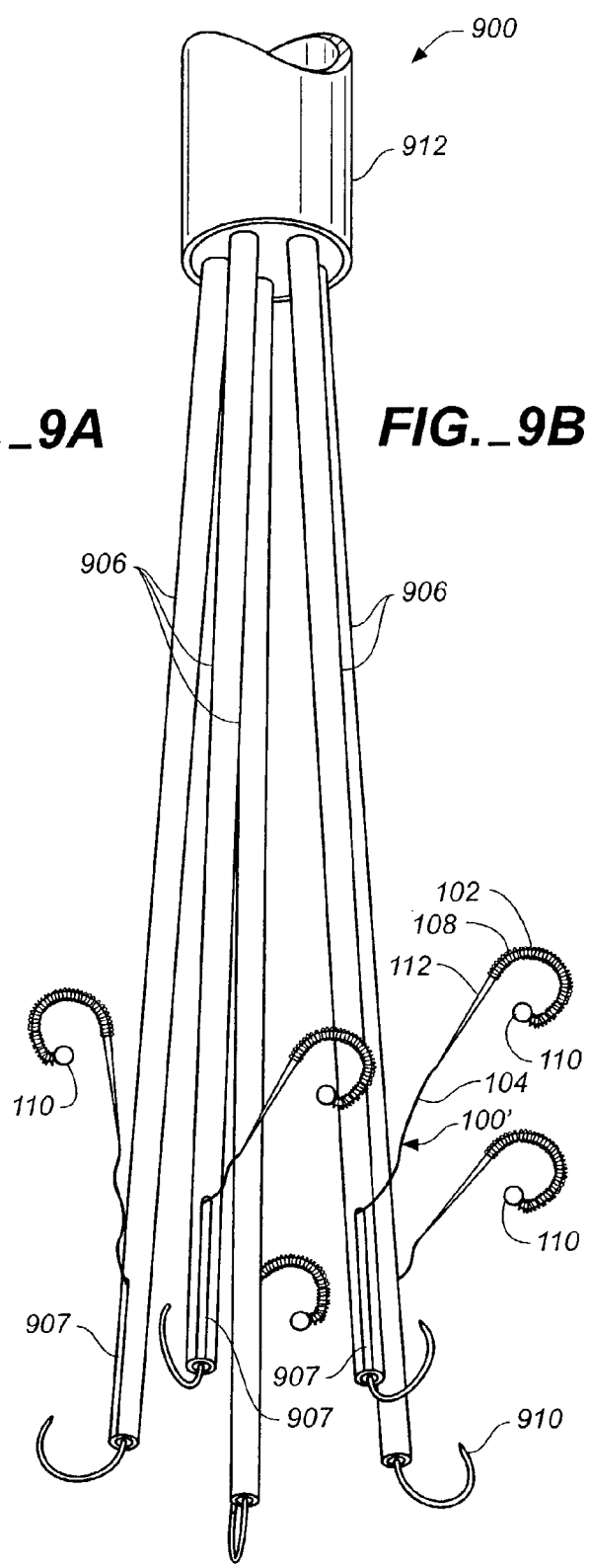
FIG._9A    FIG._9B

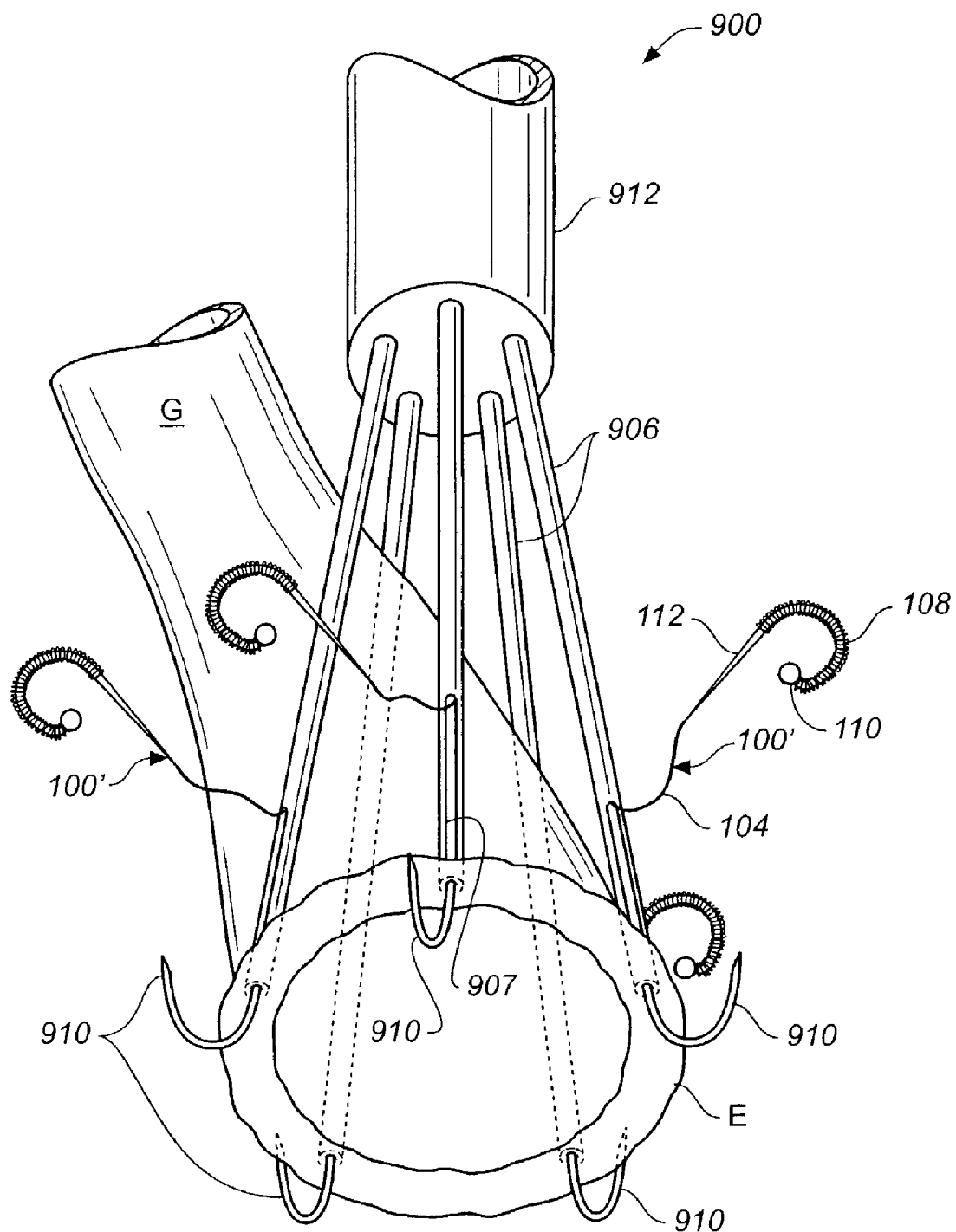
FIG._9C

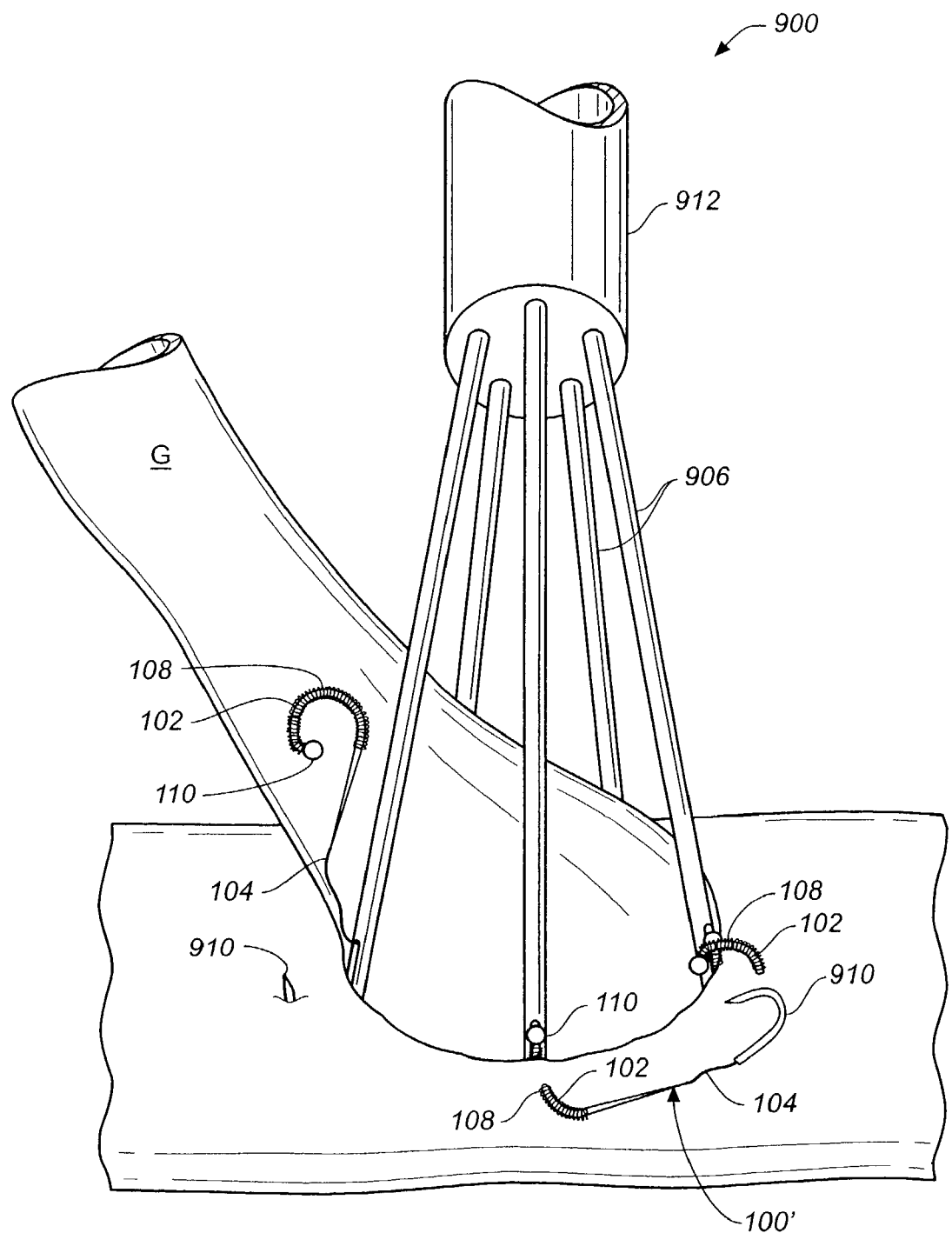
FIG._9D

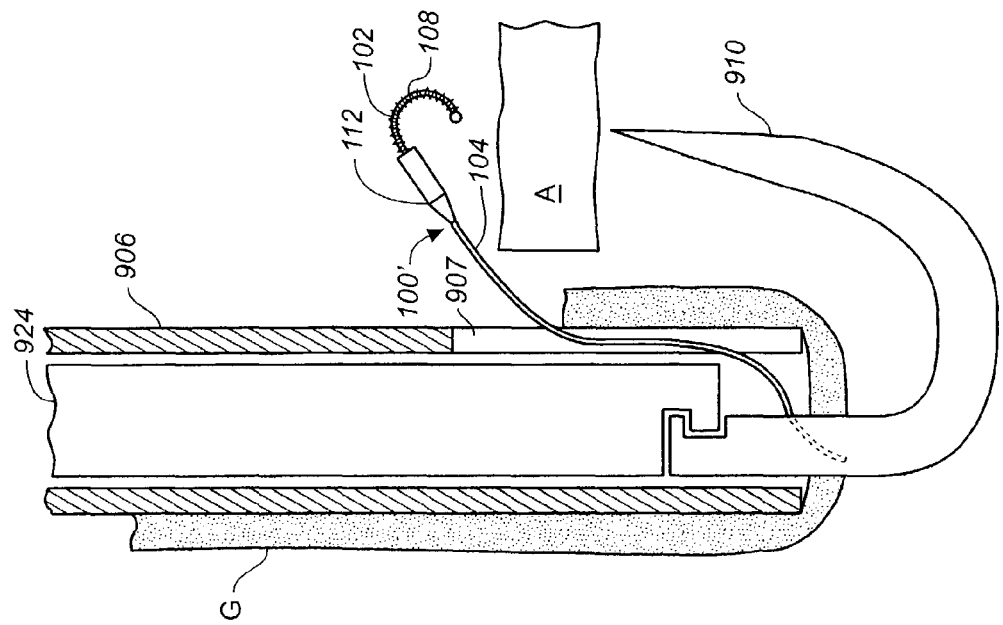
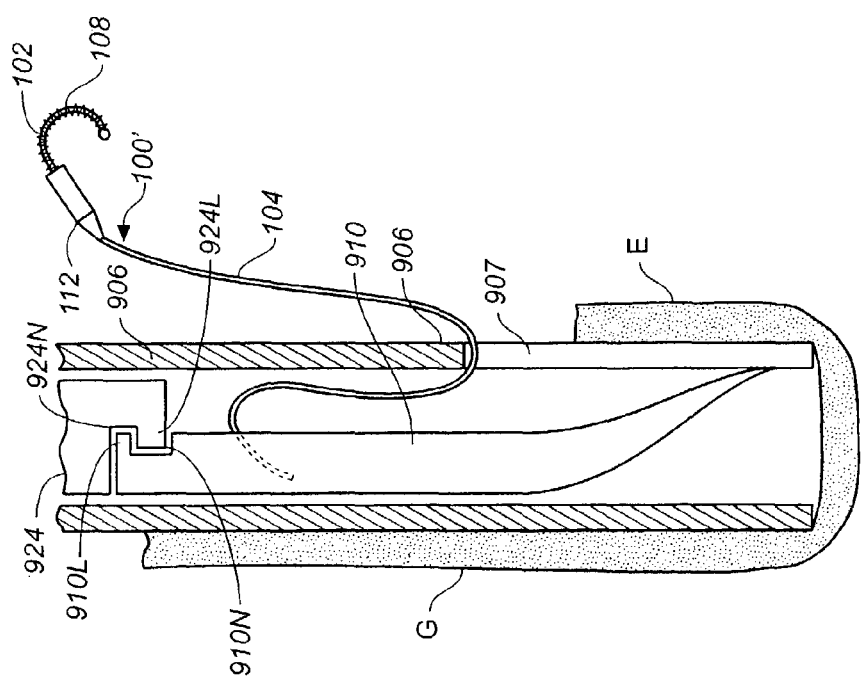

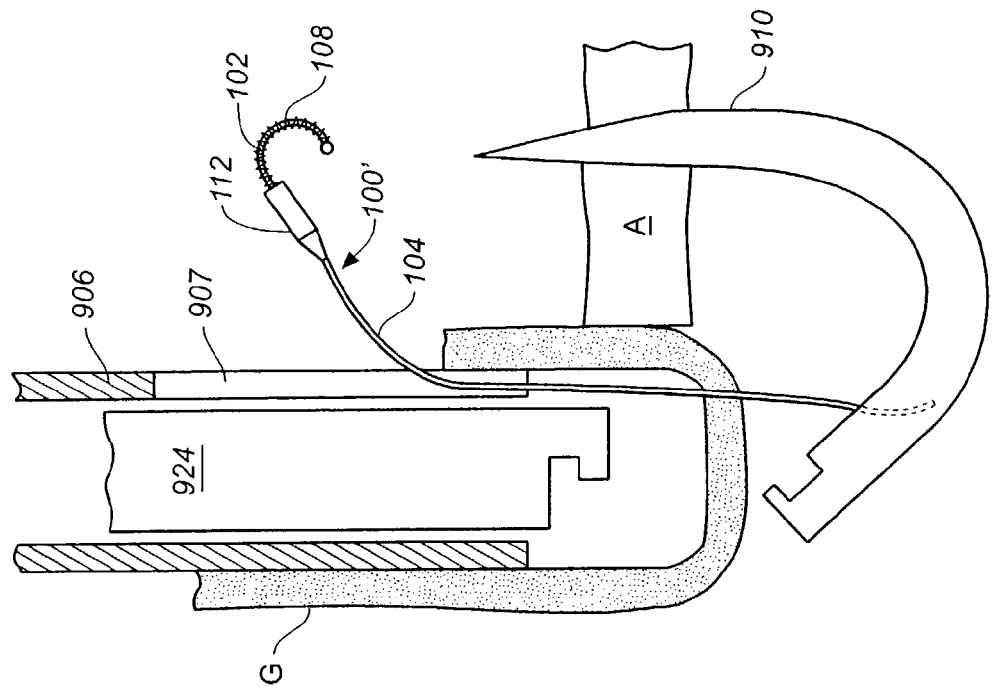
FIG._10D
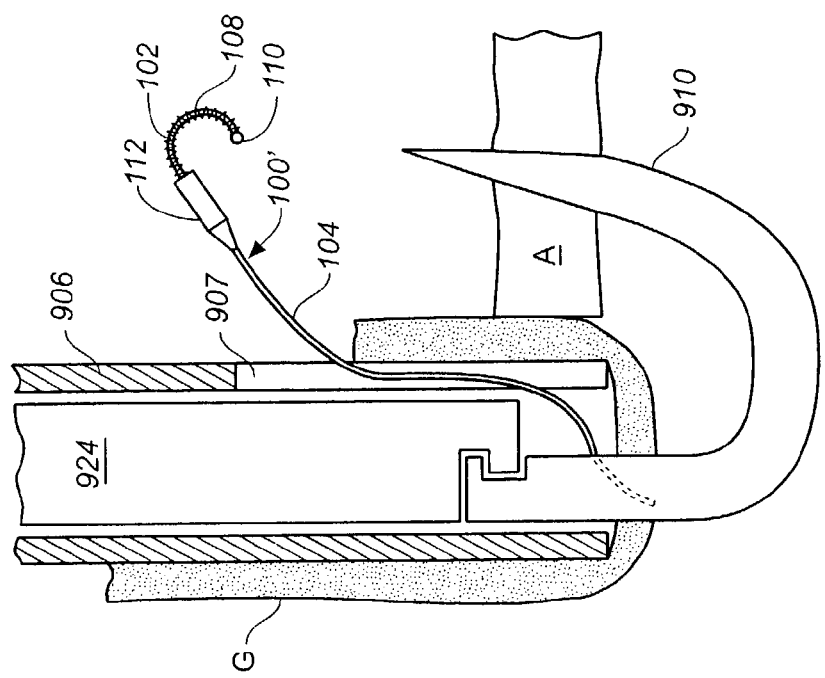
FIG._10C

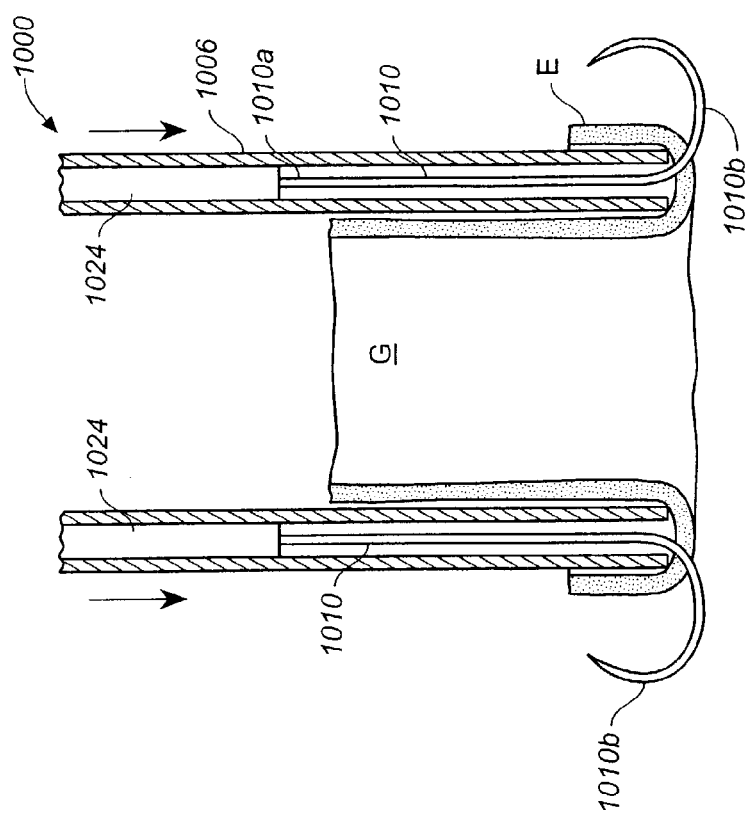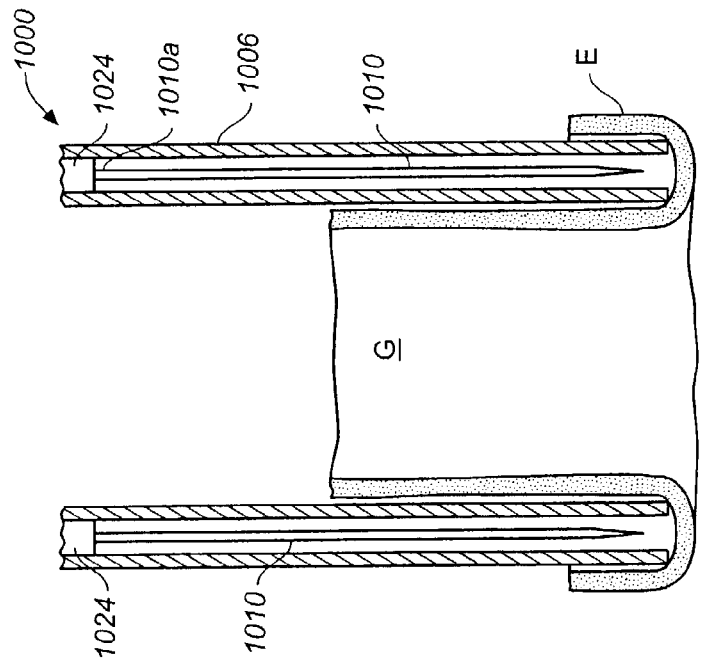
FIG._11B
FIG._11A

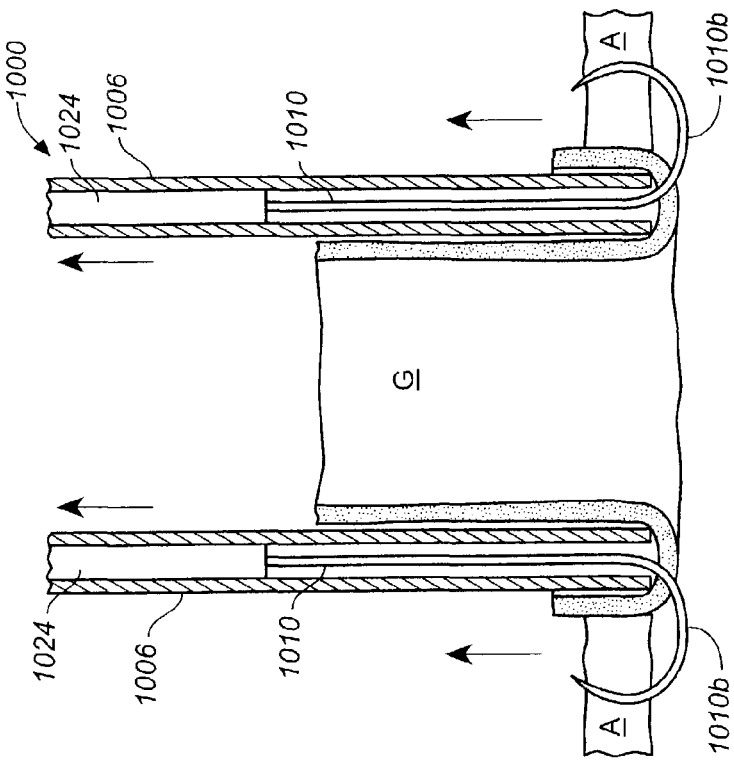
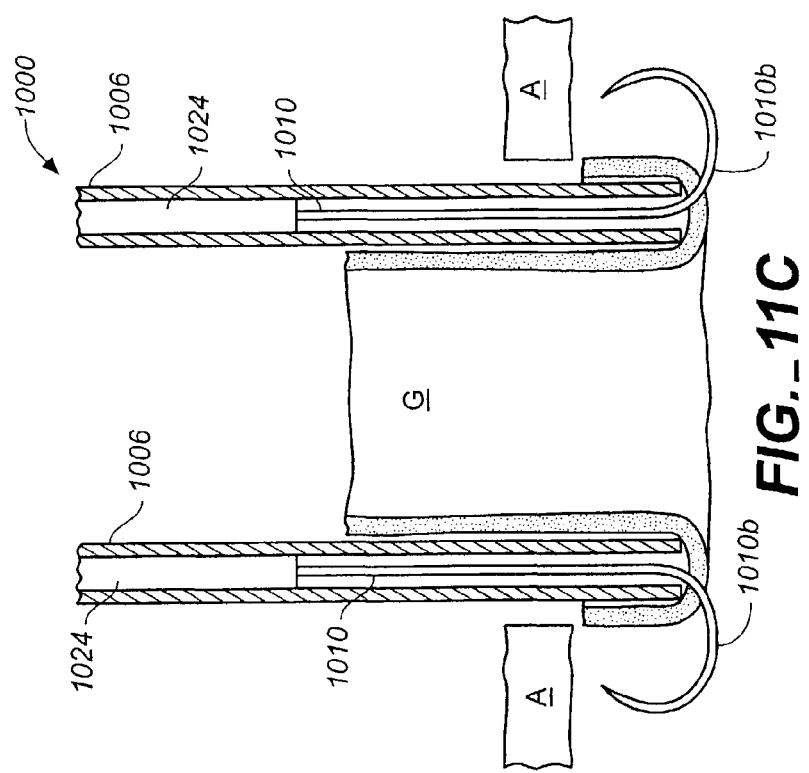

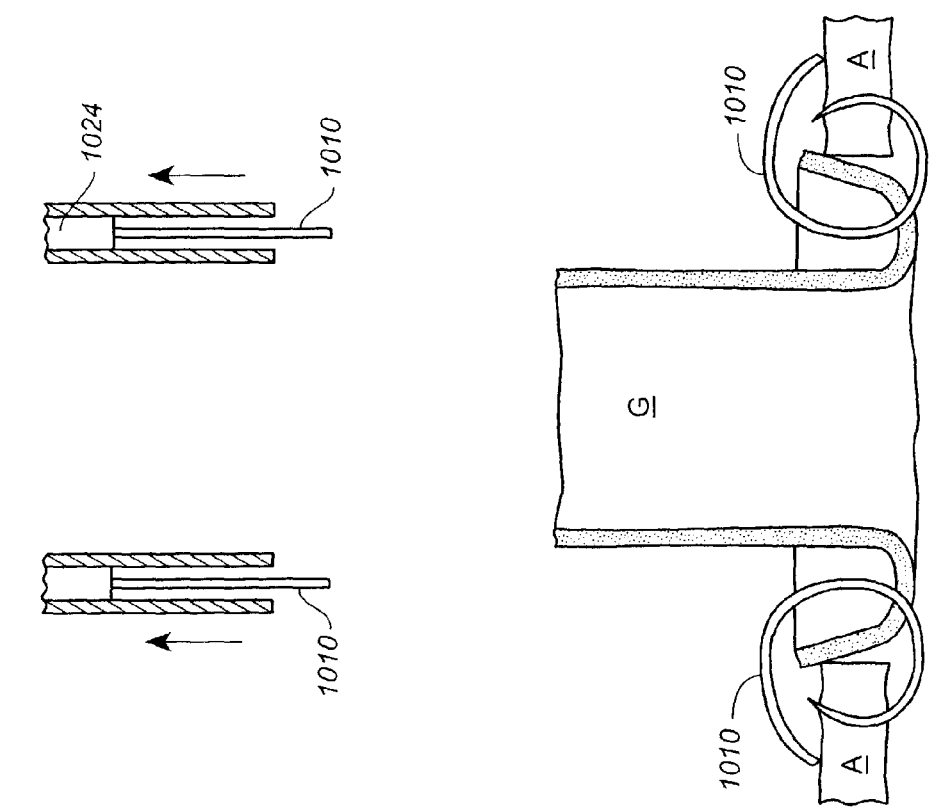
FIG._11F
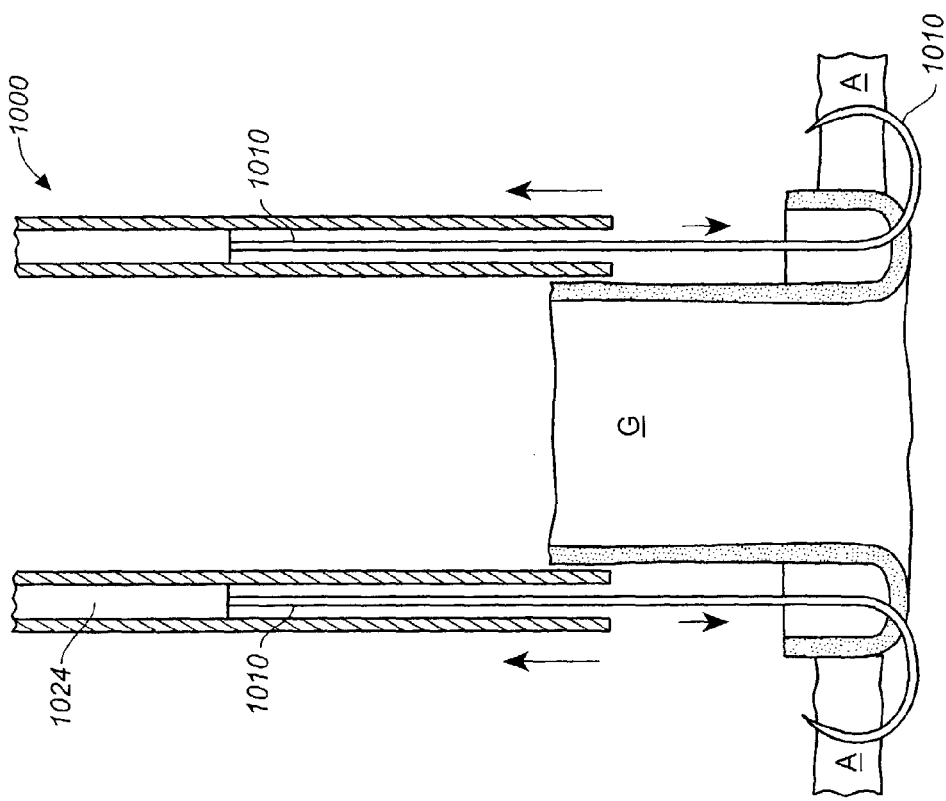
FIG._11E

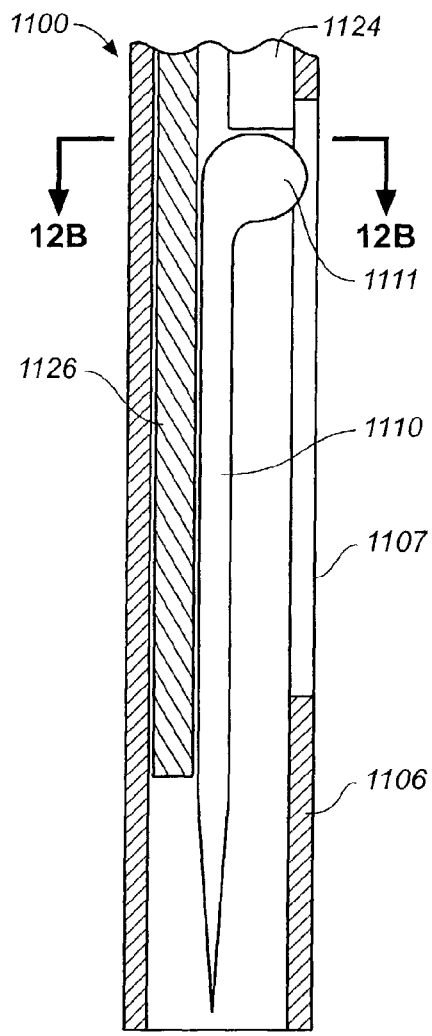
FIG._12A
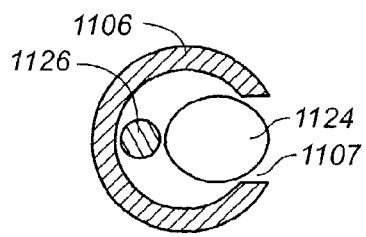
FIG._12B
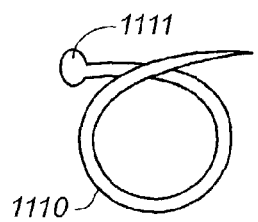
FIG._12C
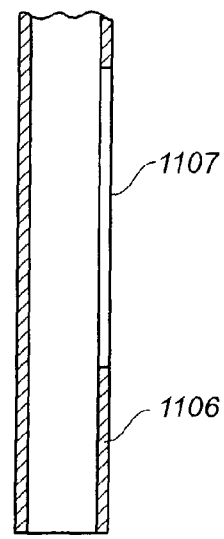
FIG._12D
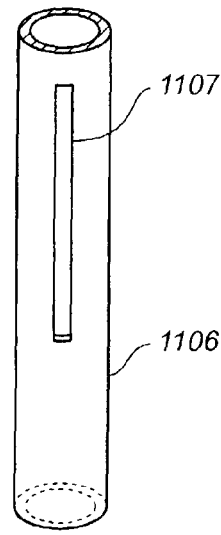
FIG._12E
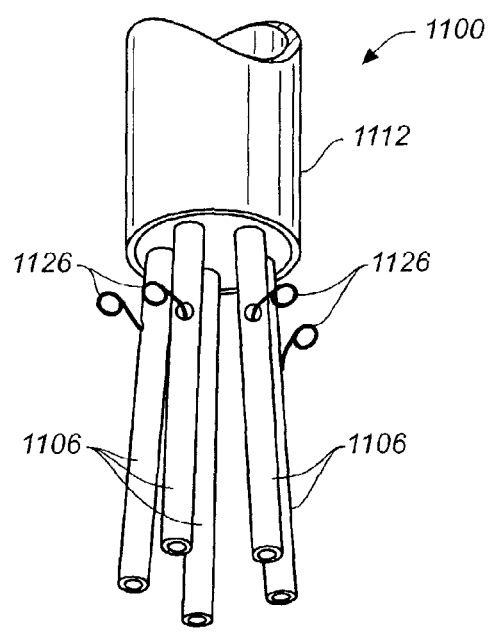
FIG._12F

FIG._13A
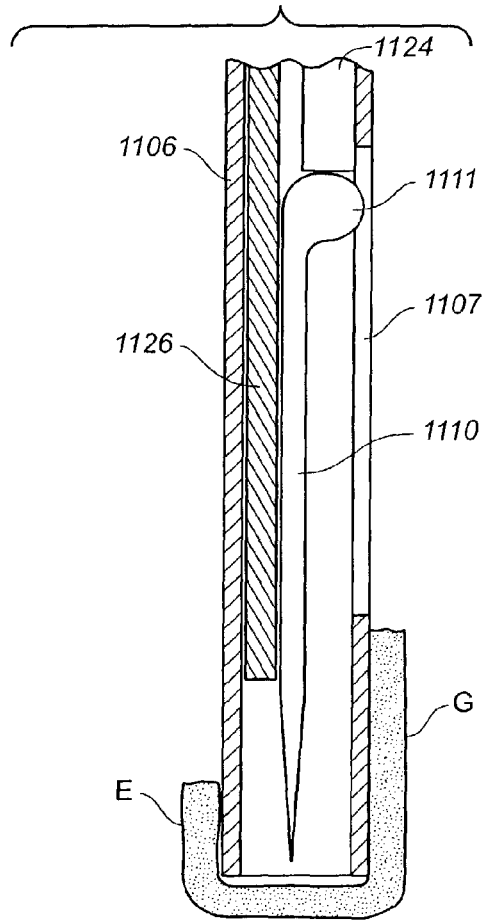
FIG._13B
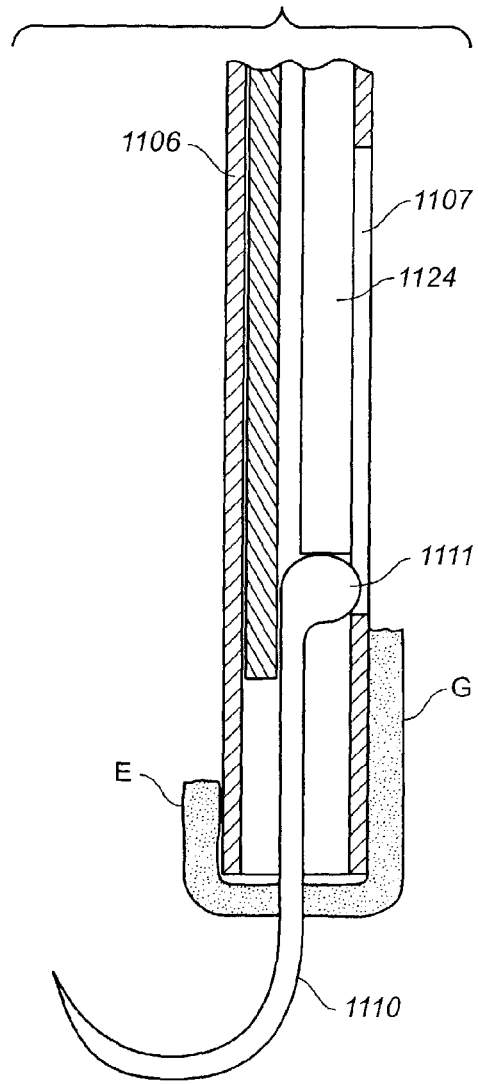
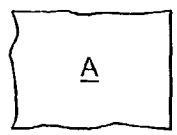
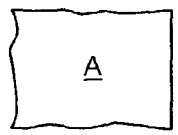

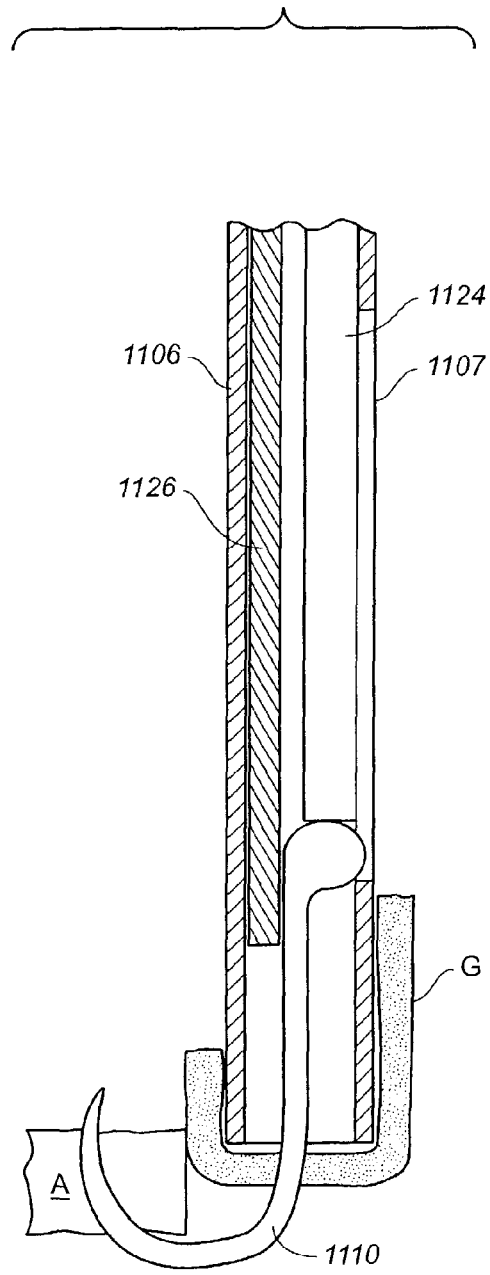
*FIG._13C*
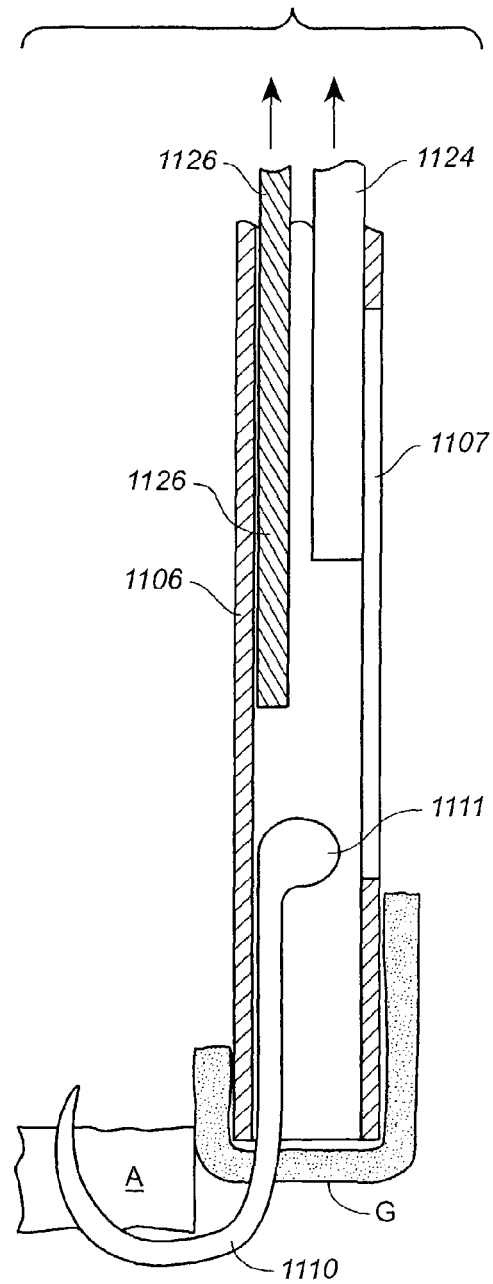
*FIG._13D*

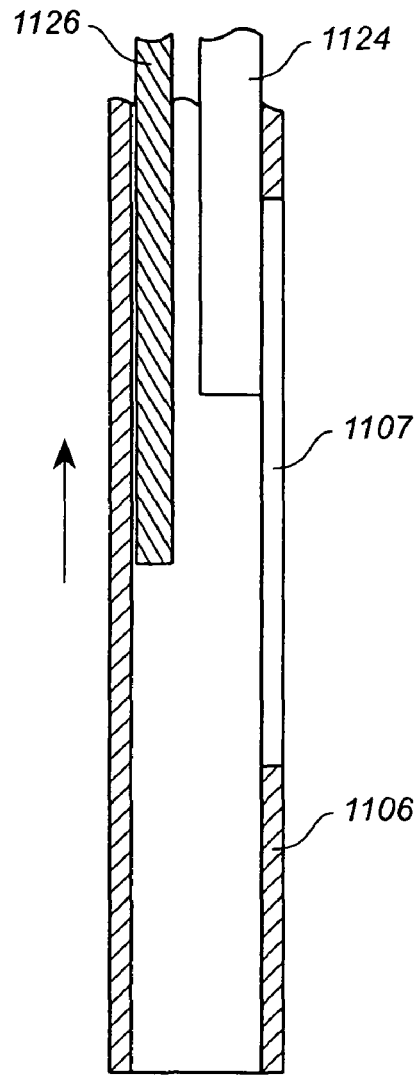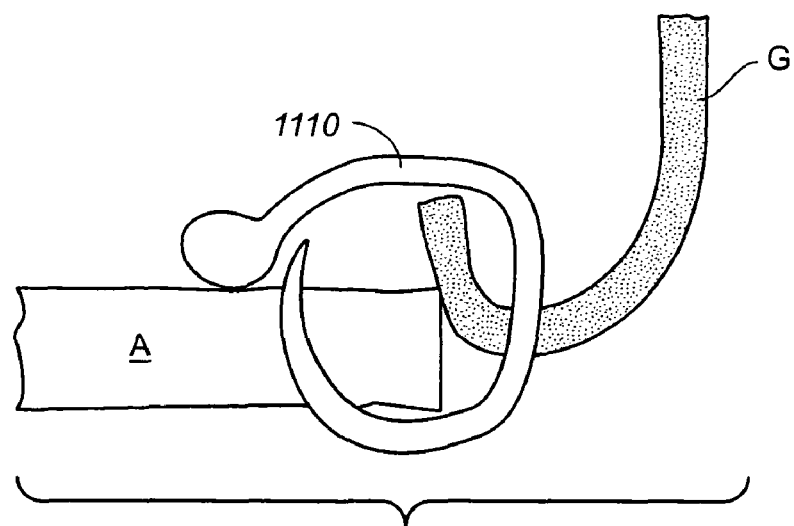
FIG._13E

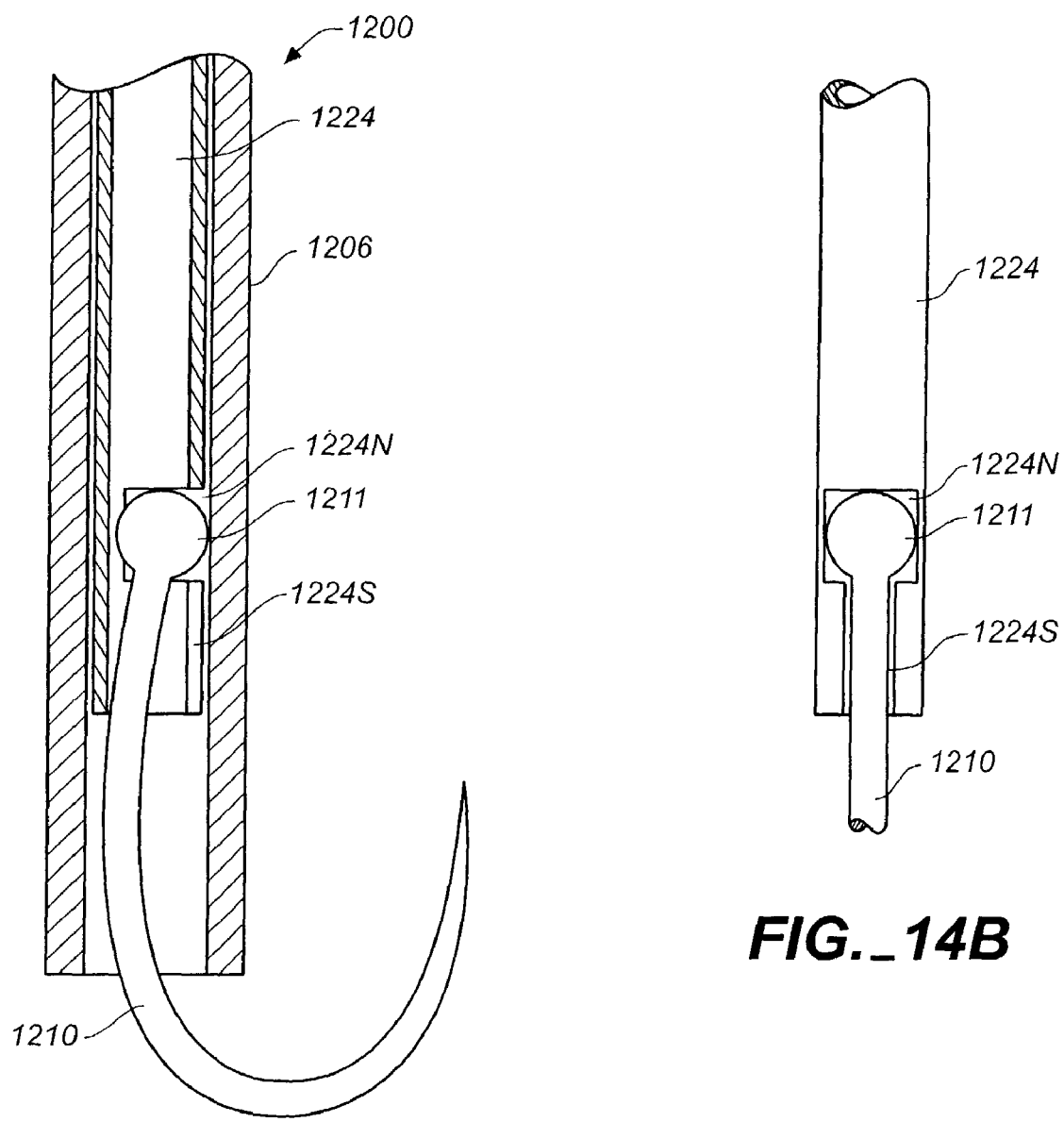
FIG._14A
FIG._14B

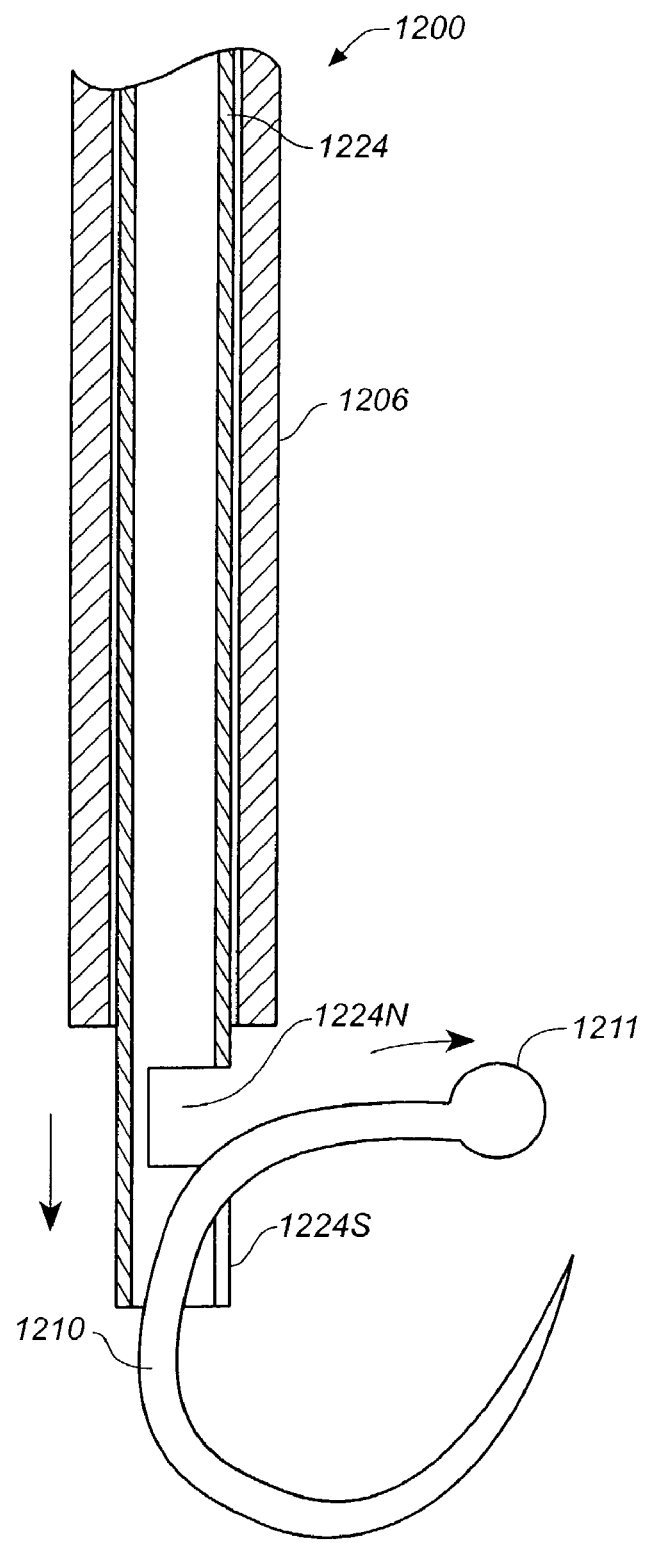
FIG._14C

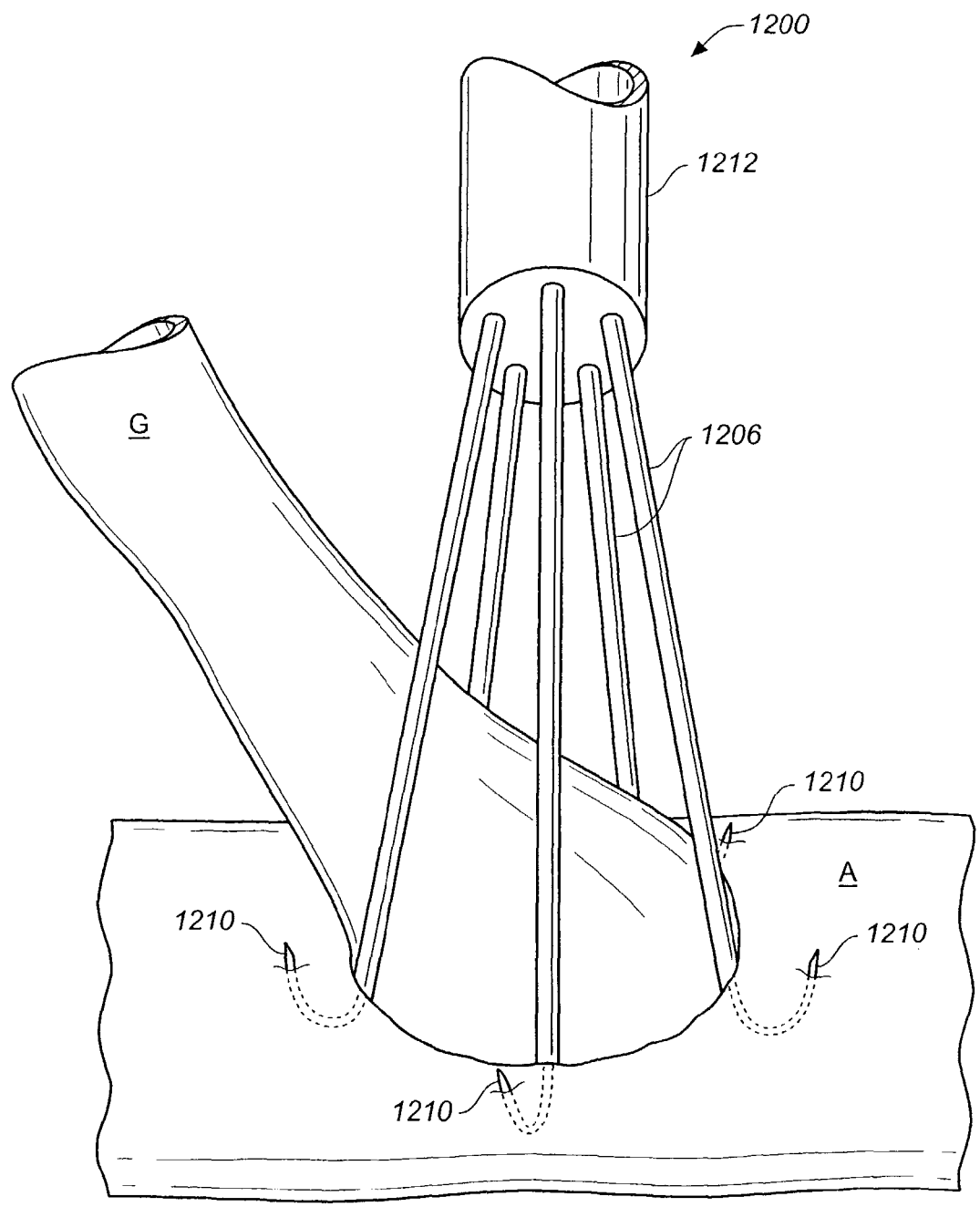
FIG._15A

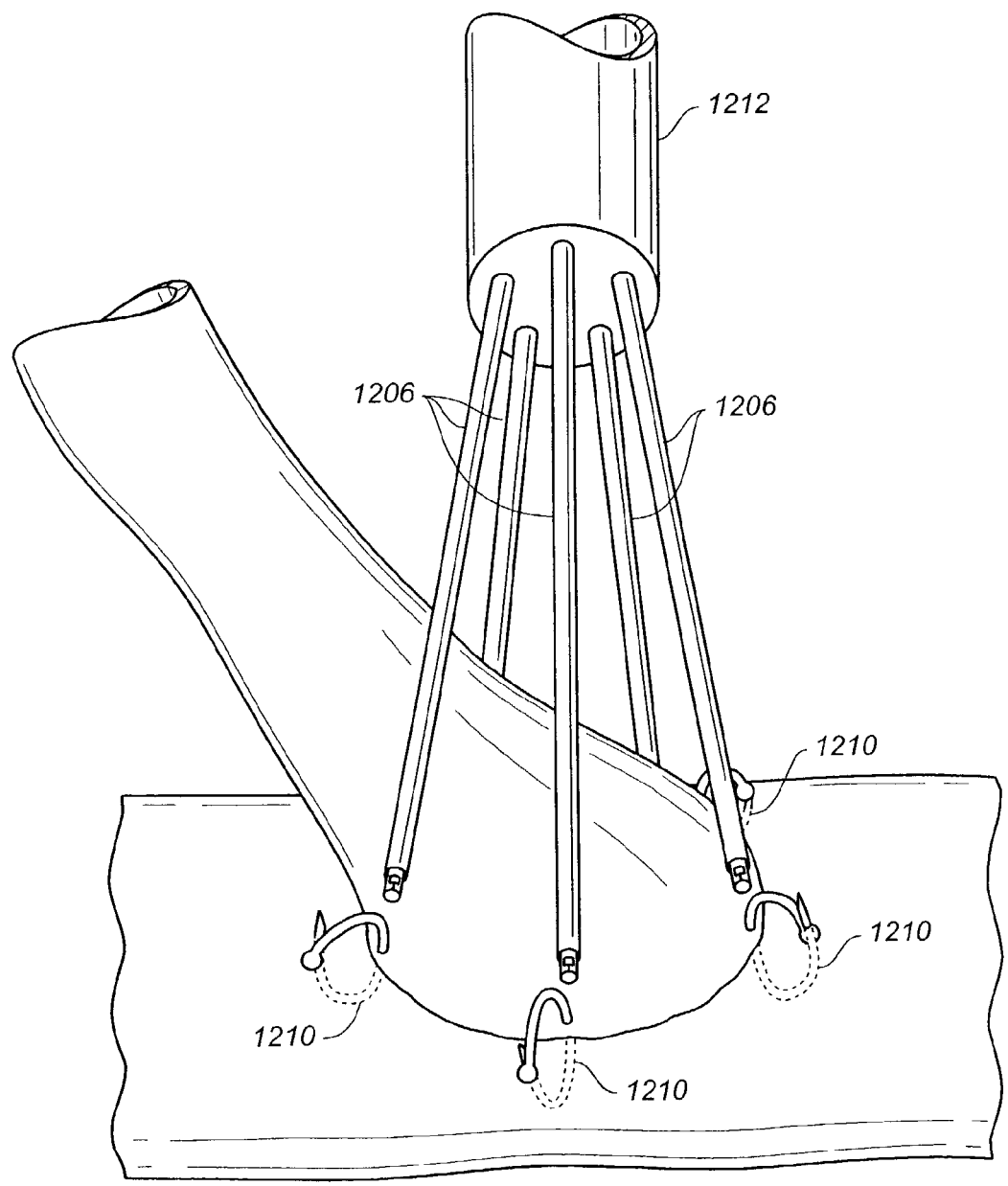
FIG._15B

ANASTOMOSIS APPARATUS AND METHODS

CROSS-REFERENCE

This application also claims the benefit of U.S. Provisional Application No. 60/415,997, filed Oct. 4, 2002, which application is incorporated herein by reference.

FIELD OF THE INVENTION

This invention relates to apparatus and methods for joining tubular structures of which at least one is tissue. More particularly, the invention involves anastomosing these structures. One example application is in a proximal anastomosis.

BACKGROUND OF THE INVENTION

The occlusion of the arteries can lead to insufficient blood flow resulting in discomfort and risks of angina and ischemia. Significant blockage of blood flow in the coronary artery can result in damage to the myocardial tissue or death of the patient. In most cases, occlusion of the artery results from progressive long term deposits of plaque along the artery wall. While such deposits may be concentrated and occlude the artery at a particular site, the deposits are most certainly present throughout the arteries and the vascular system.

Coronary artery bypass graft (CABG) surgery is a surgical procedure performed in severe cases of coronary blockages. CABG procedures involve anastomosing an artery to a vascular graft which restores the flow of blood by establishing another pathway around the occluded vasculature. During coronary artery bypass graft surgery, a vein or other conduit can be attached proximally to the patient's aorta. The other end is attached to the blocked artery, downstream from the obstruction, thus bypassing the coronary occlusion. CABG procedures can be done by placing the patient on a heart-lung machine and stopping the heart from beating or they can be done on a beating heart without a heart lung machine. One problem encountered in either CABG procedure is the need to perform the procedure, while simultaneously maintaining sufficient function of the patient's circulatory system.

In the case where a CABG procedure involves arresting the heart so that blood flow is diverted from the vessel to be anastomosed, the patient's blood circulation is maintained by a cardiopulmonary bypass (CPB). This bypass is accomplished by diverting the blood flow at selected arterial locations. The blood is diverted to the bypass system for release of carbon dioxide and subsequent oxygenation. Then, the blood is returned to the patient via a pump. Examples of these procedures are found in U.S. Pat. No. 5,799,661 to Boyd, et al. which discloses a device and method for performing CABG surgery for multi-vessel coronary artery disease through port-access or closed-chest thorascopic methods; and U.S. Pat. No. 5,452,733 to Sterman, et al. which discusses performing grafts with an efficacy equal to or greater than conventional open surgical bypass techniques.

Although the beating heart CABG procedure eliminates the need for CPB, it has required diverting blood flow for a proximal anastomosis, such as one which attaches graft material (e.g., a graft vessel) to the ascending aorta. To attach the graft to the aorta in a beating heart situation, surgeons have typically used a "side-biting clamp" that isolates the aortic region where the anastomosis will be performed. This allows the surgeon to create the anastomosis without the site being exposed to the high-pressure blood flow of the normal aorta.

Among the drawbacks associated with aortic clamping are an increased chance of trauma to the arteries caused by ligatures at the clamped site and the possible dislodging of plaque within the clamped vessel wall. As mentioned above, the arterial bypass may be required due to the deposits of plaque which have occluded the vessel. However, the plaque is typically present throughout the artery and is not limited to the occluded location. Clamping the artery creates a risk of plaque being released into the blood stream. This release of plaque has the potential of causing a stroke, occlusion of a smaller peripheral vessel, or other vascular trauma. In a beating heart procedure, full clamping (i.e., cross clamping) of the aorta for graft attachment at the proximal anastomosis is not feasible. Therefore a side biting clamp is used to clamp off only a portion of the cross-section of the aorta, where the proximal anastomosis is performed. This type of clamping procedure poses the same risks described above with regard to cross clamping, e.g., the risk of release of plaque and resultant cause of a stroke, occlusion of a smaller peripheral vessel, or other vascular trauma.

Other attempts to address the problem related to blood flow diversion include diverting the blood by placing a balloon catheter within the aorta, such as described in U.S. Pat. No. 5,868,702 to Stevens, et al., for example. Drawbacks of using a balloon catheter in creating a seal to divert blood flow include the possibility of disturbing plaque deposits and creating particles in the blood stream, the chance that the balloon catheter may move within the aorta disrupting the seal and resulting in blood loss, and trauma to aortic tissue caused by the pressure needed to create the seal.

There remains some concern in the surgical community that neurological defects and strokes are associated with the use of heart-lung machines, side-biting clamps, and balloon occlusion devices.

PCT Patent Application No. PCT/US98/10245, to Cardio Medical Solutions and to Nobles, et al., which published under Publication No. WO 98/52475, attempts to address problems associated with diverting blood flow. Nobles, et al. provides a method and device for creating an area of hemostasis within a blood vessel without interrupting the flow of blood through the vessel which eliminates the need to clamp the vessel. However, the Nobles, et al. device requires the withdrawal of the hemostasis device prior to obtaining a tight seal between the graft and vessel. Therefore, since the area of hemostasis is lost upon the retrieval of the hemostasis device, the artery is open and blood is lost until the sutures are tightened.

Yet another problem related to CABG procedures lies in the procedure of suturing the vessels to create a tight seal. To ensure the integrity and patency of the anastomosis, the graft and vessel to be joined thereto must be precisely aligned with respect to each other. If one of the tissues is affixed too close to its edge, the suture can tear through the tissue and impair both the tissue and the anastomosis. Another problem is that, even after proper alignment of the tissue, it is difficult and time consuming to pass the needle through the tissues, form the knot with the suture material, and ensure that the suture material does not become entangled. These difficulties are exacerbated by the small size of the artery and graft. Another factor contributing to the difficulty of the CABG procedure is the limited time available to complete the procedure. The surgeon must complete the graft in as little time possible due to the absence of blood flowing through the artery. If blood flow is not promptly restored, sometimes in as little as 30 minutes, the tissues the artery supplies may experience significant damage or necrosis. As mentioned above, surgeons are under pressure to reduce the cross-clamp time, yet, an incomplete suture may result in a leak in the tissue approximation between the vessel and graft. Moreover, the tissue approximation must be smooth and open. Hence, the suture cannot be hastily performed.

Additionally, the difficulty of suturing a graft to an artery using minimally invasive surgical techniques, where the surgeon uses ports to access the internal organs to perform the procedure, has effectively prevented the safe use of complicated suturing technology in cardiovascular surgical procedures. Accordingly, many procedures are performed invasively and require a sternotomy, an opening of the sternum. As a result, the recovery times for patients is significantly increased. U.S. Pat. No. 5,868,763 to Spence, et al. attempts to circumvent the suturing process by attaching the vessels to a cuff device. Spence, et al. utilizes a passageway for continued blood flow so there is no clamping of the artery.

Arcia, et al., in U.S. Pat. No. 6,358,258, describes systems and methods for performing anastomosis or attachments of body ducts, which are asserted to simplify suture delivery in both stopped heart and beating heart procedures and to be suitable for use in a minimally invasive environment using percutaneous ports, or with retractor systems or in a generally open surgery environment.

Houser, et al., in U.S. Pat. No. 5,989,276, discloses various devices and techniques for performing bypass, one of which includes a device which can be intralumenally originated. Various other clamping arrangements are provided for securing a graft to a vessel without the use of sutures or other fasteners.

In PCT Application No. PCT/GB01/04666, to Anson Medical Limited and to Hopkinson, et al., and which published under Publication No. WO 02/34143, apparatus is described for carrying out an anastomosis by sealing an arteriotomy and connecting a graft to the artery with the seal in place (see the Abstract). The apparatus includes means for sealing the hole and means for locating the graft on the outside of the wall of the artery. Once the graft is completely connected, the seal can be removed from the artery through the bore of the graft. Means may be provided for clamping the graft and seal in place while the graft is being connected to free both of the surgeon's hands for the connection operation.

The problems discussed above can be exacerbated in those cases where a multiple anastomosis is required. In those cases where multiple bypass procedures are performed, the patient will naturally be subject to increased risks as multiple grafts must be sutured to perform the bypass. Therefore, there is a need to improve and simplify anastomosis procedures.

SUMMARY OF THE INVENTION

The present invention involves improvements in anastomosis apparatus and methods for anastomosing a first tubular structure to a second tubular structure.

According to one embodiment of the invention anastomosis apparatus for anastomosing a first tubular structure to a second tubular structure having a sidewall with an opening formed therein, the apparatus comprises a support device having a first portion and a second portion adapted to support an everted portion of the first tubular structure and having a radius and radially adjustable portions, the second portion further including a plurality piercing members slidably coupled thereto and adapted to pierce and hold a portion of the first and second tubular structures.

With this construction, the device can be used to position the first tubular structure (e.g., a graft) in sealing relationship with an opening formed in the second tubular structure prior to passing the fasteners through the first and second tubular structures. The slidably coupled piercing members also improve the procedure for coupling the everted portion of the first tubular structure to the apparatus.

According to another embodiment, apparatus for anastomosing a first tubular structure to a second tubular structure, having a sidewall with an opening formed therein, comprises a support having a body portion, a plurality of arms extending from the body portion, and a plurality of tissue piercing members each being adapted to pierce a portion of the first and second tubular structures, each of the plurality of arms forming a pathway in which one of the plurality of tissue piercing members is slidably mounted, each of the plurality of arms further having a distal end from which one of the tissue piercing members can be extended and a proximal end, the distal ends are collectively adapted to receive an end portion of the first tubular structure everted thereover. The distal ends can be radially movable so that they can be moved radially outward after introduction in the opening in the second structure to enhance or form a seal between the first tubular structure and the second tubular structure.

Regarding the radially movable aspect in described above, a member can be slidably mounted within the collective arrangement of arms, which are arranged so that when sliding member moves distally the distal portions of the arms move radially outward and when the sliding member moves proximally the distal portions of the arms move radially inward.

In any of the embodiments described above, a plurality of discrete fasteners can be provided to pass through the support device spaces and the first and second tubular structures. Alternatively, fasteners can be combined with or integrated into the apparatus (e.g., the piercing members), and releasably coupled thereto for delivery to the anastomosis site.

According to a further aspect of the invention, the need for clamping or interrupting fluid flow through the second or target tubular structure can be avoided. In the case where the target tubular structure is a blood carrying vessel (e.g., a patient's aorta), the seal that can be achieved between the first and second tubular structures, which minimizes or eliminates bleeding from the opening in the target tubular structure. Without removing the seal, fasteners can be passed through the spaces or openings between the arms and through the tubular structures to secure the first and second tubular structures together.

According to one method of the present invention, a first tubular structure having an end portion to a second tubular structure having an opening formed therein, where at least one of the structures is tissue, comprises providing a support device including a plurality of arms having a proximal end, a distal end, and a plurality of piercing members extending therefrom; advancing the piercing members from the arms and through the first tubular structure to secure the first tubular structure to the plurality of piercing members; positioning the support device so that the tubular structures contact one another; passing a plurality of surgical fasteners between selected arms of the support device and through the tubular structures to secure the tubular structures together; and removing the support device from the tubular structures.

The above is a brief description of some deficiencies in the prior art and advantages of the present invention. Other features, advantages, and embodiments of the invention will be apparent to those skilled in the art from the following description, accompanying drawings, wherein, for purposes of illustration only, specific forms of the invention are set forth in detail.

BRIEF DESCRIPTION OF THE DRAWINGS

FIG. 1A is a perspective view of an anastomosis device;
FIG. 1B shows the device of FIG. 1A with a graft mounted thereto;
FIG. 1C shows another embodiment of an anastomosis device;

FIG. 1D is a perspective view of yet another embodiment of an anastomosis device;

FIG. 1E is a longitudinal cross section of the anastomosis device shown in FIG. 1D including a graft mounted thereto;

FIG. 1F is a perspective view of a yet a further embodiment of an anastomosis;

FIG. 1G is a longitudinal cross section of the anastomosis device shown in FIG. 1F taken along line 1G-1G including a graft mounted therein;

FIGS. 2A, 2B, 2C, 2D, 2E, 2F, and 2G diagrammatically illustrate a method of using of the apparatus of FIGS. 1A and 1B to perform a proximal anastomosis, where:

FIG. 2A is a longitudinal section of the device of FIG. 1 illustrating a vessel graft (e.g., vein graft) positioned therein;

FIG. 2B shows the graft and support combination of FIG. 2A after the graft vessel is everted over the end of the device;

FIG. 2C shows the graft-device combination of FIG. 2B positioned within an opening formed in an artery and the placement of diametrically opposed fasteners to hold the graft to the tissue adjacent to the artery opening;

FIG. 2D shows placement of further fasteners to secure the graft to the artery and removal of the assist device;

FIG. 2E is a view of the anastomosis shown in FIG. 2D and taken along line 2E-2E;

FIG. 2F is of another anastomosis configuration made with the device of FIG. 1A; and FIG. 2G is a view the anastomosis shown in FIG. 2F taken from the inside of the target vessel as in FIG. 2E;

FIG. 3 is a perspective of a suitable fastener for use in conjunction with embodiments described herein;

FIGS. 4A, 4B, 4C, and 4D are various views of the fastener shown in FIG. 3;

FIG. 5A is a partial sectional diagrammatic view of another anastomosis apparatus, which is constructed according to the principles of the present invention with slidably mounted graft engagement needles retracted within the arms;

FIG. 5B shows the apparatus of FIG. 5A with the graft piercing members extended;

FIG. 5C is a sectional view taken along line 5C-5C of FIG. 5B;

FIGS. 6A-L diagrammatically illustrate a method of performing a proximal anastomosis using the apparatus of FIG. 5A, where:

FIG. 6A is a perspective view illustrating a graft (e.g.; vein graft) positioned everted over the distal portion of the apparatus of FIG. 6A;

FIG. 6B shows the graft piercing members penetrated through the vein graft and securing the graft to the apparatus;

FIG. 6C shows the graft-device combination of FIG. 6B positioned above an opening formed in an artery with the piecing member carrying arms urged radially inward, e.g., by a surgeon's fingers (not shown), to a position to facilitate introduction through the opening;

FIG. 6D shows the graft-device combination of FIG. 6C being introduced through the artery opening of FIG. 6C;

FIG. 6E shows the graft-device combination of FIG. 6D positioned in the desired location below the inner wall of the artery with the arms radially expanded to urge the everted portion of the graft against the artery to form a seal therewith;

FIG. 6F shows the graft-device combination of FIG. 6E with the graft piercing members partially penetrated into the artery to seat the piercing members into the aortic wall and secure the graft to the artery and fasteners being positioned in the space between adjacent arms to fixedly secure the graft to the artery;

FIG. 6G shows the fasteners in place and the piercing members retracted into the arms to facilitate removal of the anastomosis apparatus;

FIG. 6H shows removal of the anastomosis apparatus;

FIG. 6I is a partial sectional view of the anastomosis of FIG. 6H;

FIG. 6J is a view of the anastomosis shown in FIG. 6I taken along line 6J-6J;

FIG. 6K is a view of another anastomosis configuration made with the device of FIG. 5A; and FIG. 6L is a view of the anastomosis shown in FIG. 6L taken along line 6L-6L;

FIG. 7A depicts another embodiment of an anastomosis apparatus of the present invention illustrating a mandrel or slide for radially expanding the piercing member carrying arms;

FIG. 7B is an enlarged partial sectional view of the apparatus of FIG. 7A taken generally along line 7B-7B;

FIG. 7C shows the apparatus of FIG. 7A in a radially collapsed state with the mandrel or slide retracted allowing the arms to progressively move radially inward along the distal portion thereof;

FIG. 7D shows the apparatus of FIG. 7A in a radially expanded state with the mandrel longitudinally extended toward the distal end of the apparatus urging the arms radially outward;

FIG. 8A is a perspective view of a ring embodiment of the invention; and

FIG. 8B is a sectional view of the apparatus of FIG. 8A taken along line 8A-8A;

FIG. 8C is a top plan view of the ring embodiment of FIG. 8A;

FIG. 9A illustrates yet a further embodiment of the invention where each graft piercing member and fastener are integrally coupled;

FIG. 9B illustrates the device of FIG. 9A with the plunger moved forward and the piercing members deployed;

FIG. 9C shows the apparatus of FIG. 9A with a graft everted over the graft piercing members;

FIG. 9D shows the graft and device of FIG. 9C positioned within an opening in a target vessel (e.g., an aorta) with the everted portion of the graft sealingly engaging the portion of the target vessel surrounding the opening and with the graft piercing members being drawn through the target vessel wall to position and release the fasteners at the desired site;

FIGS. 10A-D diagrammatically illustrate delivery and deployment of a piercing member with the apparatus of FIG. 9A where:

FIG. 10A shows the graft piercing member prior to piercing a graft that has been everted over the distal ends of the arms shown in FIG. 9A;

FIG. 10B illustrates the graft piercing member passed through the graft and positioned beneath the inner wall of the target vessel;

FIG. 10C illustrates the piercing member penetrated through the target vessel; and FIG. 10D illustrates the piercing member fully released so that it can be fully drawn through the target vessel wall to position the fastener as shown for example in FIG. 2C-2G or 6F-6L;

FIG. 11A is a partial cross-sectional view of a further embodiment of the invention showing the graft piercing member in a retracted state and FIGS. 11A, 11B, 11C, 11D, 11E, and 11F show the apparatus used in an anastomosis where:

FIG. 11A shows the apparatus positioned above an opening in a target vessel;

FIG. 11B shows the apparatus of FIG. 11A with the graft piercing members extended through the graft prior to insertion through the target vessel opening;

FIG. 11C shows the apparatus of FIG. 11B positioned within the opening of the target vessel;

FIG. 11D shows the apparatus of FIG. 11C partially retracted so that the piecing members pass through the wall of target vessel adjacent to the opening therein;

FIG. 11E shows the apparatus arms being retracted to release the piercing members; and FIG. 11F shows release or separation of the piercing members and their return to their memory shape;

FIG. 12A is a partial sectional view of another embodiment of the invention;

FIG. 12B is a transverse sectional view of the apparatus of FIG. 12A taken along line 12B-12B;

FIG. 12C illustrates a shape memory graft piercing member used in the apparatus of FIG. 12A and shown in its closed memory set configuration;

FIG. 12D is an elevational view of the graft piercing member carrying member where the orientation in FIG. 12D corresponds to that of FIG. 12A;

FIG. 12E is another view of a section of the member illustrated in FIG. 12D rotated 90 degrees;

FIG. 12F is a partial perspective view of the embodiment of FIG. 12A showing the proximal portions of the arms coupled to the housing of the apparatus and the proximal ends of the locking members extending therefrom;

FIGS. 13A, 13B, 13C, 13D, and 13E illustrate the operation of the apparatus of FIG. 12A where:

FIG. 13A shows a graft everted over the distal end of the device;

FIG. 13B shows the piercing member partially passed through the graft prior to insertion in a vessel opening;

FIG. 13C shows the device of FIG. 13B after being inserted through the vessel opening and then retracted so that the piercing member engages or passed through a portion of the vessel wall adjacent or surrounding the opening;

FIG. 13D shows retraction of the piercing member holding device and pusher for release of the piercing member; and FIG. 13E shows the piercing member released and in its closed memory shape securing the graft to the vessel;

FIG. 14A is a partial cross-sectional view of yet another embodiment of the invention;

FIG. 14B illustrates the apparatus of FIG. 14A rotated 90 degrees;

FIG. 14C illustrates release of the graft piercing member from the apparatus of FIG. 14A;

FIG. 15A illustrates the apparatus after a graft is everted over the arms of thereof, the graft piercing members have been sufficiently extended to pierce the graft, and the apparatus has been partially retracted so that the distal ends of the piercing members have passed through the target vessel wall adjacent to the opening; and FIG. 15B illustrates release of the graft piercing members from the apparatus of FIG. 15A.

DETAILED DESCRIPTION OF THE INVENTION

Figure 6K:
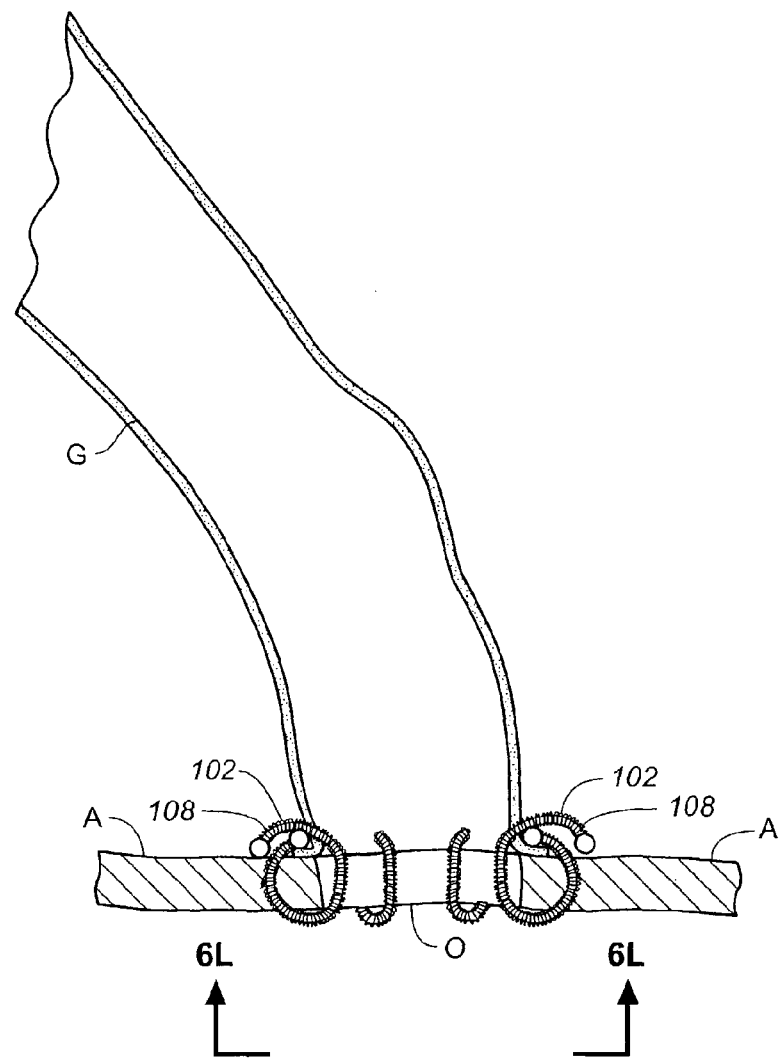

Before the present invention is described, it is to be understood that this invention is not limited to particular embodiments or examples described, as such may, of course, vary. Further, when referring to the drawings, like numerals indicate like elements.

The devices, systems, and methods described herein can be used to connect or anastomose tubular structures or conduits together. The tubular structures can be vascular or nonvascular structures. The illustrative embodiments will be described in connection with coronary artery bypass grafting procedures during which a vascular conduit or graft structure, such as a vein (e.g., a saphenous vein), artery (e.g., an internal mammary artery), or an artificial conduit or graft structure, is anastomosed to an aorta, the example target structure. It should be understood, however, that the invention can be used in other applications not specifically described herein. For example, the devices also can be used to anastomose internal mammary arteries to coronary arteries, and saphenous veins to coronary, femoral or popliteal arteries. As noted above, the devices described herein also can be used to connect other body lumens including nonvascular lumens, which can include, but are not intended to be limited to, the bile duct, the urethra, the urinary bladder, intestines, esophagus, stomach, and bowel.

The devices illustrated in FIGS. 12A-E, 13A-E, 14A-C, and 15A and B also can be used to connect a generally circular object, such as a valve prosthesis, to an anatomic structure, such as a valve annulus. In the valve case, the piercing members are passed through the outer annular portion or the sewing cuff of a valve prosthesis instead of an everted graft. The piercing member-valve prosthesis combination is then introduced through the space inside a patient's valve annulus and the piercing members positioned beneath the valve annulus. The device is then retracted so that the piercing members pass through the valve annulus where they are released to secure the prosthesis to the annulus.

FIGS. 1-4, illustrate anastomosis apparatus and methods described and claimed in co-pending and co-owned U.S. patent application Ser. No. 10/340,164, filed on Jan. 10, 2003, and entitled Anastomosis Apparatus and Methods. Referring to FIG. 1A, an anastomosis device is shown and generally designated with reference numeral 200. Anastomosis device 200 comprises proximal member or portion 202 and distal member or portion 204. More specifically, anastomosis device 200 can comprise separate distal or proximal members or sections, which in turn are coupled together. Alternatively, the device can comprise a single, unitary construction including proximal and distal portions 202 and 204. For purposes of example, sections or portions 202 and 204 can meet along phantom line 205.

Proximal section or portion 202 is configured and constructed to receive a tubular graft structure therein as shown in FIG. 1B. Accordingly, section or portion 202 can be cylindrical as shown in the drawings or it can have other shapes suitable for the intended purpose. For example, section or portion 202 can have a rectangular or oval configuration. Other construction examples include, but are not limited to, mesh tubes, wire framed constructions, or other non solid wall constructions.

Distal end section or portion 204 has a plurality of arms (or fingers) 206 that are configured to hold the everted portion or flap "E" of a tubular graft structure "G" as shown in FIG. 1B. It is important that the adjacent arms are configured and arranged to form spaces, such as spaces 208, suitable for receiving surgical fasteners therethrough as will be described in more detail below. For example, it will be appreciated that the spaces or slots formed between the arms should extend to and be open at the terminus of the distal section or portion 204 of the device to facilitate removal of the anastomosis device after securing the tubular structures together. The arms also are shown as forming an annular member having a circumference formed by the circumferentially spaced arms.

In the embodiment shown in FIG. 1A, tissue or graft piercing members 210 are secured to the ends of arms 206 to enhance the connection between graft structure "G" and distal section or portion 204 of anastomosis device 200. In addition to assisting with everting the graft over the device and/or securing the graft to the anastomosis device, the piercing members or spikes can maintain the position and orientation of the graft on the device. This can assist the surgeon in accurately positioning the graft at the anastomosis site. For example, the surgeon can arrange the graft on the device in a predetermined manner to line up the spaces between the arms of the anastomosis device with portions of the tissue adjacent to opening "O" that the surgeon prefers to place the fasteners. Indicia or a mark can be provided on one or more arms of the anastomosis device or along another portion of the device to provide an alignment mechanism to align the device and graft with the desired portion of the target vessel. Referring to FIG. 2C, the piercing members or spikes can be arranged so that they can be introduced into opening "O" and serve as a locator for the center of opening "O." Alternatively, the piercing members or spikes can be arranged in a generally circular configuration having a larger diameter than that shown in FIG. 2C and larger than that of opening "O" so that the piercing members or needles can be used to penetrate the aortic tissue adjacent the opening. This minimizes or eliminates relative movement between the graft and target vessel, which can be advantageous when introducing the fasteners. When it is desirous to use the piercing members to secure the device to the target vessel, the piercing member length can be selected so as to pass through the entire vessel wall. Alternatively, the piercing member length can be selected so as not to pass through the entire vessel wall, which can be desirable to minimize or eliminate the risk of dislodging material from the interior wall of the target vessel (e.g. the interior wall of an aorta).

Returning to FIGS. 1A and 1B, piercing members 210 and arms 206 are shown parallel to the longitudinal axis or center line "L" of anastomosis device 200. However it should be understood that piercing members or spikes 210 may be arranged in other ways that also desirably hold the everted portion of graft "G." For example, the piecing members may curve outwardly.

Although advantages of the piercing members or spikes have been described above, it should be understood that the anastomosis device can be made with or without the piercing members or spikes on the distal end or portion of the device. Referring to FIG. 1C, another anastomosis device is shown where the aforementioned piercing members or spikes are not used. This device, generally indicated with reference numeral 300, is the same as anastomosis device 200 with the exception that it does not include the piercing members or needles. That is, distal member or portion 204' nor arms 206' have piercing members. Otherwise, they are the same as distal member or portion 204 and arms 206 of device 200.

In yet a further embodiment, which also does not include piercing members or needles, the arms can be configured to enhance the connection between the everted portion of the graft structure and the anastomosis device. Referring to FIGS. 1D and 1E, a further embodiment of an anastomosis device, generally indicated with reference numeral 400, is shown. Anastomosis device 400 is the same as anastomosis device 300 with the exception that arms 206' are replaced with arms 206." Arms 206" extend from proximal member or portion 202 and then curve toward each other and then away from each other in a radial direction to form depressions 407 in distal member or portion 204" or a necked down or reduced diameter section of the collective arm arrangement, which can form part or all of distal member or portion 204". In other words, the arms can be arranged in a circular or annular fashion and each arm curved or bent radially inward and then radially outward in the direction taken from the proximal member or portion to the distal most portion of the distal member or portion to form inwardly curved regions or depressions 407.

Referring to FIGS. 1F and 1G, another embodiment of an anastomosis device is shown. Anastomosis device 500 is similar to anastomosis device 200, but it has a much lower profile. The low profile gives the surgeon the ability and space to manipulate the graft for ease of suturing and/or placement of surgical clips.

Anastomosis device 500 generally comprises an annular ring having a proximal portion 202' and a distal portion 204''', which has a plurality or arms 206''' that are arranged to form spaces or slots 208'. The graft is inserted through the opening or hole in the ring and everted around the side of the ring as shown in FIG. 1G. The slots or openings 208' facilitate passing fasteners or surgical clips therethrough and through the tubular graft structure and tubular target structure in the same manner as spaces or slots 208. It should be noted, however, one feature of the ring is that the spaces or slots are arranged around the perimeter of the ring extend radially inward a length that is greater than the distance they extend longitudinally. This can improve the ease of placement of the sutures or surgical clips through the everted graft and aorta. Anastomosis device 500 also can include piercing members or graft gripping needles 210 (FIG. 1G) to assist with the eversion or placement of the graft as described above. In addition, the piercing members or needles can be shortened or rearranged as noted in the foregoing description. Further, device 500 can be modified so as need not include such piercing members or needles if desired.

Other combinations of differently configured or arranged arms with or without piercing members or needles that would be apparent to one of skill in the art can be used. For example, the arm configuration shown in FIGS. 1D and 1E can be provided with graft piercing members or needles.

Regarding the embodiments illustrated in FIGS. 1A-E, the anastomosis device can be made from suitable plastic or metal. For example, the device can be made from ABS plastic material or stainless steel tubing such as 304 stainless steel tubing. The length of the device typically ranges from about 25 mm to about 125 mm depending on the application. In aortic applications, it typically ranges from about 25 mm to about 70 mm. The inner diameter of the tube typically ranges from about 1 mm to about 25 mm also depending on the application. For example, the inner diameter typically can vary from about 3 mm to about 6 mm when sized for an aortic anastomosis where the tube thickness can range from 0.1 mm to 2 mm. On the other hand, the tube inner diameter can be up to about 25 mm when sized for applications concerning the bowel. The tube can have any number of slots or openings, but typically will have 4 to 12 slots cut into its side or the number of arms selected and arranged to form 4 to 12 openings. The slots or openings typically extend a length of about 2 mm to about 25 mm and have a width of about 0.2 mm to about 5 mm. In aortic applications, the slot length typically can range from about 5 mm to about 25 mm and the slot width typically can range from about 0.2 mm to 2.5 mm. The desired number of sutures or clips to be used for a particular anastomosis can determine the number of spaces or slots that the anastomosis device should have. That is the number of openings can match the number desired fasteners. However, it should be understood that the number of openings need not necessarily match the number of fasteners. The spikes can protrude from the arms or slotted end of the device and extend a length of about 0.5 mm to 15 mm depending on the application. For example, they typically extend 0.5 to 6 mm for aortic anastomosis applications.

The tube can be split down the side to facilitate its placement in and removal from the tubular graft structure. Regarding the former, the split allows the tube to be compressed and deformed to fit into small openings in the target vessel. On the other hand, the split can be expanded to assist in removing the graft from the device. The tube can comprise or be made of shape memory material or alloy so that the compressed split tube returns to a shape memory tubular shape that is approximately equal to or slightly larger the opening into which it is inserted. The tube construction of FIG. 1A, typically would be capable of some elastic deformation in the radial direction if radially compressed so that its annular dimension can be decreased to some degree, which can be desirable when introducing the device into an opening formed in a vessel where the opening is slightly smaller in diameter than the diameter of device 200 in the uncompressed state. The wall thickness can be selected (e.g., reduced) to provide such elastic deformation. Other factors that can be used to achieve this effect include, but are not limited to a slot number, slit width, and material selection as would be apparent to one of skill in the art. For example, the tubular member can comprise or be made of nitinol.

Anastomosis device 500 also can be made of plastic or metal as described above in connection with the embodiments of FIGS. 1A-E. Further, it can be formed with a slit formed through the device in a longitudinal direction as described above. It also may be formed to have two or more parts for ease of removal once the anastomosis is complete. The parts can be held together through tongue and groove or pin and hole mechanisms as would be apparent to one of ordinary skill in the art. Other connecting mechanisms can be used as well. It is also possible to rely on the graft hold the parts together after it has been positioned on the device as shown in FIG. 1F. The height of the device typically will vary from about 1 mm to 25 mm depending on the application (e.g., the height will typically range from about 1 mm to 5 mm when constructed for aortic anastomosis applications. The inner diameter of the device opening will be the same as devices 200, 300, and 400 and will range from about 1 mm to about 25 mm in general and about 1 mm to 6 mm in aortic applications. The number of the spaces or slots is selected as in the case of devices 200, 300, and 400. The depth of the spaces or slots in a radial direction will vary from about 2 mm to about 20 mm. The width of the crown (top surface of the proximal end extending between the center hole of the device and the inner perimeter of the openings or slots) ranges from about 2 mm to about 10 mm. It also is noted that although a keyhole configuration of the openings or slots is shown, other configurations can be used such as, for example, a straight slot or opening.

The outer surface of the anastomosis device, upon which the everted portion of the graft is supported, has a length in the axial or longitudinal direction of at least 2 mm (preferably at least 4 mm in aortic applications, in order to sufficiently secure the graft to the device when graft piercing members or needles are not used.

As is apparent from the foregoing description, the anastomosis device can be used to hold one end of a graft over an opening in an aorta, while fasteners such as sutures or surgical clips are used at the sites where the spaces are positioned to complete an anastomosis. The anastomosis device can be sized so that the graft forms a seal with the aortic opening, thereby allowing surgeons to perform an aortic anastomosis without the use of a clamp such as a side-biting clamp. Referring to FIGS. 2A-2G and the embodiment shown in FIGS. 1A and 1B, a method of performing a proximal anastomosis where one end of a tubular graft structure "G" is anastomosed to the aorta "A" of a patient will be described. Although not described in detail in the following example, the other end of the graft is anastomosed to one of the patient's coronary arteries. It also should be understood that the following example is provided only for purposes of illustration.

A tubular graft structure "G" is selected and prepared as is known in the art, and then introduced through the anastomosis device to a position as shown in FIG. 2A. The tubular graft structure is then everted over the spikes, piercing members, or graft positioning members 210 as shown in FIG. 2B. If the distal anastomosis (i.e., the anastomosis between the other end of the tubular graft structure "G" and a target coronary artery) has not yet been performed, then cross-clamp "C" is placed on the free end portion of the tubular graft structure as shown in FIG. 1B to prevent blood leaking from the tubular graft structure.

Once this is completed the surgeon forms an opening "O" in the aorta using, for example, a scalpel and an aorta cutting device such as an aortic punch (not shown). It should be understood that other known devices to form the opening also can be used. For example, a cylindrical member with a sharp cutting cylindrical edge with a piercing member positioned therein with an arrow type head to catch the cut tissue can be used. When the aortotomy or opening has been completed, the surgeon removes the cutter or punch and introduces the anastomosis device and graft into opening "O" to form a seal between the graft and target vessel as shown in FIG. 2C. In other words, the anastomosis device with the everted graft is introduced into the opening in the tubular target structure (i.e., into the opening "O" in aorta "A") and held in place to seal the hole or opening. More specifically, the diameter of the distal end or portion 204 of anastomosis device 200 is selected so that when the anastomosis device and graft are inserted into aortic opening "O," the side edge defining the perimeter of the opening compresses against the everted portion of the graft to from an effective seal to minimize or eliminate blood leakage through the seal. If the distal anastomosis was previously completed, blood can flow through the everted tubular graft structure to the coronary artery, thus revascularizing the heart. If not, a clamp "C" can be placed on the graft and removed after the distal anastomosis has been completed.

Alternatively, the piercing members or spikes can be used to tack the anastomosis device in place while the proximal anastomosis is performed. If the piercing members were arranged so as not to fit within opening "O", the surgeon would pierce the outer wall of the target vessel adjacent opening "O" with the piercing members sufficiently to form a seal between the graft and target vessel.

In performing the proximal anastomosis, fasteners such as sutures or surgical clips are passed through the spaces or slots 208, tubular graft structure "G" and the tubular target structure (aorta "A") as shown if FIGS. 2D and 2E. In the procedure depicted in FIGS. 2D-E, a tissue connector assembly 100 having a surgical clip 102, which is releasably coupled to a flexible member or suture 104, which in turn, is coupled to a tissue piercing member 106 is shown. The spaces or slots in the side of anastomosis device 200 facilitate the passing of the needle, suture, and clip combination through the end portion of the tubular graft structure wall, down through aortic opening "O", and then up through the wall of aorta "A" adjacent the opening. After the desired number of fasteners or sutures have been placed, the anastomosis device is retracted and removed form the completed anastomosis site as shown in FIG. 2D. If desired, more sutures or clips can be used to finish the anastomosis. A slight variation on the graft to aorta connection can result when the fastener needle is passed through the flap of the everted portion of the tubular graft structure or the material immediately adjacent to that everted portion as shown in FIG. 2F. In FIG. 2F, only the everted flap of the tubular graft structure is connected to the aorta.

One type of clip that can be used with the anastomosis devices described herein and as shown in FIG. 2C and designated with reference numeral 102 is a self-closing clip. A self-closing clip may be broadly characterized as having two end points which tend to come closer together either by elasticity or so-called pseudoelasticity. The clip may be made by heat-treating a NiTi wire to a certain temperature and time to have a desired undeformed shape (e.g., an undeformed closed or loop configuration). Examples of such clips, including methods of making them as well as materials which may be used, are disclosed in U.S. patent application Ser. Nos. 09/089,884 and 09/090,305 both filed on Jun. 3, 1998; U.S. patent application Ser. Nos. 09/259,705 and 09/260,623 both filed on Mar. 1, 1999; and International Application Nos. PCT/US99/12563 and PCT/US99/12566 both filed Jun. 3, 1999 and published on Dec. 9, 1999 under International Publication Nos. WO 99/62409 and WO 99/62406, respectively, all of which are hereby incorporated by reference herein. In brief, the clips generally comprise a deformable wire comprising shape memory alloy and have a closed configuration and a biased open configuration. That is, one can apply force to the clips to move them to an open configuration. When the force is removed, the clips tend to move back toward their closed configuration.

Clip 102 may be deployed, for example, in the form of a single-arm surgical tissue connector assembly as generally shown in FIG. 3 and designated with reference numeral 100. Tissue connector assembly 100 generally comprises a surgical fastener or clip 102, which is releasably coupled to a flexible member or suture 104, which in turn, is coupled to tissue piercing member or needle 106. In FIG. 3, clip 102 is shown biased to an open U-shaped configuration. This is accomplished by compressing the spring or coil 108, which surrounds clip or clip wire 102. When the coil is compressed, it urges the clip to an open configuration. Clip 102 can have an enlarged portion 110 at its free end to constrain coil 108. Such a tissue connector assembly is disclosed, for example, in the aforementioned International Application No. PCT/US99/12566 from page 10, line 10 through page 11, line 21, which section and its accompanying FIG. 1 is hereby specifically incorporated by reference herein. The other end of clip 102 is configured to releasably engage a release mechanism, which is coupled to suture 104. Thus, the other end of the clip also can have an enlarged portion as will be more fully appreciated after review of the following description.

In the illustrative embodiment, tissue connector assembly 100 includes a release mechanism or device 112 that releases clip 102 when squeezed with a surgical instrument. Such a release mechanism is disclosed, for example, in the aforementioned U.S. patent application Ser. No. 09/260,623 and International Application No. PCT/US99/12566, which claims priority thereto. For the sake of particular example, the release mechanism description in International Application No. PCT/US99/12566 from page 25, line 12 through page 27, line 30 ending with the text "mechanism 23c" (but without the text "such as needle 17 as shown in FIG. 1" on line 27 of page 27) and the referenced figures are hereby specifically incorporated by reference herein. A summary of such a release mechanism is provided below with reference to FIGS. 4A-D.

Referring to FIGS. 4A-D, release mechanism 112 generally comprises a plurality of substantially rigid strands, cables or wires 114, which may be metallic, and which are arranged substantially parallel to one another and circularly about a longitudinal axis. The hidden end portions of the strands are coupled to tapered section "T", which is coupled to a piercing member or needle through a flexible member 104. The strands may be coupled to rod 116, which is fixed to the tapered element. End portions of the strands include notches, which form a chamber 118 for releasably receiving enlarged portion 120 of the clip. According to cited International Application No. PCT/US99/12566, the notches preferably are placed about 0.015 from the free ends of the strands, but this distance can be varied depending upon the desired compression on coil or spring 108. A shrink wrap layer, preferably a shrink tubing 122 as set forth in the cited PCT application is provided around at least the free end portions of the strands and the shrink wrap or tubing heated to compress against the strands and hold them in place against the enlarged wire portion to effectively hold the enlarged portion captive until the shrink wrap is squeezed, the strands displaced and the enlarged portion released.

Although a self-closing clip has been described for purposes of example, it should be understood that other fasteners, including sutures or other fastening mechanisms can be used. For example, clips that require plastic deformation for closure can be used.

Referring to FIGS. 5A and 5B, an anastomosis device is shown provided with a plurality of piercing members slidably mounted along or coupled to the arms of the device in accordance with the present invention. Referring to FIGS. 5A and 5B, one example of such a device is illustrated and generally indicated with reference numeral or apparatus 600. Anastomosis device 600 generally comprises a proximal member or portion 602 and a distal member of portion 604. Proximal member or portion 602 includes a tubular body member 612 having finger grip extensions 614 and an anchor member or disk 616 fixedly secured therein at the distal end of body member 612.

Distal member or portion 602 includes a plurality of arms 606, in which piercing members 610 are slidably mounted. More specifically, each arm forms a pathway in which one of the piercing members is slidably mounted. Piercing members 610 include a proximal portion 610a secured to plunger 612 and a distal portion 610b that has the desired memory shape to pierce the graft and vessel to which the graft is to be anastomosed. In the illustrative embodiment, the piercing members comprise or are made of shape memory material so that the distal portions 610b can be provided with a hook configured memory shape, which is one suitable shape for holding the graft and vessel together during the anasotmosis as will be described in more detail below. As shown in FIG. 5B, the distal portions 610b assume a hook shape when extended from arms 606. One suitable shape memory material for piercing members 610 is nitinol wire.

Arms 606 define or form pathways for the piercing members 610 to move. Accordingly, arms 606 can be tubular members (e.g., hypotubes) each having a lumen through which a piercing member 606 can slide. Arms or tubular members 606 have one end extending through or into anchor or disk 616 and secured thereto. Those ends can be glued to anchor 616 or secured thereto by other suitable means. For example, threaded bores can be formed in anchor 616 and the proximal ends of tubular members or arms 606 threaded so that the arms can be screwed into the anchor.

As shown in FIGS. 5A and 5B, piercing members 610 pass through arms or tubular members 606 and anchor 616 and extend along the outer surface of the cylindrical portion of plunger or actuator 618 where the proximal portions 610a of the piercing members are secured to the plunger. The cylindrical portion of the plunger can be provided with grooves in its outer surface for receiving proximal portions 610a of the piercing members, which can then be glued in grooves or secured therein by other suitable means.

Returning to arms or tubular members 606, arms 606 can be secured in anchor 616 so as to be parallel to one another, diverge in a direction away from the anchor 616 or proximal portion 602 (FIGS. 5A & 5B), or converge or tend to move toward union in a direction away from the anchor (FIGS. 7A-D) and may or may not contact each other at their distal ends.

Referring to FIGS. 5A and 5B, tubular members or arms 606 are secured to anchor 616 so as to diverge in a direction away from the anchor. One can describe the arms a being biased radially outward. This configuration provides a larger range of adjustment of the annular dimension of the arms taken collectively along their distal end portions as compared to the split tube configurations described above. That is, the surgeon has more flexibility in being able to use the same device for a larger range of openings formed in the second tubular structure to which the first tubular structure is attached. The surgeon can squeeze the arms so as to move them radially inward (the radially direction being generally indicated with reference character "r" in FIG. 5C, which shows a radial direction being one that goes from center "c" to arm 606, is to be applied to all embodiments described herein with the exception of that shown in FIGS. 8A-C) to fit the distal ends of the arms in the opening in the target structure or vessel. Once the distal portions of the arms are in the opening, the surgeon can release the arms to allow them to move or tend to move radially outward and urge the portion of the graft, which is everted over the distal ends of the arms, against the tissue surrounding the opening. This can enhance the seal between the graft and second tubular structure or vessel as will be further described below.

FIGS. 6A-L diagrammatically illustrate a method of performing a proximal anasotmosis using the apparatus of FIG. 5A. Referring to FIG. 6A, a graft (e.g., vein graft) is passed between two of the arms 606 and its end everted over the distal portions of all of the arms 606 of apparatus 600. Once the graft is everted, the actuator or plunger 618 is pushed forward (FIGS. 5A & B) to extend the distal end portions 610b of piercing members 610 out from arms 606 and through the everted portion of the graft, thereby securing the graft to device or apparatus 600 and holding the graft in place as shown in FIG. 6B. As shown in FIG. 6B, distal portions 610b have a hook or U-shaped memory shape. Referring to FIG. 6C, device or apparatus 600 is positioned above an opening "O" formed in an artery, such as aorta A, with the piecing member carrying arms urged radially inward, e.g., by a surgeon's fingers (not shown), to a position to facilitate introduction through the opening. Alternatively, a cylindrical tube ("T") can be slidably radially inward as shown in phantom in FIG. 6C. It should be understood, however, that tubular body 612 and cylindrical tube T need not be concentric, nor does tube T need to be cylindrical. The graft-device combination of FIG. 6C is then introduced through the artery opening "O" as shown in FIG. 6D.

Figure 6L:
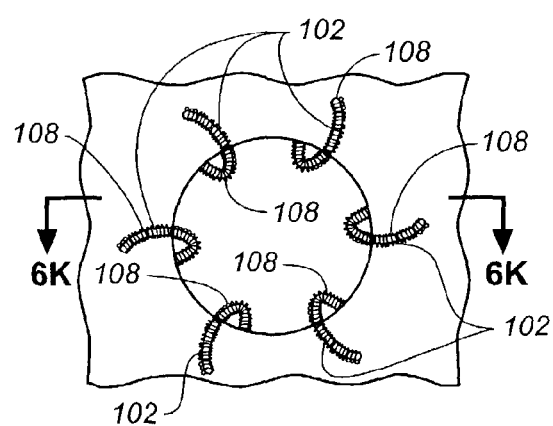

The graft-device combination of FIG. 6D is positioned in the desired location below the inner wall of the vessel (e.g., artery "A") and the arms allowed to radially expand and urge the everted portion of the graft against the vessel (e.g. Aorta "A") to enhance the seal therewith as shown in FIG. 6E. The entire device is then retracted to seat the distal portions 610b (hooks) of piercing members 610 against the second tubular structure (e.g., aorta "A") and seat the hooks into the vessel to secure the graft in place. With the graft piercing members so seated, fasteners or sutures are placed between adjacent arms to fixedly secure the graft to the second tubular structure (e.g., aorta "A") as shown in FIG. 6F where fastener assemblies 100 are used to deploy fasteners 102, which are shown surrounded by coils 108 and which fasten the first and second tubular structures (e.g., graft "G" and aorta "A"). Once the anastomosis is completed (FIG. 6G), the piercing members are retracted and device 600 removed (FIG. 6H). The anastomosis is further illustrated in FIGS. 6I and 6J. FIG. 6K is a view of another anastomosis configuration made with the device of FIG. 5A and FIG. 6L is a view of the anastomosis shown in FIG. 6K taken along line 6L-6L.

FIG. 7A depicts another embodiment of the invention, which is generally indicated with reference numeral 700. In this embodiment, arms 706 are biased radially inward as compared to the radially outward biased arms 606 in device 600. However, both arms 606 and 706 are otherwise the same and have outer diameters that range from 0.5 mm to 2 mm in, for example, aortic applications. In the illustrative embodiment, anastomosis apparatus 700 includes a mandrel or slide 722 for radially expanding the piercing member carrying or support arms 706 after the device has been placed in the opening in a manner similar to that shown in FIGS. 6C and 6D. Device 700 includes a plurality of arms having a proximal end secured to tubular member or arm support 720 which tapers so that the annular dimension of the arms, taken collectively, progressively decreases in the distal direction when the slide 722 is in a retracted position adjacent to arm support 720 as shown in FIG. 7A. The arms can be secured in the grooves as described above in connection with the securement of arms 606 in tubular body 612. The arms also extend along longitudinal grooves formed in mandrel or slide 722 and can be secured by glue or other suitable means at their proximal end to tubular member 720 as described above in connection with the securement of arms 606. Actuator or plunger 718 extends through the device with its end secured to mandrel or slide 722 so that when the pusher is moved forwardly, it pushes the mandrel or slide 722 distally and expands the arms to enhance or form a seal between a graft and a second tubular structure (e.g., aorta "A") when a graft is everted over the distal portions 710b of piercing members 710, which are similar to piercing members 610, in a manner similar to that shown in FIGS. 6A and B. Proximal portions 710a are secured in grooves formed in cylindrical piercing member support 721, which is slidably mounted on actuator or pusher 718 and secured to cylindrical knob or finger grip 714 by fastener or screw 716 (FIG. 7B). When knob 714 is pushed forwardly the piercing members are extended as shown in FIGS. 7C and 7D. Moving the knob 714 proximally retracts the piercing members as shown in FIG. 7A. Housing or tubular body 712 can have a longitudinal slot 717 through which screw 716 can slide so that knob 714 can move independently from housing 712.

Referring to FIG. 8A, a further embodiment of the invention is shown and generally indicated with reference numeral 800. Anastomosis device or apparatus 800, generally comprises a first or body portion 802, which can have an annular shape and be in the form of a ring, and a second portion comprising a plurality of radially extending arms 806, in which piercing members 810 are slidably mounted. Piercing members 810 like piercing members 610 and 710 comprise or are made of shape memory material such as nitinol with the distal portions 810b having a hook or U-shaped memory shape so that they assume that shape when extended from the arms 806. Further, distal portions 810b can be provided with more curvature than that shown so that they can penetrate the tissue of the target vessel if desired. It also should be understood that other suitable memory shapes can be used for any of the piercing member distal portions 610b, 710b or 810b.

Arms 806 are slidably mounted in body portion or member or ring 802. Piercing members 810 can be moved radially inward or radially outward by moving pusher knob 818, which is fixedly attached thereto, and arms 806 can be moved radially inward or outward by moving members or blocks 820, which are fixedly secured to the arms. With the position of arms 806 being adjustable, the user can control the diameter of the center ring that the piercing members form as shown in phantom with reference number 803 in FIG. 8C. With this construction, one can move the arms radially inward to decrease the diameter of ring 803, which makes it much easier to evert the graft over piercing members 810 when the piercing members are extended from arms 806. Once the grafted is everted and the everted portion placed over the arms and the piercing members passed through the graft, one can retract the arms (move the arms radially outward), thereby expanding the diameter of the center ring 803. This can enhance or form a seal between the graft and target vessel as will be described in more detail below.

The radius of curvature of the memory shaped distal portions of the piercing members can vary. For example, a larger radius of curvature may be desired if the user wants to insert part of the device into the opening in the target vessel. On the other hand, a smaller radius of curvature may be desired if the user wants to tack the device down around the opening in the vessel, thereby seating the device on the outer wall and covering the opening with the graft.

As in the procedures described above, a tubular graft is everted over the inner ends of the arms. In this case, the graft can be introduced through the center of the device and need not pass between arms. The piercing members are passed through everted portion of the graft in a manner similar to that shown in FIG. 6B and the corresponding described thereof. The surgeon then cuts a hole or opening in the target vessel (e.g., the aorta) using a scalpel and an aorta cutting device or punch. When the hole or opening is complete, the surgeon covers the hole with either a finger or other suitable tool. The distal portion of the arms and the portion of the graft everted thereover is positioned in the vessel opening. The arms are retracted to expand the everted graft against the tissue surrounding the opening so as to form a seal therewith. In other words, the arms can be retracted to urge the graft against the tissue surrounding the target vessel opening to seal the connection between the graft and target vessel. The support ring can be moved back or upward to seat the piercing members against the interior wall of the target vessel adjacent the opening. Fasteners, such as suture or clips, are then placed in locations as shown, for example, in FIGS. 6F-6L to secure the graft to the target vessel. The piercing members are then retracted and the anastomosis device pulled off of the graft and target vessel. As in any of the examples described herein, additional fasteners or clips can be placed at the connection, if any blood appears to be seeping out from the graft and target vessel in a manner similar to that shown in the previous embodiments. After the arms and the graft are positioned in the target vessel opening, the arms can be moved radially outward or adjusted to enhance or form a seal between the everted portion of the graft and/or the arms take the form or shape of a target vessel.

According to another embodiment, arms 806 are spring loaded in a retracted state. Referring to FIG. 8B, one spring configuration is shown in phantom with the spring "S" shown in dashed line. In this embodiment, spring S is placed around arms 806 between body portion 802 and a respective block 820. In this case, the graft is everted over the distal ends of the arms and the arms are held in a position where the diameter of center ring 803 is smaller than the diameter of the opening in the target vessel. The device is moved to seat the piercing members in/on the target vessel. The arms with the everted graft is placed in the target vessel opening. Once in place, the arms are released and the springs urge the arms radially outward so that the everted graft and/or the arms take the form or shape of the opening.

The ring embodiment illustrated in FIGS. 8A and B has an advantageous low profile and provides plenty of room to pass a suture needle or clip between arms to complete the anastomosis. The farther away the center ring, which the bend in arms 806 or piercing member exit openings define, is from the outer support member 802, which can be in the form of a ring, the more space is provided. Ring 802 can be a continuous ring or a split ring. It also can be made by joining together one or more pieces of material. One advantage of being a split ring or a ring comprising a plurality of sections, which can be readily broken apart, is that the ring can be easily removed after completion of the anastomosis. With the split ring, the split can be dimensioned so that the graft can pass therethrough. In this manner, the ring can be easily removed when the other end of the graft is connected to other anatomy or structure. The multi-section ring can comprise a plurality of sections where adjacent sections are connected with set screws. The set screws can be easily removed to remove the ring sections from the anastomosis site.

Ring 802 can be made of stainless steel, medical grade plastic such as polyethylene, or other material suitable for the intended purpose. Ring 802 also can have other shapes including but not limited to square, rectangular, elliptical, or oval shapes. Arms 806 can be made from surgical grade stainless steel tubing as well as other suitable materials known to those of ordinary skill in the art. As described above, the piercing members comprise shape memory material such as nitinol.

Referring to FIGS. 9A & B and 10A-D, another embodiment is shown and generally indicated with reference numeral 900. As with the other embodiments described herein, this embodiment can provide an anastomosis (e.g., an aortic anastomosis) without the use of a side-biting clamp. However, in this embodiment fasteners are integrated into the device. This design minimizes or eliminates the need for placing separate fasteners at the anastomosis site.

Referring to FIGS. 9A & 9B, anastomosis device or apparatus 900 includes a proximal or body portion 902 and a distal portion 904. Proximal portion 902 includes an actuator or plunger 918 which is the same as actuator or plunger 618 with the exception that the grooves formed in plunger 918 to receive the proximal portions of actuator members or pusher rods or members 924 can be slightly larger to accommodate pusher rods 924, which can be slightly larger than piercing member end portions 610b diagrammatically shown in FIGS. 5A & B. The pusher rod proximal portions can be secured in surface grooves formed in plunger 918 with glue or other suitable means. Proximal portion 902 further includes tubular body 912, finger grip 914 and disk or anchor 916 which are the same as corresponding elements 612, 614 and 616 of device 600.

Distal portion 904 includes a plurality of arms or members 906 which have proximal portions secured to disk or anchor 916 in the same way that arms 606 are secured to disk or anchor 616. The only difference between arms 906 and 606 is that arms 906 have longitudinal slots 907 formed in the distal end portions thereof. As shown in the drawings, slots 907 extend to the distal ends of arms 906 and are open at the distal ends of the arms.

Apparatus or device 900 further includes a plurality of fasteners releasably coupled to actuators 924 and arms 906. In the illustrative embodiment, the fasteners can part of an assembly. One suitable assembly, which is shown in FIGS. 10A-10D, for example, and generally designated with reference numeral 100'. Tissue connector assembly 100' is the same as tissue connector assembly 100 (FIG. 3) with the exception that piercing member or needle 910 has a different configuration than piercing member or needle 106 and piercing member 910 is coupled to suture 104 in a manner that differs from the coupling between piercing member 106 and suture 104. Tissue connector assembly 100' generally comprises surgical clip or fastener 102, which comprises a wire including an enlarged portion 110, coil 108, which surrounds clip 102, release mechanism 112, and suture 104, where release mechanism 112 has one portion releasably coupled to clip 102 and another portion coupled to suture 104 as described above in connection with tissue connector assembly 100. The other end of suture 104 is coupled to piercing member or needle 910 as shown, for example, in FIG. 10A-D where the suture is inserted into a bore formed in the piercing member and the piercing member crimped to secure the suture therein. Therefore, release mechanism, which can be referred to as a coupling, releasably couples the surgical fastener to the suture and piercing member. Suture 104 passes through slot 907 and slides therealong as the piercing member is ejected as will be described in more detail below.

In order to keep the piercing member from sliding out through slot 907, it can be moved some angular distance therefrom. The slot also can be formed to have a width less than the width or diameter of the piercing member.

Referring to FIGS. 10A & B, piercing members 910 can be formed from wire comprising shape memory material such as nitinol. Piercing member 910 is formed to have a hook or U-shaped memory set configuration as shown in FIG. 10B and an open configuration as shown in FIG. 10A, where the piercing member is deformed to a shape suitable for sliding in arm 906. Each piercing member 910 has a distal end with a sharp tip and a proximal end portion with a notch 910N formed therein and a lip 910L. Each pusher 924 has a notch 924N and lip 924L configured to mate with a corresponding notch 910N and lip 910L of a respective piercing member 910. The pusher can be a solid or tubular wire having an outer diameter larger than that of the piercing member with which it is to cooperate, and slightly smaller than that of an arm 906 in which it is slidably disposed.

When any one of the piercing members 910 is inside a respective arm 906, the notched pusher and piercing member mate so that they will move in concert. Thus, if the pusher is further retracted, the piercing member will be carried therewith (i.e., further retracted). This feature can be used to position the piercing members within arms 906 as shown in FIGS. 9A and 10A, for example, so that a graft can be everted over the distal ends of arms 906 without catching on the distal ends of the piercing members. FIG. 10B shows the pusher 924 moved distally to sufficiently extend the piercing members from the distal end of the arms to return to its hook configured memory shape. When a graft "G" is everted over the distal ends of arms 906 with the distal ends of the piercing members retracted as shown in FIG. 10 A, one can push plunger 918 forward so that the pusher members 924 push the piercing members distally a distance sufficient to penetrate through graft "G" and return to their hook configured memory shape as shown in FIG. 10B. Each everted area effectively becomes a bite on the graft. As long as the connections between the pushers and piercing members 910 or the mated region of the pushers and piercing members 910 are within arms 906, the hook shaped piercing members cannot be separated from the pusher members or arms. It is in this position that apparatus or device 900 is retracted to pass the distal ends through the target vessel such as aorta "A" (FIG. 10C). Once the piercing members have penetrated the target vessel as shown in FIG. 10C, the pusher can be moved further distally to disengage the pusher members 924 and piercing members 910 to release the piercing members as shown in FIG. 10D. The piercing members can be released simultaneously with a single actuator plunger as shown or they can be released individually. In the latter case, the anastomosis device 900 is constructed with a separate actuator 918 and pusher member 924 associated with each arm 906 and tissue connector assembly 100'. Once the piercing members have been released, they are pulled to position the fasteners or surgical clips of tissue connector assemblies 100' so that a portion of the graft and target vessel are inside the clip (see the center clip FIG. 9D). When a portion of the graft and target vessel are positioned within the surgical fastener, release mechanism 112 is actuated to release the surgical fastener from the suture and piercing member (see the clip at or near the 3 o'clock position in FIG. 9D). After all of the surgical fasteners are in place in the illustrative embodiment, the anastomosis has at least an adequate temporary seal so that arms 906 can be removed from the anastomosis site before adding more fasteners complete the anastomosis. In an aortic anastomosis, 8-10 fasteners typically are sufficient to effectively secure the graft to the aorta and maintain a hemostatic seal therebetween. Accordingly, if the device has 8-10 arms (i.e., arms 906), one may not need additional fasteners. However, if there are 5 arms as shown in the FIGS. 9A-D, it is typically desirable to add 3 to 5 more fasteners such as fasteners 102. One advantage of this embodiment is that arms 906 can be removed from the site before placing one or more of the additional fasteners to complete the anastomosis.

Apparatus 900 is made the same way as apparatus 600 with the exception that the arms have a slot 907 formed therein and piercing members 610 are replaced with a two part system including actuator or pusher arms and tissue connector assemblies 100'. The pusher arms can be made of any suitable wire or hypotube (e.g., the pusher arms can be made from stainless steel wire having a diameter of about 0.2 mm to 3 mm. A notch is formed the wire or hypotube as shown in FIGS. 10A-D. The piercing members comprise shape memory material such as nitinol and in the illustrative embodiment are formed with a hook configured memory shape. The piercing members also have a notch formed therein as shown in FIGS. 10A-D where the piercing member and pusher member notches are dimensioned to mate with one another. The notch can be made in the same manner as the notch formed in the pusher arms or members. Each slot 907 that is formed in each arm 906 starts at the distal end of a respective arm. Each slot has a length that is as long as a respective piercing member when the piercing member is deformed into the shape shown in FIG. 10A where the piercing member is retracted into a respective arm. The notches and slots can be formed using standard dicing, electro-discharge machining (EDM), or laser cutting techniques.

A method for using apparatus 900 to anatomose a vein graft to an aorta will be described for illustrative purposes only. As set forth above, the apparatus can be used in many other applications, examples for which have been provided.

A vein, such as a saphenous vein is harvested from the patient and prepared for anatomosis to the target vessel. With the piercing members 910 in a retracted state as shown in FIG. 9A, the vein graft is everted over the distal ends of arms 906. The amount of graft everted should be equivalent to a normal bite size 6 taken on the vein graft for a traditionally completed anastomosis using a continuous suture. Plunger 918 is then pushed forward a distance sufficient to extend piercing members from arms 910 and through the everted graft as shown in FIG. 9C. The vein graft is completely pulled over the piercing members, which have returned to their set hook shaped memory shape. The vein graft should pass over the piercing members and be in contact with arms 906. The apparatus having the vein graft mounted thereon is ready for placement into the aortic opening to facilitate anastomosing the graft to the aorta as shown in FIG. 9D. The placement steps are described in more detail below with reference to FIGS. 10A-D.

The surgeon then forms a hole or opening in the wall of the aorta. This can be done with a scalpel and an aortic punch or an all-in-one punch or coring device as is known in the art. As the punch or coring device is removed, arms 906 of apparatus 900 are compressed radially inward in a manner similar to that shown in FIGS. 6C and D to facilitate introduction through the aortic opening. Once the hook shaped portions of the piercing members are inside the aorta, the arms are allowed to return toward their relaxed state so that they fill the opening and urge the everted portion of the vein graft against the tissue surrounding the opening in a manner similar to that shown in FIG. 9C. Apparatus 900 is then pulled upward so that the piercing members are seated against the inner wall surface of the aorta. Apparatus 900 is further pulled upward or otherwise retracted from the anastomosis site so that the piercing members penetrate the aorta as shown in FIG. 10C and a seal between the everted portion of the graft and the tissue surrounding the opening is achieved. Plunger 918 is moved forward further until the piercing members are released from actuator arms or members 924 and arms 906. Piercing members 910 can be released simultaneously or individually as described above. The distal end of each piercing member is gripped with any suitable means such as a forceps and pulled to seat the surgical fasteners or clips of tissue connector assemblies 100' so that portions of the everted graft and artery are disposed therein (FIG. 9D). Release mechanism 112 is squeezed to release the surgical fasteners from the release mechanism and allow the fasteners to return to or assume their loop configured memory shape (FIG. 9D). After all of the fasteners have been released, the apparatus (now without fasteners) is removed from the anastomosis site. Additional fasteners or individual sutures can be used to complete the anastomosis as needed. For example, additional fasteners 102 can be delivered using tissue connector assemblies 100. As noted above, typically 8-10 fasteners are sufficient in an aortic anastomosis.

Although apparatus 900 has been illustrated with a particular piercing member delivery configuration, it should be understood that other configurations can be used as well. For example, the piercing member delivery system shown in FIG. 7A can be used. In this case, the piercing members 710 are replaced with actuators 924 and tissue connector assemblies 100' and arms 706 are replaced with arms 906 so that the arms have longitudinal slots that allow sutures 104 to pass therethrough and slide therealong.

Referring to FIGS. 11A-F a further embodiment is shown and generally indicated with reference numeral 1000. As with the other embodiments disclosed herein, apparatus 1000 facilitates an anastomosis, such as a proximal anastomosis, without the use or need of a side-biting clamp. Apparatus 1000 is the same as apparatus 900 with the exception that each piercing member is directly secured to an actuator or pusher arm. That is, this embodiment does not incorporate a tissue connector assembly 100'. Instead, apparatus 1000 includes a plurality of arms 1006 and a plurality of piercing members 1010 and actuator or pusher members 1024 secured to one another and slidably disposed in arms 1006.

Although only two arms are shown for purposes of simplification, it should be understood that generally five to twelve arms are used. Further, although the entire delivery system also is not shown in FIGS. 11A-D for purposes of simplification, it should be understood that apparatus 1000 can incorporate the delivery system or mechanism of apparatus 900, including the tubular body or housing 912, finger grips 914, disk or anchor 916 to which arms 1006 are attached, and plunger 918 to which actuator or pusher arms are attached. Further, arms 1006, which are without slots, would replace arms 906. Alternatively, arms 1006 and actuator or pusher members 1024 can be incorporated into the delivery apparatus shown in FIGS. 7A-D. In this case, each actuator or pusher member 1024 and piercing member 1010 combination replaces each piercing member 710. In yet a further variation, apparatus 1000 can be modified to incorporate the delivery system or mechanism of apparatus 800, including body portion 802, arms 806, knobs or actuators 818, and blocks 820. In this case, pusher members 1024 and piercing members 1010 replace piercing members 810 of apparatus 800.

Each piercing member 1010 is made from shape memory material, such as nitinol, and formed so that at least a portion moves from its deformed, straightened shape to its loop memory shape when extended from its respective tubular constraint (i.e., arm 1006). Piercing members 1010 can be formed in the same way that surgical clips 102 are formed with the exception that the distal end portions 1010b of the piercing members are formed with a sharpened end and the proximal end portions 1010a are made suitable for being fixedly attached to actuator or pusher members 1024. That is the proximal ends of piercing members 1010 can secured to the distal ends of pusher arms 1024 by welding. Alternatively, the proximal ends of piercing members 1010 and the distal ends of pusher arms can be provided with mating threads to provide a screw connection. In a further alternative, the pusher arms and piercing members can be formed from the same member with a step transition between the pusher arm and piercing members.

In using apparatus with the delivery system of FIGS. 9A and B, the surgeon prepares the graft as known in the art and everts the graft over the distal ends of arms 1006 as described above and further shown in FIG. 11A. The distal end portions 1010b are extended through the graft and sufficiently beyond the arms 1006 so that the portion extending beyond arms 1006 assumes a U-shaped or hook shaped configuration (FIG. 11B). The surgeon cuts a hole in the target vessel (e.g., aorta) and covers it as described above. Forcing the arms 1006 radially inward as necessary, apparatus 1000 is then placed in the hole or opening in the target vessel (FIG. 11C). Once inside the target vessel, arms 1006 are allowed to expand and fill the opening. The apparatus is retracted to seat the piercing members against the inner wall of the target vessel (e.g., the aorta). The apparatus is then further retracted so that the piercing members pass through the target vessel tissue surrounding the opening as shown in FIG. 11D and a seal between the everted portion of the graft and tissue surrounding the opening is achieved.

After the piercing members have penetrated the target vessel wall, the plunger is further advanced forwardly while the entire apparatus is retracted so that further lengths of the piercing members are extended beyond the distal ends of arms 1006 without disturbing the position of the hook shaped portion of the piercing members in the target vessel wall or without forcing the end portions of the piercing members downwardly and out of the target vessel wall (FIG. 11E). The surgeon then cuts the piercing members at a location near the distal ends of arms 1006. The cuts are made at a location that allows sufficient length of the piercing member to remain at the anastomosis site to form a loop as it returns to its memory shape (FIG. 11F) to hold the everted portion of the graft to the target vessel and complete the anastomosis. Accordingly, the cut distal portions of piercing members 1010 also function as surgical clips. If some leakage appears, sutures or fasteners, such as fasteners 102, can be placed at the area of concern.

Referring to FIGS. 12A-E and 13A-E, a further embodiment is shown and generally indicated with reference numeral 1100. Apparatus 1100 is the same as apparatus 1000 with the exception that actuator or pusher arms 1124 have diameters significantly less than that of arms 1106, piercing members 1110 are shorter than piercing members 1010, have a rounded or ball shaped proximal end 1111, and are not secured to pusher arms 1124, arms 1106 have longitudinal slots 1107, and a locking member 1126 is provided.

More specifically, each piercing member 1110 has a memory set loop configuration so that it also can function as a surgical clip as shown in FIG. 12C. Although an overlapping loop is shown, a non-overlapping loop can be used. Each piercing member 1110 is positioned within an arm 1106 with the ball shaped proximal end positioned in longitudinally extending slot 1107, which is formed in each arm (FIGS. 12D and E). Slot 1107 has a proximal end that that terminates slightly above piercing member 1110, when piercing member 1110 is positioned as shown in FIG. 12A. The distal end of the slot terminates at a position spaced from the distal end of an arm 1106 by a distance of about 25-33% of the length of the piercing member 1106. The slots are spaced from the distal ends of the arms so that a stop is formed in a respective arm to engage enlarged portion 1111 and stop piercing member 1110 at a desired location as shown in FIGS. 13B and C. With the piercing member locked in this position by the stop and locking member 1126, the apparatus can be positioned within the vessel opening and retracted so that the piercing members penetrate the vessel (e.g., aorta) as shown in FIG. 13C. It should be understood that enlarged portion 1111 can have other suitable shapes as well, such as a flat head shape. Locking member 1126 is an elongated member sized to urge the ball shaped proximal portion 1111 of piercing member 1110 into the slot as shown in FIGS. 12A and B and 13A-D, to lock the piercing member in place.

Although only one arm is shown in FIGS. 13A-D, it should be understood that this is done only for purposes of simplification. Typically, five to twelve arms are used (see e.g., FIG. 12F). Further, although an entire delivery system is not shown in FIG. 12A-E or 13A-E, apparatus 1100 can incorporate the delivery system or mechanism of apparatus 900, including the tubular body or housing 912, finger grips 914, disk or anchor 916 to which arms 1106 are attached, and plunger 918 to which actuator or pusher arms 1124 are attached. This is generally shown in FIG. 12F where housing 1112, which is the same as housing 912, is shown. Arms 1106 differ from those in apparatus 900 as shown in FIGS. 12A-F. Alternatively, arms 1106 and actuator or pusher members 1124 can be incorporated into the delivery apparatus shown in FIGS. 7A-D. In this case, each slotted arm 1106, actuator or pusher member 1124, locking member 1126, and piercing member 1110 combination replaces each arm and piercing member combination in FIG. 7A-D. The proximal portion of arms 1106 include an opening from which the proximal ends of locking members 1126 extend as shown in FIG. 12F.

When using apparatus 1100, the graft is prepared and mounted on the distal ends of arms 1106 and the opening in the target vessel formed in the same manner as described above in connection with other embodiments. The plunger is pushed forward to move the actuator arms 1124 and piercing members 1110 from the withdrawn position shown in FIG. 13A to an extended position as shown in FIG. 13B where a portion of the piercing member has passed through the everted graft and returned to its memory shape, which corresponds to a portion of a loop that has a hook or U-shaped configuration. The arms are moved radially inward as necessary for introduction through the target vessel opening and allowed to expand toward their free state. The entire apparatus is then retracted to that piercing members 1110 penetrate through the target vessel tissue adjacent to the opening as shown in FIG. 13C and a seal between the everted portion of the graft and the tissue surrounding the opening is achieved. Elongated member or trigger wire 1126 presses against the ball shaped proximal end 1111 of the piercing member and forces it into slot 1107 to hold the piercing member in place, while the apparatus is retracted. The pusher member 1124 also can be positioned to urges enlarged portion 1111 of the piercing member against the stop portion of the arm as the base of slot 1107 to assist in locking the piercing member in position. Once all of the piercing members have penetrated through the target vessel tissue (FIG. 13C), elongated locking members 1126 are retracted to release the piercing members (FIG. 13D). The surgeon can individually pull each of the loops formed at the proximal ends of the locking members as shown in FIG. 12F. Alternatively, one can secured any number (e.g., all) of the locking member loops together with a flexible wire, for example, to retract any number or all of the locking members simultaneously. The arms are further retracted allowing each piercing member to be released therefrom and assume its loop shaped configuration (FIG. 13E) to hold the graft and target vessel together. If some leakage appears, sutures or fasteners, such as fastener clips 102, can be placed at the area of concern.

Referring to FIGS. 14A-C and FIGS. 15A and B, yet a further embodiment generally indicated with reference numeral 1200 will be described. Although only one arm is shown for purposes of simplification, it should be understood that generally five to twelve arms are used.

Anastomosis apparatus 1200 also is compatible with any of the delivery systems shown in FIG. 6, 7 or 9. Anastomosis apparatus 1200 has arms that are the same as arms 606 and extend from tubular body 1212. Apparatus 1200 also has piercing members 1210 that are the same as piercing members 1110 with ball shaped proximal ends 1211, sharp distal ends, and a loop shaped memory shape, which although shown as an overlapping loop, can be non-overlapping.

Referring to FIGS. 14 A and B, anastomosis apparatus 1200 incorporates tubular actuating or pusher members 1224, each having a notch 1224N and slot 1224S formed therein. Each slot 1224S extends from notch 1224N to the distal end of a respective arm and is open ended. Each ball shaped end 1211 is seated in a respective notch 1224N with the portion extending from the ball shaped end of the piercing member aligned with a respective slot 1224S. In this manner, each piercing member 1210 moves with a corresponding actuator or pusher member 1224. When the actuator or pusher member 1224 is pushed or moved distally a distance sufficient for the notch 1224N to be outside a respective arm 1206, the piercing member, which was seated therein, is released as shown in FIG. 14C. Alternatively, the arms 1206 can be retracted, while holding the piercing member to move notches 1224N outside of tubular arms 1206.

Anastomosis apparatus 1210 is used in a manner to that described in connection with apparatus 1100. After the graft is prepped and placed over the distal ends of arms 1206 and the piercing members passed through the graft, the surgeon prepares the opening in the target vessel (e.g., the aorta), moves arms 1206 radially inward sufficiently to introduce the arms into the target vessel opening. The surgeon then allows the arms to return toward their free state, fill the opening with the tubular graft, and urge the everted graft against the target vessel tissue surrounding the opening. The entire apparatus is then retracted so that piercing members 1210 penetrate the tissue surrounding the opening in the target vessel as shown in FIG. 15A and a seal is achieved. Thereafter, arms 1206 can be retracted to release piercing members 1210, which then return to their closed loop memory set configuration to hold the graft to the target vessel and complete the anastomosis (FIG. 15B). If some leakage appears, sutures or fasteners, such as fasteners 102, can be placed at the area of concern.

Variations and modifications of the devices and methods disclosed herein will be readily apparent to persons skilled in the art. As such, it should be understood that the foregoing detailed description and the accompanying illustrations, are made for purposes of clarity and understanding, and are not intended to limit the scope of the invention, which is defined by the claims appended hereto.

What is claimed is:

1. Anastomosis apparatus for anastomosing a first tubular structure to a second tubular structure having a sidewall with an opening formed therein, the apparatus comprising a support device having a first portion and a second portion adapted to support an everted portion of the first tubular structure and having a radius and radially adjustable portions, said second portion further including a plurality piercing members slidably coupled to respective ones of said radially adjustable portions and adapted to pierce and hold a portion of said first and second tubular structures; wherein said radially adjustable portions comprise a plurality of arms, each of plurality of arms further having a distal end, each of said piercing members being slidably coupled to one of said plurality of arms; and wherein said arms includes a first position in which said arms collectively define a distally decreasing diameter to said distal ends, and a second position in which a collective diameter defined by said distal ends is greater than a collective diameter defined by said distal ends in said first position, and positions between said first and second position.

2. The apparatus of claim 1 further including a slide slidably coupled to said plurality of arms for movement therealong and having a radial dimension sized to radially expand said arms when moved away from said first portion of said support device.

3. The apparatus of claim 1 wherein said first portion comprises a generally ring shaped member and said arms extend radially from said generally ring shaped member and are slidably mounted thereto.

4. The apparatus of claim 1 wherein said arms are tubular.

5. The apparatus of claim 1 further including an actuator coupled to said piercing members for moving said piercing members.

6. The apparatus of claim 1 further including an actuator coupled to one of said piercing members for moving said piercing members.

7. The apparatus of claim 6 wherein each of said piercing members has a portion with a curved memory shape.

8. The apparatus of claim 7 further including a plurality of fasteners, each of said fasteners being coupled to one of said piercing members.

9. The apparatus of claim 7 further including a plurality of fasteners, each of said fasteners being releasably coupled to one of said piercing members.

10. The apparatus of claim 6 further including a plurality of fasteners, each of said fasteners being coupled to one of said piercing members.

11. The apparatus of claim 10 wherein each of said fasteners is releasably coupled to one of said piercing members.

12. The apparatus of claim 11 wherein said fasteners comprise surgical clips.

13. The apparatus of claim 11 wherein said fasteners comprise self-closing surgical clips.

14. The apparatus of any one of claims 5, 6, 8, 9, 10, 11, 12, or 13 wherein said piercing members are releasably coupled to said actuator.

15. The apparatus of claim 6 wherein each of said piercing members has a closed loop memory shape.

16. The apparatus of claim 1, wherein said plurality of arms extending from said first portion and terminating at a distal end, and further where said apparatus is configured such that a radial spacing between said distal end of opposing ones of said arms is open.

17. Anastomosis apparatus for anastomosing a first tubular structure to a second tubular structure having a sidewall with an opening formed therein, the apparatus comprising a support having a body portion, a plurality of arms extending from said body portion, and a plurality of tissue piercing members each being adapted to pierce a portion of said first and second tubular structures, each of said plurality of arms forming a pathway in which one of said plurality of tissue piercing members is slidably mounted, each of said plurality of arms further having a distal end from which one of said tissue piercing members can be extended and a proximal end, wherein said distal ends collectively adapted to receive an end portion of said first tubular structure everted thereover; wherein said body portion includes a housing and wherein the position of said arms is adjustable from a first position in which said arms collectively define a distally decreasing diameter to said distal ends, to a second position in which a collective diameter defined by said distal ends is greater than a collective diameter defined by said distal ends in said first position.

18. The apparatus of claim 17 further including a slide slidably coupled to said plurality of arms for movement therealong and having a radial dimension sized to radially expand said arms when moved away from said body portion.

19. The apparatus of claim 17 wherein said body portion comprises a generally ring shaped member and said arms extend radially from said generally ring shaped member and are slidably mounted thereto.

20. The apparatus of claim 17 wherein said arms are tubular.

21. The apparatus of claim 20 further including an actuator coupled to said piercing members for moving said piercing member.

22. The apparatus of claim 17 further including an actuator coupled to said piercing members for moving said piercing member.

23. The apparatus of claim 22 wherein each of said piercing members has a portion with a curved memory shape.

24. The apparatus of claim 22 wherein said piercing members have a loop configured memory shape.

25. The apparatus of claim 22 further including a plurality of fasteners, each of said fasteners being coupled to one of said piercing members.

26. The apparatus of claim 25 wherein each of said fasteners is releasably coupled to one of said piercing members.

27. The apparatus of claim 26 wherein each of said piercing members has a portion with a curved memory shape.

28. The apparatus of claim 27 wherein said piercing member portions have a curved memory shape.

29. The apparatus of claim 27 wherein said fasteners comprise surgical clips.

30. The apparatus of claim 27 wherein said fasteners comprise self-closing surgical clips.

31. The apparatus of any one of claims 23, 24, 25, 26, 27, 28, 29, or 30 wherein said piercing members are releasably coupled to said support device.

32. The apparatus of claim 17 wherein each of said piercing members has a portion with a curved memory shape.

33. The apparatus of claim 32 wherein each of said piercing members has a closed loop memory shape.

* * * * *